(12) United States Patent
Chu et al.

(10) Patent No.: US 7,169,155 B2
(45) Date of Patent: Jan. 30, 2007

(54) METHODS AND APPARATUS FOR GUIDING A NEEDLE

(75) Inventors: Michael S. H. Chu, Brookline, MA (US); Armand A. Morin, Berkley, MA (US); Barry N. Gellman, N. Easton, MA (US); Jozef Slanda, Milford, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 349 days.

(21) Appl. No.: 10/017,012

(22) Filed: Dec. 14, 2001

(65) Prior Publication Data
US 2003/0114862 A1 Jun. 19, 2003

(51) Int. Cl.
*A61B 19/00* (2006.01)
(52) U.S. Cl. .................................................. 606/130
(58) Field of Classification Search ................ 606/130; 600/417
See application file for complete search history.

(56) References Cited

U.S. PATENT DOCUMENTS

| | | | |
|---|---|---|---|
| 2,338,800 A | 1/1944 | Burke | |
| 2,432,294 A | 12/1947 | Dimmer | |
| 2,697,433 A * | 12/1954 | Zehnder | 606/96 |
| 2,705,949 A | 4/1955 | Silverman | |
| 3,115,140 A | 12/1963 | Volkman | 128/410 |
| 3,349,762 A | 10/1967 | Kapany | |
| 3,356,089 A | 12/1967 | Francis | |
| 3,457,922 A | 7/1969 | Ray | |
| 3,538,916 A | 11/1970 | Wiles et al. | |
| 3,556,085 A | 1/1971 | Takahashi | |
| 3,941,121 A | 3/1976 | Olinger et al. | |
| 3,961,621 A | 6/1976 | Northeved | |
| 4,187,848 A | 2/1980 | Taylor | |
| 4,230,123 A | 10/1980 | Hawkins, Jr. | |
| 4,269,192 A | 5/1981 | Matsuo | |
| 4,274,408 A | 6/1981 | Nimrod | |
| 4,332,248 A | 6/1982 | DeVitis | |
| 4,356,822 A | 11/1982 | Winstead-Hall | |
| 4,401,124 A | 8/1983 | Guess et al. | |
| 4,405,314 A | 9/1983 | Cope | |

(Continued)

FOREIGN PATENT DOCUMENTS

DE 29519103 U1 1/1997

(Continued)

OTHER PUBLICATIONS

American Urological Association, Inc., Ureteral Stones Pamphlet, pp. 1-5, 7-8 (1997).

(Continued)

*Primary Examiner*—Michael Thaler
(74) *Attorney, Agent, or Firm*—Finnegan, Henderson, Farabow, Garrett & Dunner, L.L.P.

(57) ABSTRACT

A needle is guided to a target along a pre-determined needle insertion trajectory. A method that utilizes a fluoroscope can be used to locate the target. The target can be an internal structure within the human body. A device can be used with the fluoroscope to aim and insert a needle or sharp probe along the predetermined trajectory to the target. By using the device with the fluoroscope, a user can receive real time visual confirmation of contact between the needle and the target.

40 Claims, 50 Drawing Sheets

U.S. PATENT DOCUMENTS

| | | |
|---|---|---|
| 4,485,815 A | 12/1984 | Amplatz et al. |
| 4,512,351 A | 4/1985 | Pohndorf |
| 4,566,438 A | 1/1986 | Liese et al. |
| 4,572,203 A | 2/1986 | Feinstein |
| 4,582,061 A | 4/1986 | Fry |
| 4,629,451 A | 12/1986 | Winters et al. |
| 4,639,247 A | 1/1987 | Bokros |
| 4,645,490 A | 2/1987 | Rosenberg |
| 4,668,222 A | 5/1987 | Poirier |
| 4,693,703 A | 9/1987 | Rosenberg |
| 4,705,510 A | 11/1987 | Rosenberg |
| 4,710,171 A | 12/1987 | Rosenberg |
| 4,718,433 A | 1/1988 | Feinstein |
| 4,750,487 A | 6/1988 | Zanetti |
| 4,787,892 A | 11/1988 | Rosenberg |
| 4,805,615 A | 2/1989 | Carol .................... 128/303 B |
| 4,834,708 A | 5/1989 | Pillari |
| 4,869,259 A | 9/1989 | Elkins |
| 4,874,376 A | 10/1989 | Hawkins, Jr. |
| 4,886,502 A | 12/1989 | Poirier et al. |
| 4,897,081 A | 1/1990 | Poirier et al. |
| 4,899,729 A | 2/1990 | Gill et al. |
| 4,945,895 A | 8/1990 | Takai et al. |
| 4,977,897 A | 12/1990 | Hurwitz |
| 4,981,142 A | 1/1991 | Dachman |
| 4,997,424 A | 3/1991 | Little |
| 4,998,938 A | 3/1991 | Ghajar et al. |
| 5,006,115 A | 4/1991 | McDonald |
| 5,009,644 A | 4/1991 | McDonald |
| 5,020,088 A | 5/1991 | Tobin ..................... 378/164 |
| 5,047,036 A | 9/1991 | Koutrouvelis |
| 5,048,530 A | 9/1991 | Hurwitz |
| 5,059,186 A | 10/1991 | Yamamoto et al. |
| 5,078,142 A | 1/1992 | Siczek et al. |
| 5,080,662 A | 1/1992 | Paul |
| 5,081,997 A | 1/1992 | Bosley, Jr. et al. |
| 5,098,397 A | 3/1992 | Svensson et al. |
| 5,104,381 A | 4/1992 | Gresl et al. |
| 5,129,911 A | 7/1992 | Siczek et al. |
| 5,135,001 A | 8/1992 | Sinofsky et al. |
| 5,139,511 A | 8/1992 | Gill et al. |
| 5,189,690 A | 2/1993 | Samuel |
| 5,201,314 A | 4/1993 | Bosley et al. |
| 5,201,742 A | 4/1993 | Hasson |
| 5,221,269 A | 6/1993 | Miller et al. |
| 5,242,415 A | 9/1993 | Kantrowitz et al. |
| 5,242,455 A | 9/1993 | Skeens et al. |
| 5,250,025 A | 10/1993 | Sosnowski et al. |
| 5,259,837 A | 11/1993 | Van Wormer |
| 5,263,938 A | 11/1993 | Orr et al. |
| 5,289,831 A | 3/1994 | Bosley |
| 5,308,352 A | 5/1994 | Koutrouvelis |
| 5,314,432 A | 5/1994 | Paul |
| 5,327,891 A | 7/1994 | Rammler |
| 5,383,466 A | 1/1995 | Partika |
| 5,395,317 A | 3/1995 | Kambin |
| 5,409,497 A | 4/1995 | Siczek et al. |
| 5,439,444 A | 8/1995 | Andersen et al. |
| 5,489,273 A | 2/1996 | Whitney et al. |
| 5,490,521 A | 2/1996 | Davis et al. |
| 5,556,385 A | 9/1996 | Andersen |
| 5,571,091 A | 11/1996 | Davis et al. |
| 5,575,798 A | 11/1996 | Koutrouvelis |
| 5,586,553 A | 12/1996 | Halili et al. |
| 5,588,436 A | 12/1996 | Narayanan et al. |
| 5,626,597 A | 5/1997 | Urban et al. |
| 5,665,072 A | 9/1997 | Yoon |
| 5,665,095 A | 9/1997 | Jacobson |
| 5,670,161 A | 9/1997 | Healy et al. |
| 5,676,656 A | 10/1997 | Brimhall |
| 5,680,859 A | 10/1997 | Urion et al. |
| 5,693,072 A | 12/1997 | McIntosh |
| 5,725,506 A | 3/1998 | Freeman et al. |
| 5,749,887 A | 5/1998 | Heske et al. |
| 5,759,154 A | 6/1998 | Hoyns |
| 5,766,135 A | 6/1998 | Terwilliger |
| 5,769,795 A | 6/1998 | Terwilliger |
| 5,779,665 A | 7/1998 | Mastrototaro et al. |
| 5,792,044 A | 8/1998 | Foley et al. |
| 5,799,055 A | 8/1998 | Peshkin et al. |
| 5,820,554 A | 10/1998 | Davis et al. |
| 5,820,600 A | 10/1998 | Carlson et al. |
| 5,830,190 A | 11/1998 | Howell |
| 5,833,655 A | 11/1998 | Freed et al. |
| 5,843,023 A | 12/1998 | Cecchi |
| 5,851,183 A | 12/1998 | Bucholz |
| 5,871,445 A | 2/1999 | Bucholz |
| 5,902,231 A | 5/1999 | Foley et al. |
| 5,921,933 A | 7/1999 | Sarkis et al. |
| 5,967,988 A | 10/1999 | Briscoe et al. |
| 6,006,750 A | 12/1999 | Field |
| 6,018,676 A | 1/2000 | Davis et al. |
| 6,053,871 A | 4/2000 | Cockburn |
| 6,106,473 A | 8/2000 | Violante et al. |

FOREIGN PATENT DOCUMENTS

| | | |
|---|---|---|
| EP | 0904741 A2 | 3/1999 |
| WO | 93/10837 | 6/1993 |
| WO | 96/00044 | 1/1996 |
| WO | 96/33667 | 10/1996 |
| WO | 99/00056 | 1/1999 |
| WO | 99/16374 | 4/1999 |
| WO | 00/64354 | 11/2000 |

OTHER PUBLICATIONS

Boston Scientific/Microvasive Education Center, "Percutaneous Nephrolithotomy," pp. 1-10 (1995).

Cadeddu et al., "Stereotactic Mechanical Percutaneous Renal Access," *Journal of Endourology*, vol. 12, No. 2, (Apr. 1998).

Caronia et al., "Rettopessi per via laparoscopica: nostra esperienza nel trattamento del prolasso rettale completo," *Giorn. Chir.*, vol. 20-n.6/7, pp. 311-313, (1999), with English Abstract.

Cook Urological, Inc., "Disposable Two-Part Trocar Needles," 1 page, (1998).

Cook Urological, Inc., "Amplatz Needle Holder," 1 page, (1998).

Cook Urological, Inc., "Disposable Long Trocar Needles," 1 page, (1998).

Cook Urological, Inc., "Disposable Mitty-Pollack Needle Set," 1 page, (1998).

Cook Urological, Inc., "Disposable TFE Sheath Needle," 1 page, (1998).

Cook Urological, Inc., "Cook-Cope Loop Catheter Introduction Set," 1 page, (1998).

Cook Urological, Inc., "Percutaneous Entry Set," 2 pages, (1998).

Cook Urological, Inc., "NEFF Percutaneous Access Sets with RB™ Design Radiopaque Band," 1 page, (1995).

Cook Urological, Inc., "NEFF Percutaneous Access Sets with Radiopaque Band and Hydrophilic Coating," 2 pages, (1997).

Cook Urological, Inc., "Ultrathane® Amplatz Ureteral Stent Sets with Slip-Coat™ Hydrophilic Coating and RB™ Radiopaque Bands," 1 page, (1996).

Cook Urological, Inc., "Ultrathane Dawson-Mueller Drainage Catheters with Mac Loc™ Locking Mechanism, Slip-Coat™ Hydrophilic Coating and Intro-Tip™ Design Introduction System," 1 page, (1997).

Cook Urological, Inc., "Yueh Centesis Disposable Catheter Needles," 1 page, (1996).

Cook Urological, Inc., "Geremia Vertebral Biopsy Needle Set," 1 page, (1994).

Engineering News, "Engineers Keep Things Green," *Design News*, (Nov. 2, 1998).

Fielding, "Laparoscopic Cholecystectomy," *Aust. N.Z. J. Surg.*, vol. 62, pp. 181-187, (1992).

Gotlieb et al., "Intraperitoneal Pressures and Clinical Parameters of Total Paracentesis for Palliation of Symptomatic Ascites in Ovarian Cancer," *Gynecologic Oncology*, vol. 71, pp. 381-385, (1998).

Jenkins et al., "Veres Needle in the Pleural Space," *Southern Medical Journal*, vol. 76, No. 11, pp. 1383-1385, (Nov. 1983).

Köckerling et al., "Die Offene Laparoskopie zur Vermeidung von Punktionsverletzungen," *Chirurg*, vol. 67, pp. 183-187, (1996), with English summary section.

LeRoy, "Percutaneous Access," in *Smith's Textbook of Endourology*, vol. 1, pp. 199-210, (1996).

Smith, "Percutaneous Removal of Kidney Stones," Urologic Surgery, pp. 116-131 (date unknown).

Microvasive Product Catalog; Products for Endourology, p. 8-2, (1996).

International Search Report for PCT/US99/28311, Aug. 1, 2000, 8 pgs.

International Search Report for International Patent Application No. PCT/US02/39187, dated Apr. 16, 2003, 8 pages.

* cited by examiner

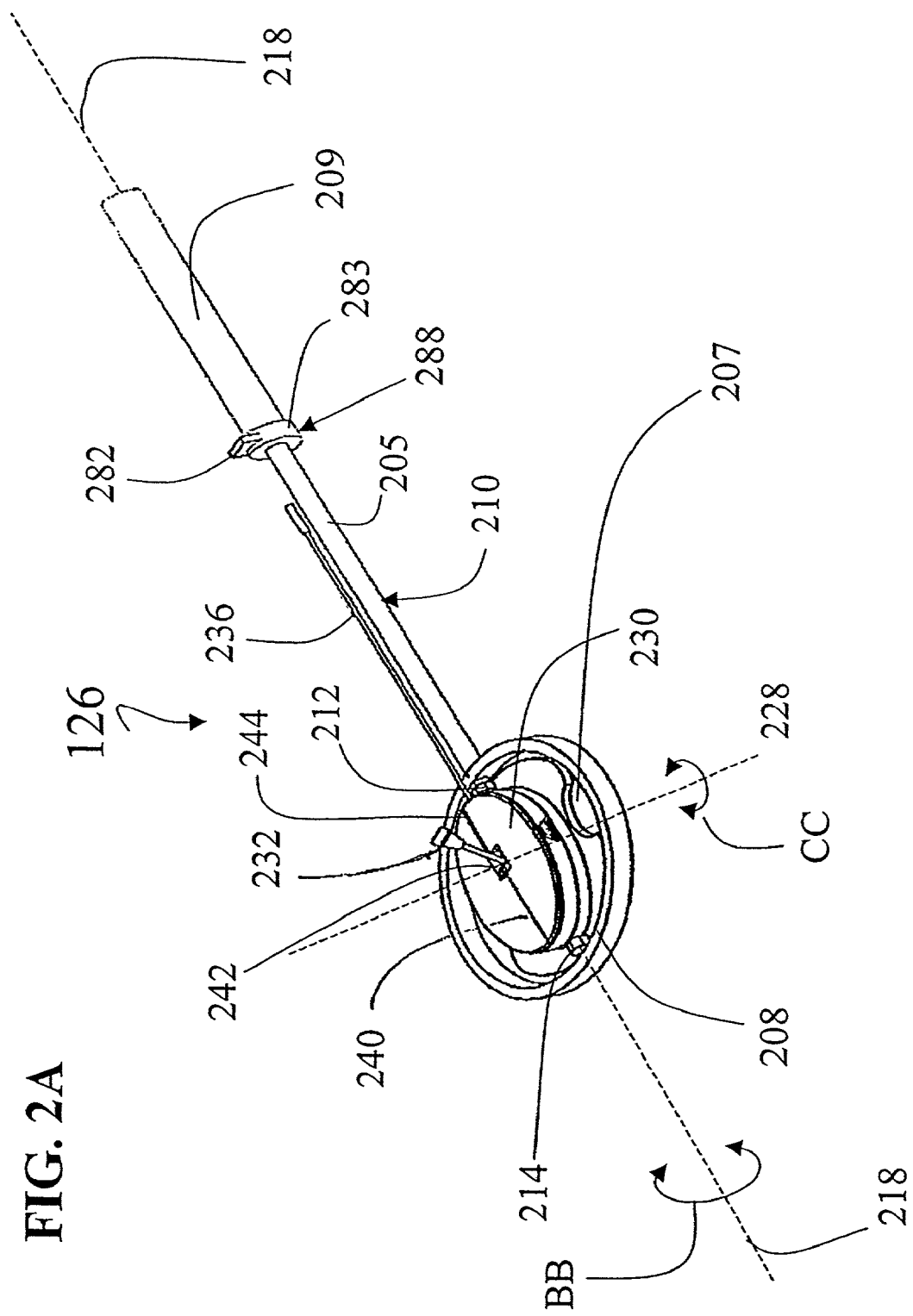

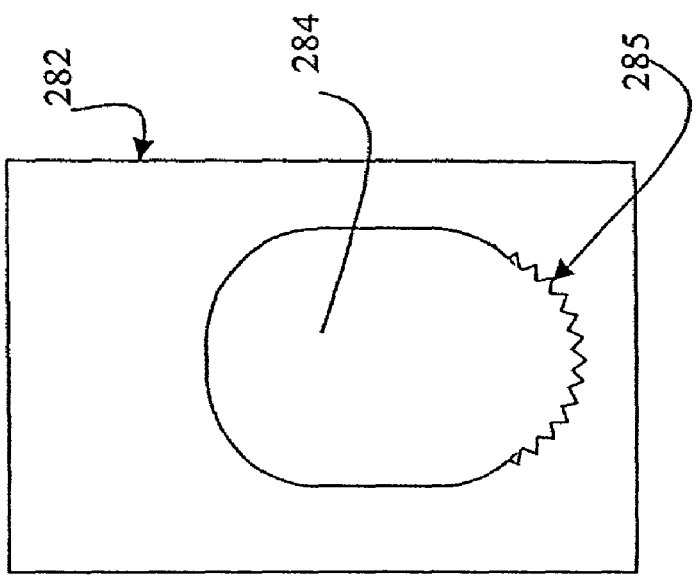
FIG. 2I
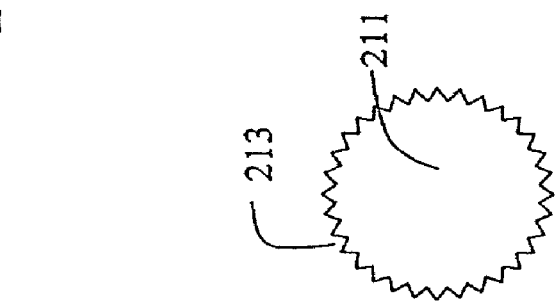
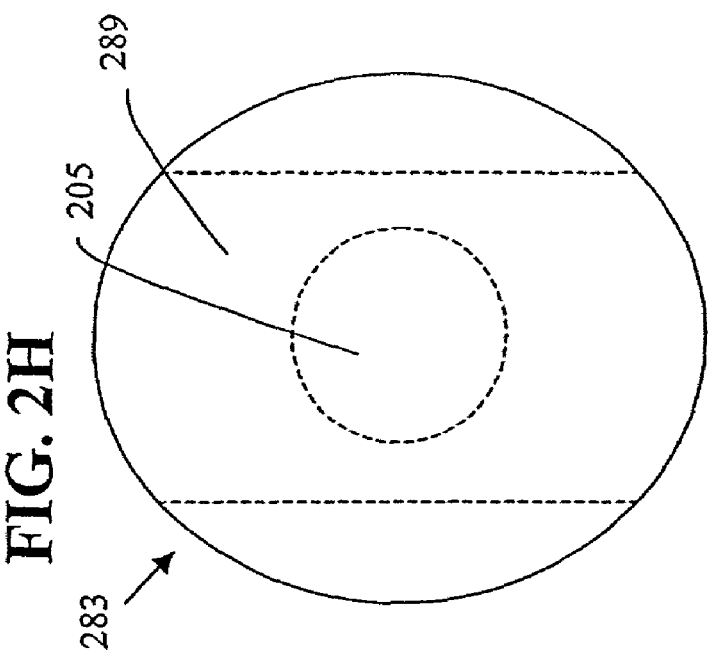
FIG. 2H

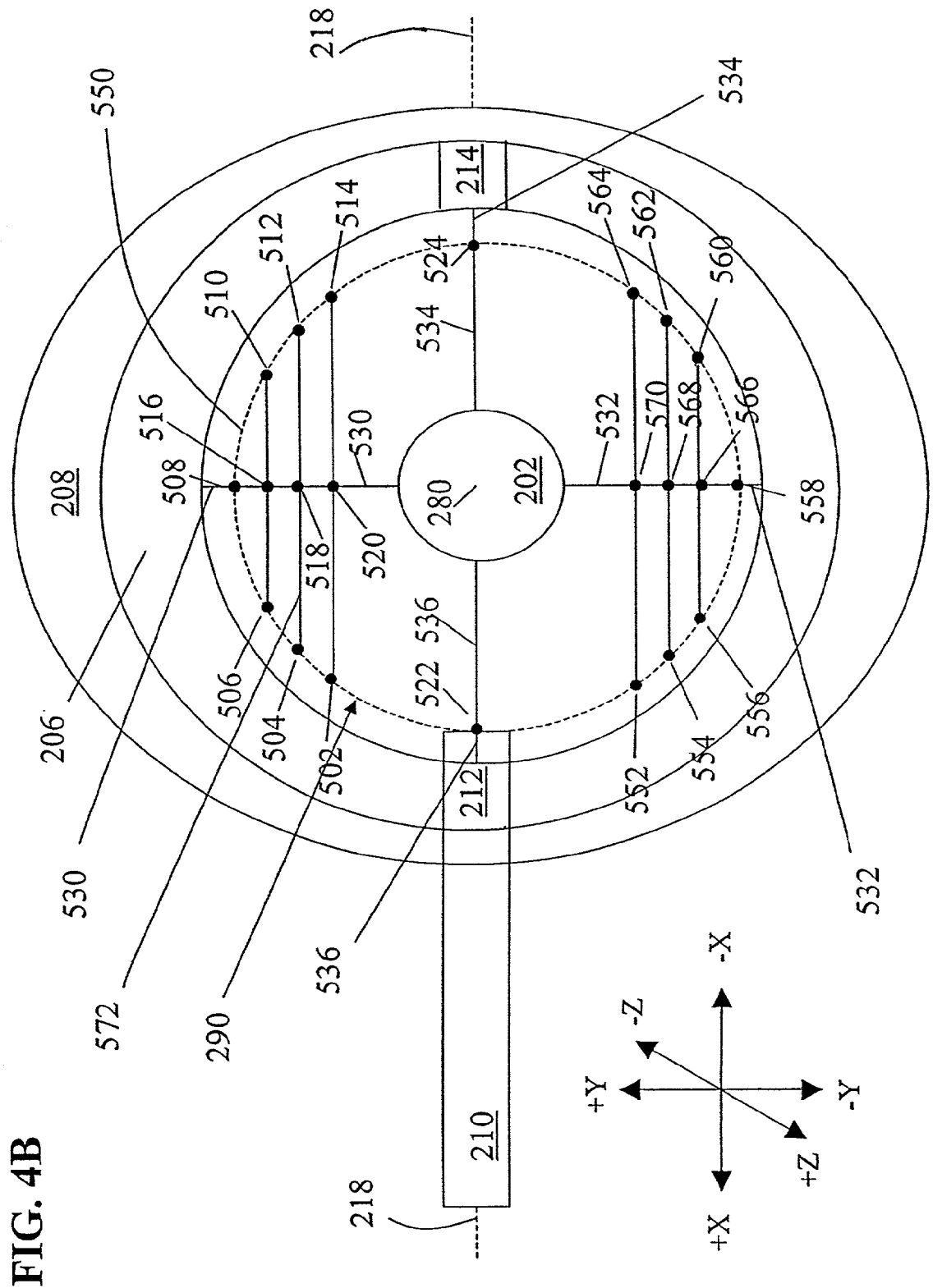

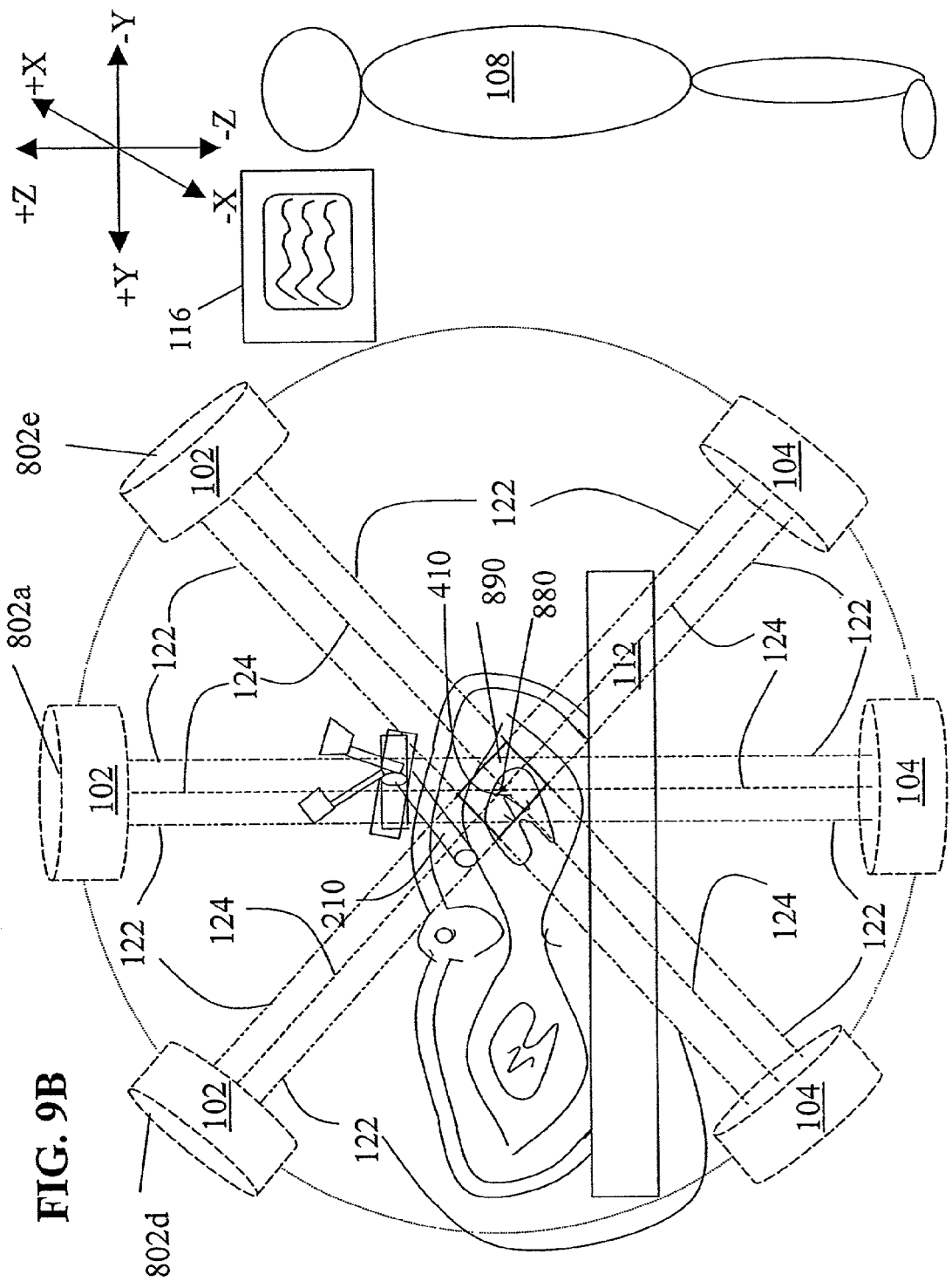

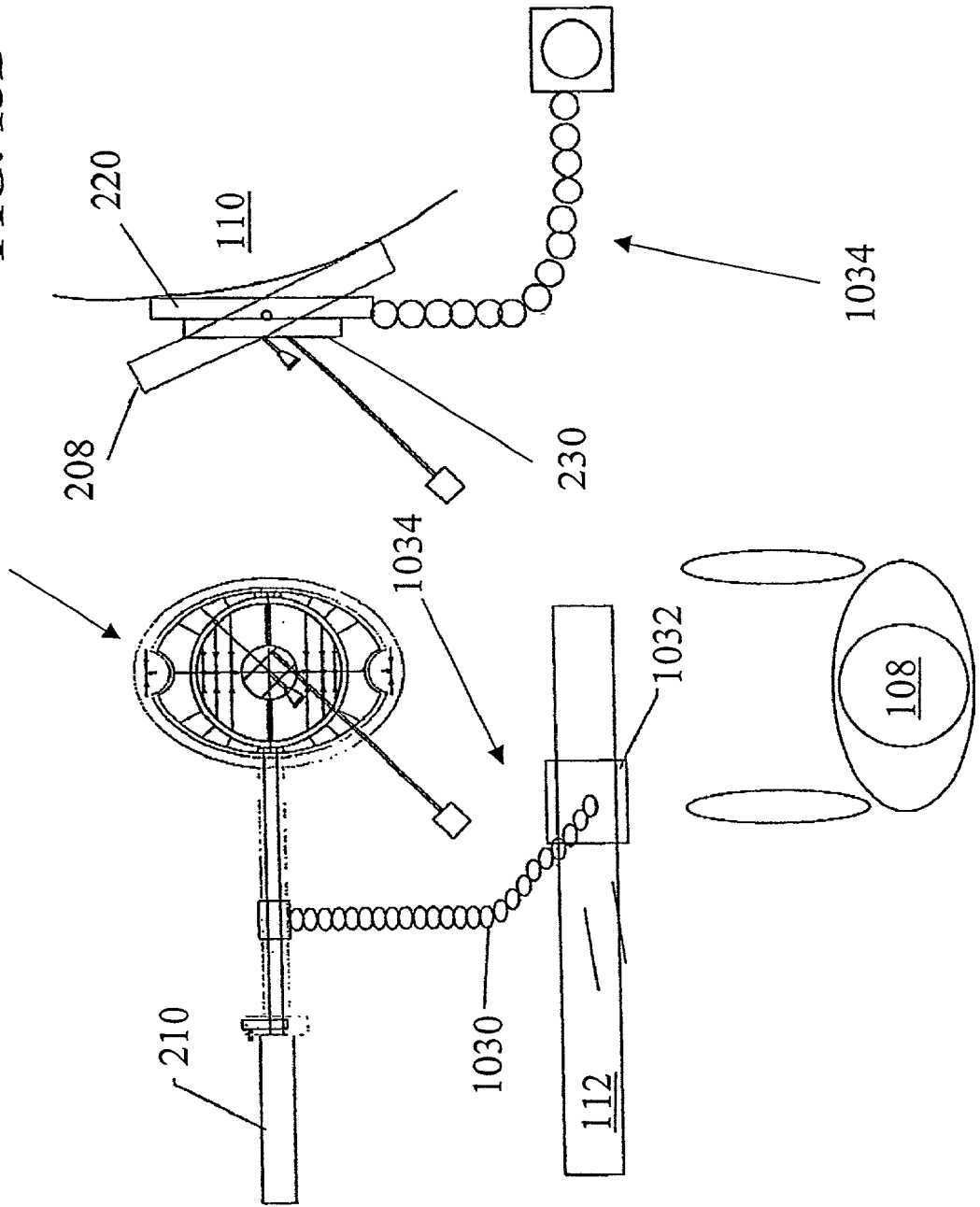

METHODS AND APPARATUS FOR GUIDING A NEEDLE

TECHNICAL FIELD

The invention generally relates to devices and methods for guiding a needle to a target. More particularly, the invention can be used to guide the path of a needle along a selected trajectory towards a target that is located within a patient.

BACKGROUND INFORMATION

Many medical procedures are undertaken through small tracts formed within a patient's tissue. Such procedures generally are referred to as "minimally invasive." In order to form the tract running from outside of the patient to a target within the patient, a probe typically is inserted in the initial stages of a procedure. This probe extends from the surface of the patient's skin to the target inside the patient's body. Later in the procedure, the passageway formed by the probe can be widened to accommodate other and larger diameter medical devices necessary for the procedure.

Typically, inserting the probe is a time-consuming procedure. The probe must be positioned properly, typically under the guidance of an energy emitting medical device, such as an x-ray emitting device, and a fluoroscope. X-ray energy passes through the patient's body and differentially impinges on a fluoroscope receiver. In response, the fluoroscope receiver generates electronic signals that are transmitted to a fluoroscope display screen. Signals received by the fluoroscope display screen excite fluorescent material, such as calcium tungstate, to create a screen display of the body and probe. The probe is visualized on the fluoroscope screen as it enters the patient. The probe appears on the screen because it does not allow the energy to pass through it (i.e., it is opaque to the X-ray energy).

SUMMARY OF THE INVENTION

The invention provides devices and methods for guiding a probe, such as a needle or other penetrating object, into a patient. The probes is aimed and directed along one of many possible trajectories towards a target. The target may be hidden from human eyesight and could be, for example, an internal structure within the human body. A trajectory directed towards the target can be selected from many possible trajectories identified and provided for by the device. A selected trajectory can define a point of contact and direction of contact of the probe with respect to the target and also can define an insertion point of the probe with respect to, for example, the outer surface of a human body. The insertion point of the probe can be a location along the surface of the human body from which to insert and move the probe towards the target.

The invention can be used with a vision enhancing device, such as an energy emitting device and a fluoroscope with its visual display, to identify the location of a target and to determine an insertion point and a trajectory for directing the probe towards the target. The device has portions that are visible to an unaided eye and/or are visible on a fluoroscope display. These portions can be used to target the device. The invention also facilitates visual confirmation of the location and movement of the probe and/or its contact with the target while the probe and/or target may be hidden from human eyesight.

In one aspect of the invention is a needle guiding apparatus can include a base defining an opening through it and a guide platform disposed adjacent to the opening that is rotatable about a rotation axis that extends through the opening. A common point can be located along the rotation axis.

The needle guiding apparatus can include a pivot disposed at least partially within the guide platform. The pivot can be rotatable about a pivot axis that is substantially perpendicular to the rotation axis. In certain embodiments, the guide shaft can be disposed at least partially within the pivot. The guide shaft can extend along a longitudinal axis from a first end of the guide shaft to a second end of the guide shaft and the longitudinal axis can intersect with the rotation axis at the common point. The guide shaft can include a radiopaque material between the first end, and a locus along the guide shaft can be normal to the longitudinal axis at the common point. The radiopaque material can extend to the locus and the locus can be located immediately adjacent to a material being less radiopaque than the radiopaque material. The embodiment described above or below can have any of the following features.

In some embodiments, the pivot axis intersects the rotation axis at the common point. Certain embodiments can have a common point that is located at the second end of the guide shaft. Some embodiments can have a guide shaft that comprises an inner wall of the pivot forming a bore. Certain embodiments can have a guide shaft is disposed at least partially within an inner wall in the pivot forming a bore.

In some embodiments, the guide shaft is rotatable about the rotation axis and the pivot axis. Certain embodiments can have an entire guide shaft between the first end and the locus comprising the radiopaque material. Some embodiments can have a guide rod that is connected to the pivot and is rotatable about the rotation axis and the pivot axis to transfer rotational movement to the guide shaft. Certain embodiments can have a guide rod lock is employed to prevent movement of the pivot.

In some embodiments, the apparatus can include a grid disposed about the rotation axis. Certain embodiments can include a radiopaque point disposed proximate to the guide platform. Some embodiments can include a radiopaque line segment disposed proximate to the guide platform.

In some embodiments, the apparatus can include a shaft connected to the base. The shaft extends along a shaft axis perpendicular to the rotation axis. Certain embodiments can include an outer rim disposed about the base where the outer rim is rotatable around the shaft axis. Some embodiments can also include an outer rim lock for preventing relative movement between the outer rim and the base.

In another aspect, the invention is a method of guiding a needle to a target. The method includes the step of positioning a fluoro axis in a first fluoro position intersecting a target. The fluoro axis is defined by an energy emitter at a first point and an energy receiver at a second point. The method also includes the step of selecting a starting point on a needle guiding apparatus.

The needle guiding apparatus includes a guide platform being rotatable about a rotation axis. The rotation axis has a common point along the rotation axis and a pivot disposed at least partially within the guide platform and is rotatable about a pivot axis that is substantially perpendicular to the rotation axis.

The needle guiding apparatus also includes a guide shaft disposed at least partially within the pivot and that extends along a longitudinal axis from a first end of the guide shaft to a second end of the guide shaft. The longitudinal axis intersects with the rotation axis at the common point. The guide shaft includes a radiopaque material between the first end and a locus along the guide shaft that is normal to the longitudinal axis at the common point. The radiopaque material extends to the locus and the locus is located immediately adjacent to a material being less radiopaque than the radiopaque material. The starting point is disposed adjacent to the rotation axis and an aiming line radiates perpendicularly from the rotation axis.

The method also includes the steps of positioning the guide platform in a first imaging position where the fluoro axis intersects the starting point. Next, positioning the fluoro axis in a second fluoro imaging position intersecting the common point and the target and positioning the guide platform such the aiming line substantially aligns with the starting point, and then positioning the guide shaft such that the longitudinal axis is parallel with the fluoro axis in the second fluoro position.

In some embodiments, the method includes inserting a needle through the guide shaft along the longitudinal axis. In the above embodiment, the method can further include the step of viewing a device for displaying a visual representation of radiopaque material between the energy emitter and the energy receiver.

In some embodiments of the method, the step of positioning the guide platform such that the aiming line substantially aligns with the starting point occurs prior to the step of positioning the second fluoro position.

BRIEF DESCRIPTION OF THE DRAWINGS

The invention, and exemplary embodiments according to the invention, are more particularly described in the following description, taken in conjunction with the accompanying drawings. In the drawings, the same and/or similar reference characters generally refer to the same parts throughout the different views and embodiments. Also, the drawings are not necessarily to scale, emphasis instead generally being placed upon illustrating principles of the invention.

FIG. 2A is a schematic top perspective view of an embodiment of a needle guiding device.

FIG. 2H is a schematic cross section taken generally along line AAA—AAA in FIG. 2E of a slot of the sleeve locking mechanism of the embodiment of the needle guiding device shown in FIG. 2A.

FIG. 2I is a schematic cross section taken generally along line AAA—AAA in FIG. 2E of the vertical plate of the sleeve locking mechanism of the embodiment of the needle guiding device shown in FIG. 2A.

FIG. 4B is a schematic top view of the embodiment of the needle guiding device shown in FIG. 2A which excludes the guide platform and exposes the top surface of the base plate having an imaging grid.

FIG. 9B is a schematic end-on cross-sectional view depicting movement of the fluoroscope emitter and fluoroscope receiver along an Y-Z vertical plane as depicted in the arrangement of FIG. 1A.

FIGS. 13A–13B are different schematic side perspective views of the needle guiding device mounted on a flexible stand.

DESCRIPTION

The invention enables a medical professional to guide a probe, such as a needle or other penetrating object, towards an target located inside the body of a patient. The probe can be aimed and directed towards a target along one of many possible trajectories circumventing vital structures inside the patient. The target may be hidden from human eyesight and could be, for example, an internal structure within the human body. A trajectory directed towards the target can be selected from many possible trajectories identified and provided for by the needle guiding device according to the invention. A selected trajectory can define a point of contact and direction of contact of the probe with respect to the target and also can define an insertion point of the probe with respect to, for example, the outer surface of a human body. The insertion point of the probe can be a location along the surface of the human body from which to insert and move the probe towards the target.

The invention can be used with a vision enhancing device, such as an energy emitting device and a fluoroscope with its visual display, to identify the location of a target and to determine an insertion point along the outer skin surface of the patient and to determine a trajectory for directing the probe towards the target. The needle guiding device has portions that are visible to an unaided eye and/or are visible on a fluoroscope display. The needle guiding device can act as a point of reference that is visible to an unaided eye and visible on a fluoroscope display. These portions can be used to position and aim the needle guiding device towards a target. The invention also facilitates visual confirmation of the location and movement of the probe and/or its contact with the target while the probe and/or target may be hidden from human eyesight.

Devices and methods according to the invention can assist a medical professional in a number of ways. For example, they can reduce the number of times a medical professional inserts a probe into a patient in an attempt to locate a target (and can reduce the length of time such a procedure might take). The invention provides a step-wise procedure to the medical professional. Additionally, the devices and methods of the invention keep the medical professional's hands out of the x-ray energy generated in conjunction with the fluoroscope, reducing health risks to the medical professional. Moreover, due to its step-wise nature, a procedure according to the invention is amenable to training medical professionals in using the devices of the inventor. Also, the devices and methods according the invention can simplify directing a probe towards a target from a three-dimensional problem to a "two-dimensional" problem when viewed on a fluoroscope display. Furthermore, the devices and methods of the invention allow a medical professional to use a triangulation technique to view a probe during insertion.

Figure 1A:
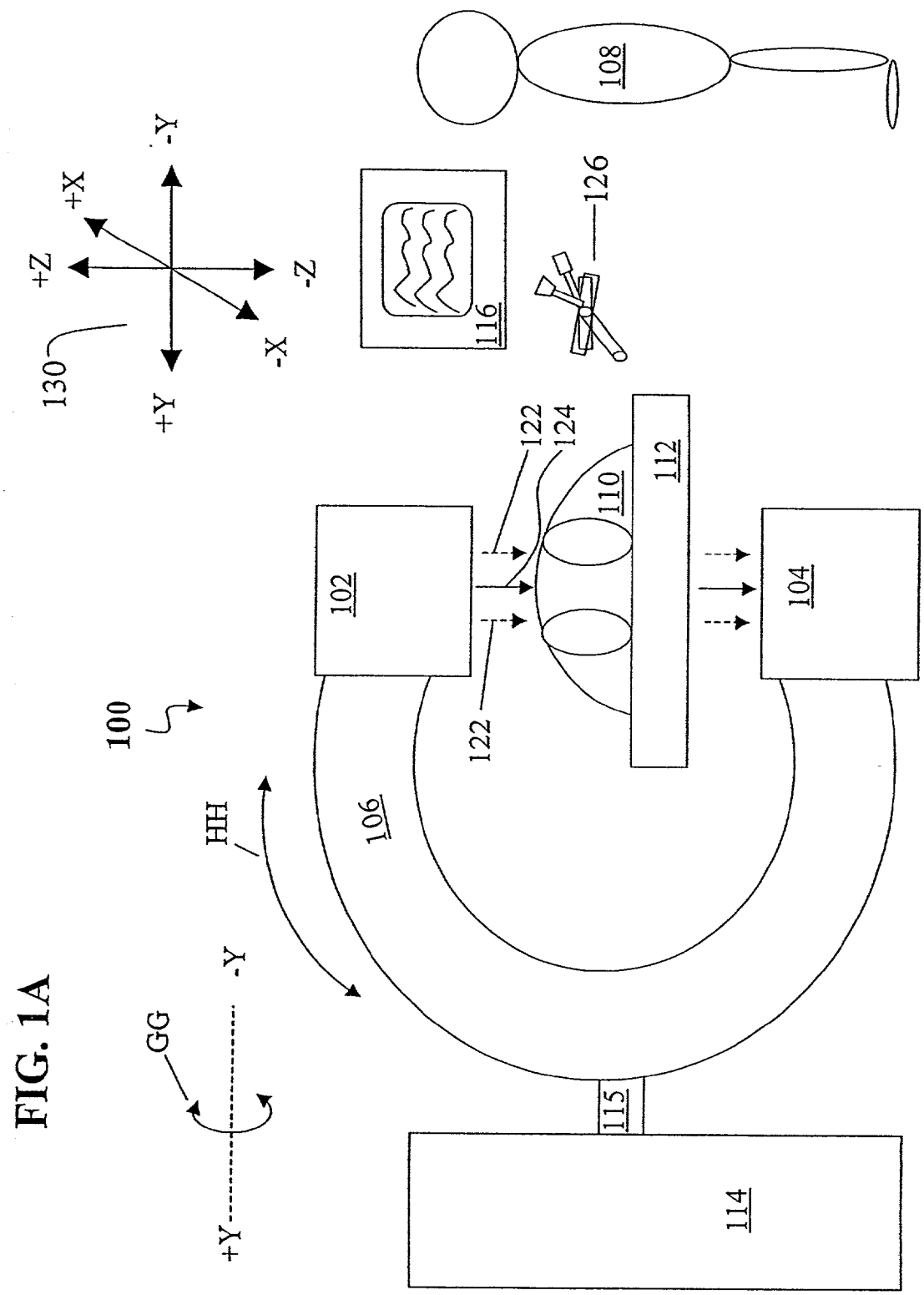
FIG. 1A is a schematic end view of one exemplary arrangement of a patient, medical equipment, and a medical professional.
Figure 1B:
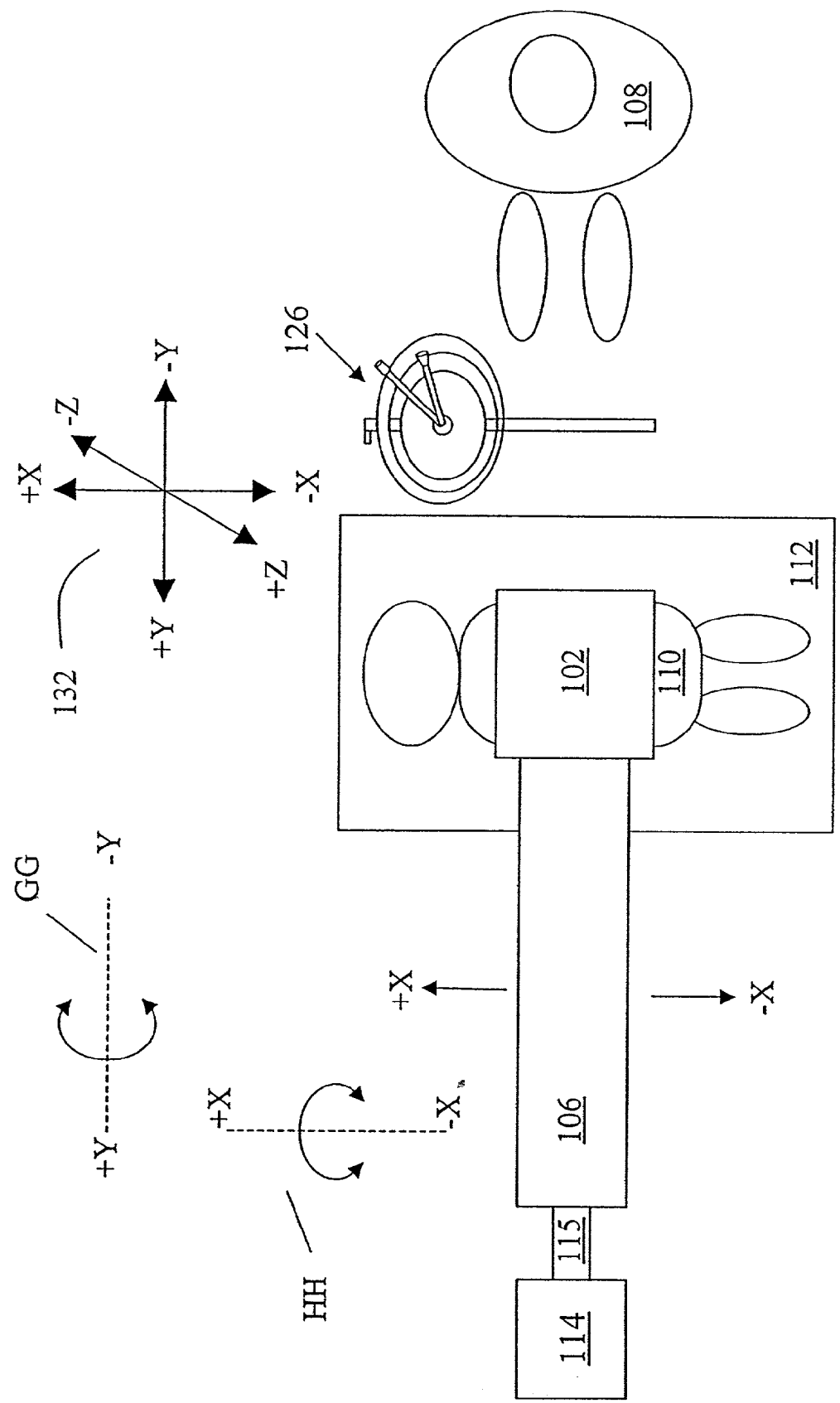
FIG. 1B is a schematic top perspective view of the arrangement of FIG. 1A.

Referring to FIGS. 1A–1B, a particular arrangement of medical equipment is shown for the purpose of illustrating the environment in which the invention may exist and be used. Other arrangements are possible. A patient lies on an operating table 112 near a medical professional 108. The operating table 112 has a long and short dimension. The medical professional 108 faces the patient, and the patient's feet are to the left side of the medical professional 108.

A fluoroscope 100 includes a fluoroscope support 114, a rotation axial 115, a fluoroscope arm 106, a fluoroscope emitter 102, a fluoroscope receiver 104 and a fluoroscope display 116. The fluoroscope 100 is located on the side of the patient 110 opposite from the medical professional 108. The fluoroscope 100 is utilized by the medical professional 108 to visualize physical structures that are inside the patient 110. The fluoroscope emitter 102 directs a column of x-ray energy 122 towards the fluoroscope receiver 104. This column of x-ray energy 122 typically has a circular cross-sectional area with a diameter of about 6 inches.

The fluoroscope receiver 104 receives and captures the x-ray energy emitted from the fluoroscope emitter 102 and measures the intensity of the x-ray energy received from the fluoroscope emitter 102. The fluoroscope receiver 104 transmits electronic signals representing the measured intensity of the received x-ray energy to a fluoroscope display screen 116. The x-ray energy received by the fluoroscope receiver 116 excites material, such as calcium tungstate. The measured intensity of the excitement of the calcium tungstate represents the measured intensity of the received x-ray energy received by the fluoroscope receiver 104. The fluoroscope receiver 104 converts the excitement of the calcium tungstate into electronic signals and transmits these electronic signals to the fluoroscope display 116. The fluoroscope display 116 is a monitor that provides a visual representation of the body of the patient 110 and the probe. The probe is visualized on the fluoroscope display 116 as it enters the patient.

The fluoroscope arm 106 can be attached to the fluoroscope emitter 102 and the fluoroscope receiver 104 in a manner that ensures that x-ray energy emitted by the fluoroscope emitter 102 is directed towards and captured by the fluoroscope receiver 104. A line located within the fluoro beam 122 and intersecting both the fluoroscope emitter 102 and the fluoroscope receiver 104 is referred to as a fluoro axis 124. In this embodiment, the fluoro axis 124 is located at the center of the cross-section of the fluoro beam 122. When the fluoroscope arm 106 is repositioned, the direction and position of the fluoro axis 124 within 3-dimensional space is altered.

When passing through some types of matter, the x-ray energy is reduced in intensity or attenuated. The x-ray attenuating properties of various types of matter vary. For example, air does not significantly reduce x-ray intensity. Flesh and other soft body tissue reduce x-ray intensity more than air but less than bone tissue. As used herein, the term "radiopaque" means a substance that at least partially prevents transmission (by blocking, reflecting, absorbing, defracting, and/or any similar phenomenon) of at least one type of electromagnetic radiation, such that an image of the substance will appear on a display, such as a fluoroscope display 116. Bismuth subcarbonate and stainless steel are examples of a radiopaque material. Also, any type of metal that is biocompatible or metal that is covered with a biocompatible plastic functions as a radiopaque material. Also, a radiopaque ink can be printed or stamped out of sheet metal to form radiopaque markings.

The fluoroscope display 116 visually represents the intensity of the x-ray energy received by the fluoroscope receiver 104 from the fluoroscope emitter 102. The intensity of x-ray energy received at any point within the cross-sectional area of the fluoro beam 122 indicates the attenuating properties of any matter that the x-ray energy has passed through between the fluoroscope emitter 102 and the fluoroscope receiver 104. Radiopaque material significantly reduces the intensity of x-ray energy passing through it and produces a distinguishable effect on the image of the fluoroscope display 116.

For example, if the material blocks x-ray transmission, a "shadow" of the material is shown on the fluoroscope display 116. Transparent materials do not produce a distinguishable effect on the display image 116 and are substantially absent in the fluoroscope display 116. Materials that are visible to the human eye may not be visible in the fluoroscope display 116. For example, the exterior of the patient's body, as defined by the contours of the surface of her skin, is visible to the human eye but is not substantially radiopaque.

A needle guiding device 126 is utilized by the medical professional 108 to aim and guide a needle towards a target along a needle insertion trajectory selected by the medical professional 108. The needle guiding device 126 is at least partially constructed from radiopaque material, and is visible in the fluoroscope display 116 when it is positioned within the fluoro beam 122. The target is typically inside patient 110 and the medical professional 108 utilizes knowledge of the relative positioning of the needle guiding device 126 and the fluoro axis 124 to aim and guide a needle towards the target.

For the purpose of illustrating operation of the needle guiding device 126, X, Y, and Z axes 130 are used to describe the position of the fluoro axis 124 with respect to the position of the needle guiding device 126. The X and Y axes are geometric lines in 3 dimensional space that are substantially horizontal to the surface of the earth (and substantially horizontal with respect to the table 112), perpendicular to each other and perpendicular to the direction of gravity.

The horizontal view of this figure is directed substantially parallel to the X axis and substantially perpendicular to the Y axis and to the Z-Y vertical plane. The Y axis is a geometric line in 3 dimensional space that is horizontal to the surface of the earth and substantially parallel to a geometric line intersecting the medical professional 108 and the patient 110. This line is also substantially parallel to the short dimension of the operating table 112. The X axis is perpendicular to the Y axis and is substantially parallel to the long dimension of the operating table 112. The Z axis is parallel to the direction of gravity and perpendicular to both the X and Y axes.

The fluoroscope arm 106 can be rotated about the Y axis as indicated by directional arrow GG. This rotation causes the fluoroscope emitter 102, fluoroscope receiver 104 and fluoro axis 124 to turn clockwise or counter clockwise from the viewing perspective of the medical professional 108 as shown in FIGS. 1A–1B.

The fluoroscope arm 106 also can be rotated about the X axis in a clockwise or counter clockwise direction as indicated by directional arrow HH. When moving the fluoroscope arm 106 about the X axis in the clockwise direction, the fluoroscope emitter 102 moves closer to the medical professional 108 while the fluoroscope receiver 104 moves farther away from the medical professional 108. When moving the fluoroscope arm 106 about the X axis in the counter clockwise direction, the fluoroscope emitter 102 moves farther away from the medical professional 108 while the fluoroscope receiver 104 moves closer to the medical professional 108.

Now referring to FIG. 1B, the viewing perspective is directed downward and parallel to the Z axis and perpendicular to the X-Y horizontal plane of this arrangement as indicated by the X, Y, and Z axes 132. The rotation of the fluoroscope arm 106 about the X axis is shown by directional arrows HH. The long dimension or length of the operating table 112 is parallel to the X axis. The head of the patient 110 lies toward the positive direction of the X axis while the feet of the patient 110 lie toward the negative direction of the X axis. An illustrative top view of an embodiment of the needle guiding device 126 also is shown.

Now referring to FIGS. 2A–2D and 3A–3D, the needle guiding device 126 includes a guide platform 230 having a top surface and a bottom surface. The guide platform 230 has an opening 242 extending through it, and it is attached to a base plate 220. The guide platform 230 and the base plate 220 typically are constructed from material(s) that is (are) visually transparent and not substantially radiopaque. Such construction allows the outer skin surface of the patient 110 to be seen below the needle guiding device 126 when positioned on the outer skin surface of the patient 110.

The guide platform 230 can be attached with a friction fit between it and the base plate 220. The guide platform 230 is rotatable about a rotation axis 228 in a clockwise or counter clockwise direction as indicated by directional arrow CC (best seen in FIGS. 2B and 2C), relative to the position of the base plate 220. In this embodiment, the rotation axis 228 is substantially perpendicular to the top surface of base plate 220 and to the top surface of the guide platform 230. The guide platform 230 typically is detachable from the base plate 220 but need not be detachable. Upon removing the guide platform 230, the top surface of the base plate 220 is revealed (best shown in FIGS. 2B and 2D).

The base plate 220 acts, in part, as a foundation for the guide platform 230. The base plate 220 has a bottom surface and a top surface. The top surface abuts the bottom surface of the guide platform 230. The base plate 220 has an opening 202 that extends through the center of both the top and bottom surfaces of the base plate 220. The rotation axis 228 extends through the opening 202 at a center point 280 (best seen in FIG. 2D). The bottom surface of the guide platform 230 is disposed adjacent to the opening 202.

A pivot cylinder 234 is situated above the base plate 220 and within the guide platform 230. The pivot cylinder 234 has a curved outer surface. In this embodiment, slot openings 244, 246 (best seen in FIG. 2C) (collectively referenced as opening(s) 242) in the top surface of the guide platform 230 partially expose the curved outer surface of the pivot cylinder 234. In other embodiments, the curved outer surface is partially or fully exposed through the one or more openings in the top surface of the guide platform.

An aperture 207 is located along the perimeter of the base plate 220 and adjacent to the outer stabilizer rim 208. The medical professional 108 can insert his/her finger to touch the patient's outer skin. This feature allows the medical professional 108 to verify the location of the needle guiding device 126 with respect to a body structure. For example, the medical professional 108 can verify the location of a patient's rib. A gap 206 located between the base plate 220 and the outer stabilizer rim 208 also allows the medical professional 108 finger access while positioning the needle guiding device 126.

The pivot cylinder 234 also has two flat and circular outer surfaces 308a, 308b (best seen in FIGS. 3A and 3C) that are substantially perpendicular to the top surface of the guide platform 230 in this embodiment. Each flat and circular outer surface 308a, 308b has a center point 310a, 310b (respectively). The pivot cylinder 234 extends along a pivot axis 222 through the center points 310a, 310b. The pivot axis 222 is substantially perpendicular to the rotation axis 228.

Figure 2B:
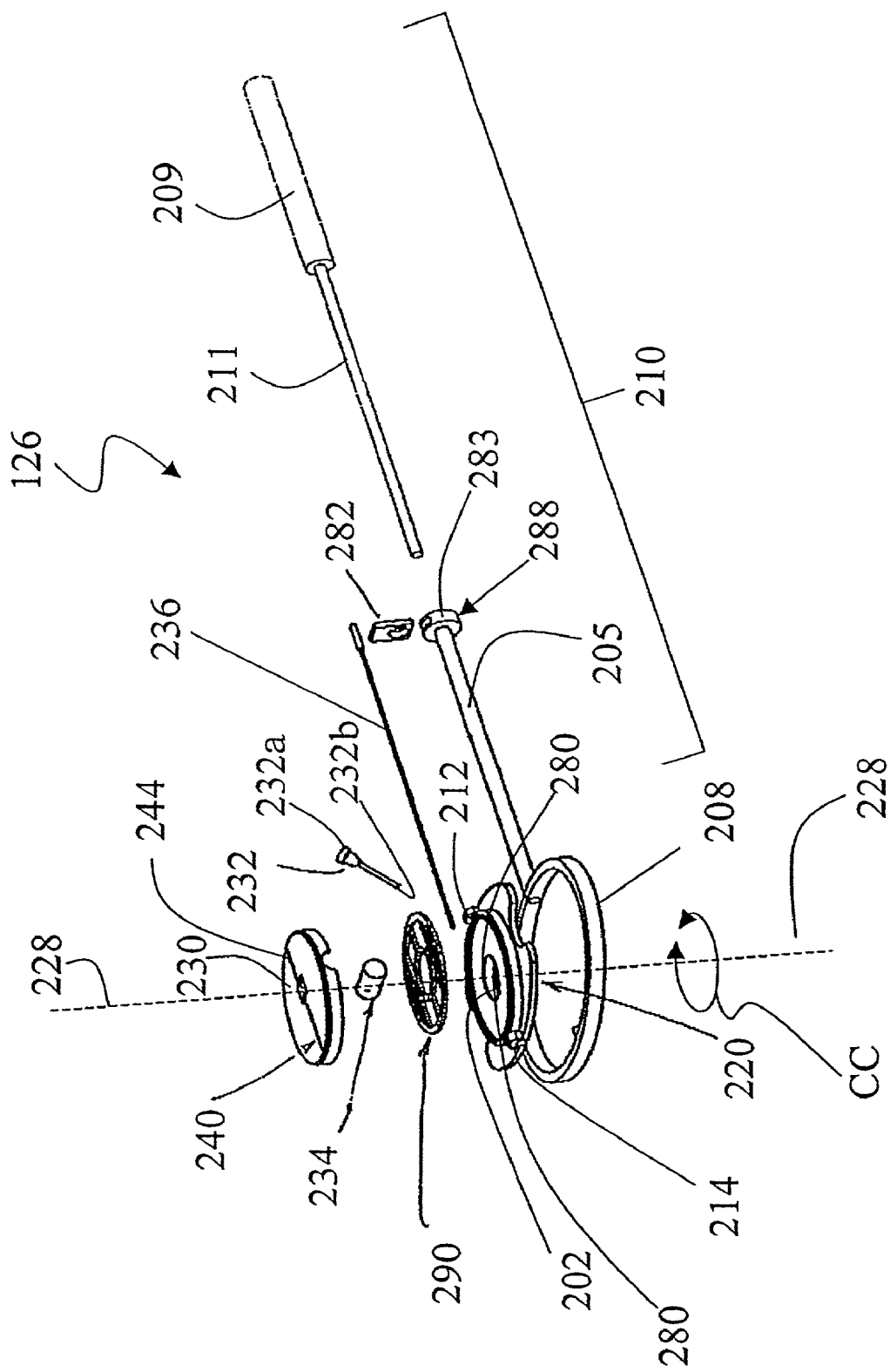
FIG. 2B is an exploded view of the embodiment of the needle guiding device shown in FIG. 2A.
Figure 2C:
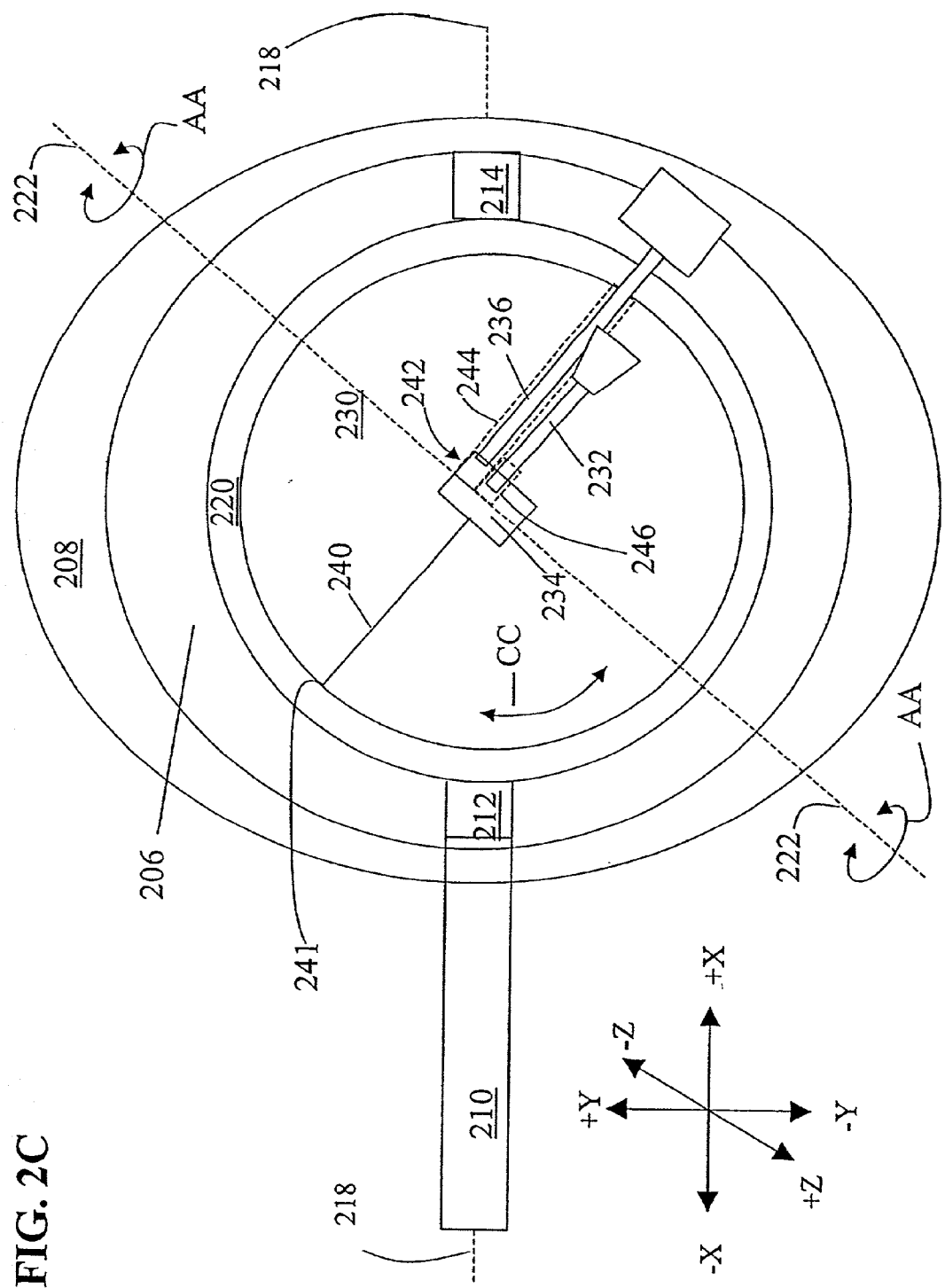
FIG. 2C is a schematic top view of the embodiment of the needle guiding device shown in FIG. 2A showing a pivot axis and a guide platform with slots located along its top surface.
Figure 2D:
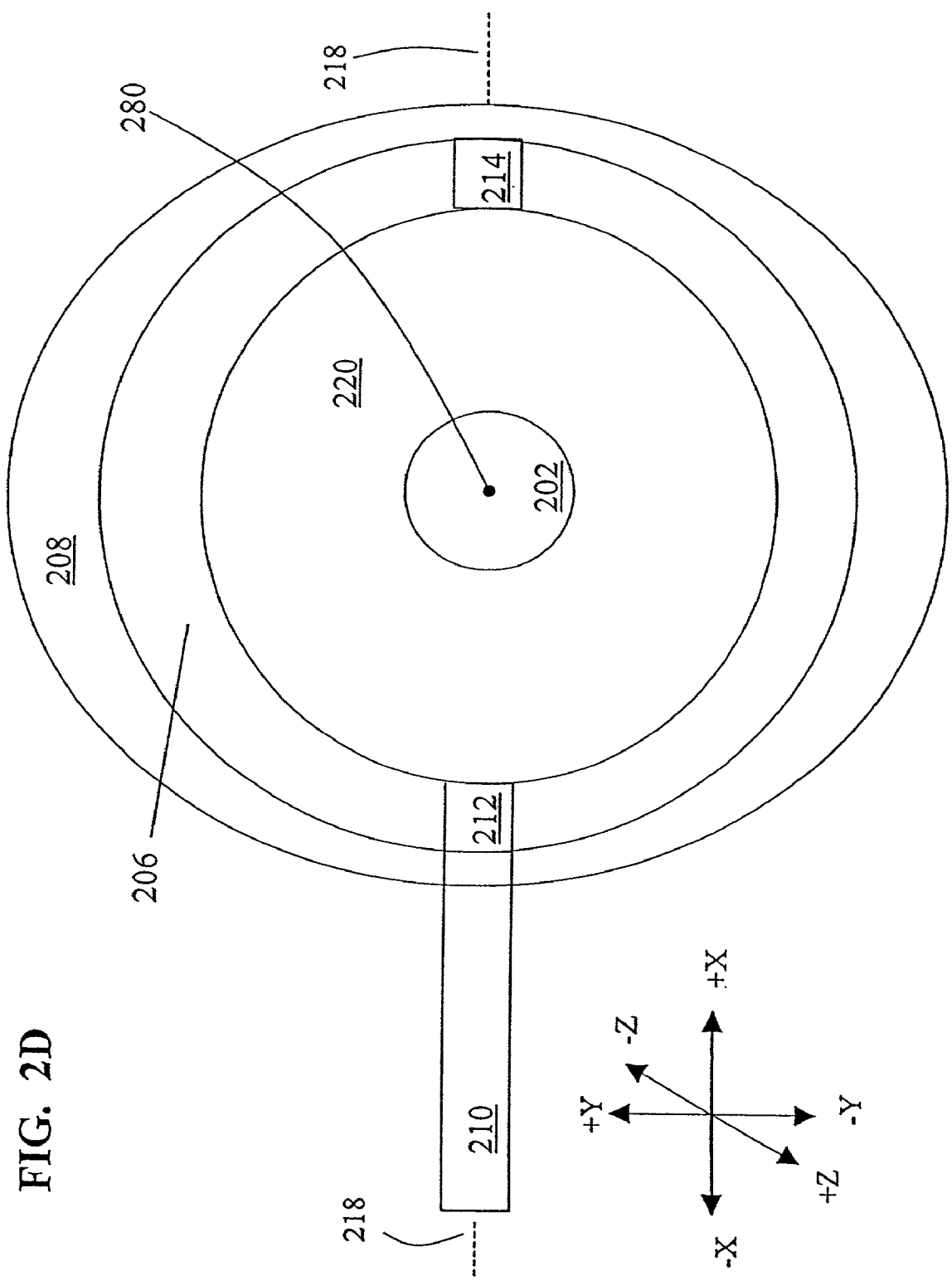
FIG. 2D is a schematic top view of the embodiment of the needle guiding device shown in FIG. 2A showing a top surface and a center point of a base plate.

The pivot cylinder 234 is rotatable about the pivot axis 222 as indicated by arrow AA (best seen in FIG. 2C). A guide shaft 232 and a guide rod 236 are each connected to the pivot cylinder 234 at their distal ends. In certain embodiments, the guide shaft 232 and/or the guide rod 236 can be at least partially disposed within a bore of the pivot cylinder 234. The guide shaft 232 fits into a bore through the pivot cylinder 234. A slot opening 244 forms an opening in the top surface of the guide platform 230 to accommodate movement of the guide rod 236. A second slot 246 forms a slot opening in the top surface of the guide platform 230 to accommodate movement of the guide shaft 232.

The rotational movement of the pivot cylinder 234 is transferred to both the guide shaft 232 and the guide rod 236 such that when the pivot cylinder 234 rotates about the pivot axis 222, both the guide shaft 232 and the guide rod 236 rotate about the pivot axis 222. The guide shaft 232 and the guide rod 236 can be positioned at many angles relative to the top surface of the base plate 220 and/or the top surface of the guide platform 230. Additionally, when the guide platform 230 rotates about the rotation axis 228, the pivot cylinder 234, along with the guide shaft 232 and guide rod 236, also rotates about the rotation axis 228. Accordingly, the pivot axis 222 can be rotated about the rotation axis 228.

In use, a medical professional can move the guide rod 236 about the pivot axis 222 to transfer rotational movement to the guide shaft 232 via the pivot cylinder 234. Movement of the guide rod 236 enables the medical professional 108 to adjust the position of the guide shaft 232 without directly handling the guide shaft 232. The guide shaft 232 typically resides within the fluoro beam 122 when the needle guiding device 126 is in use. This feature aids the medical professional in avoiding health risks associated with exposure to the x-ray radiation of the fluoro beam 122 when using the needle guiding device 126. Additionally, the guide rod 236 can be used as a handle to adjust the rotational position of the guide platform 230 about the rotation axis 228.

Figure 3A:
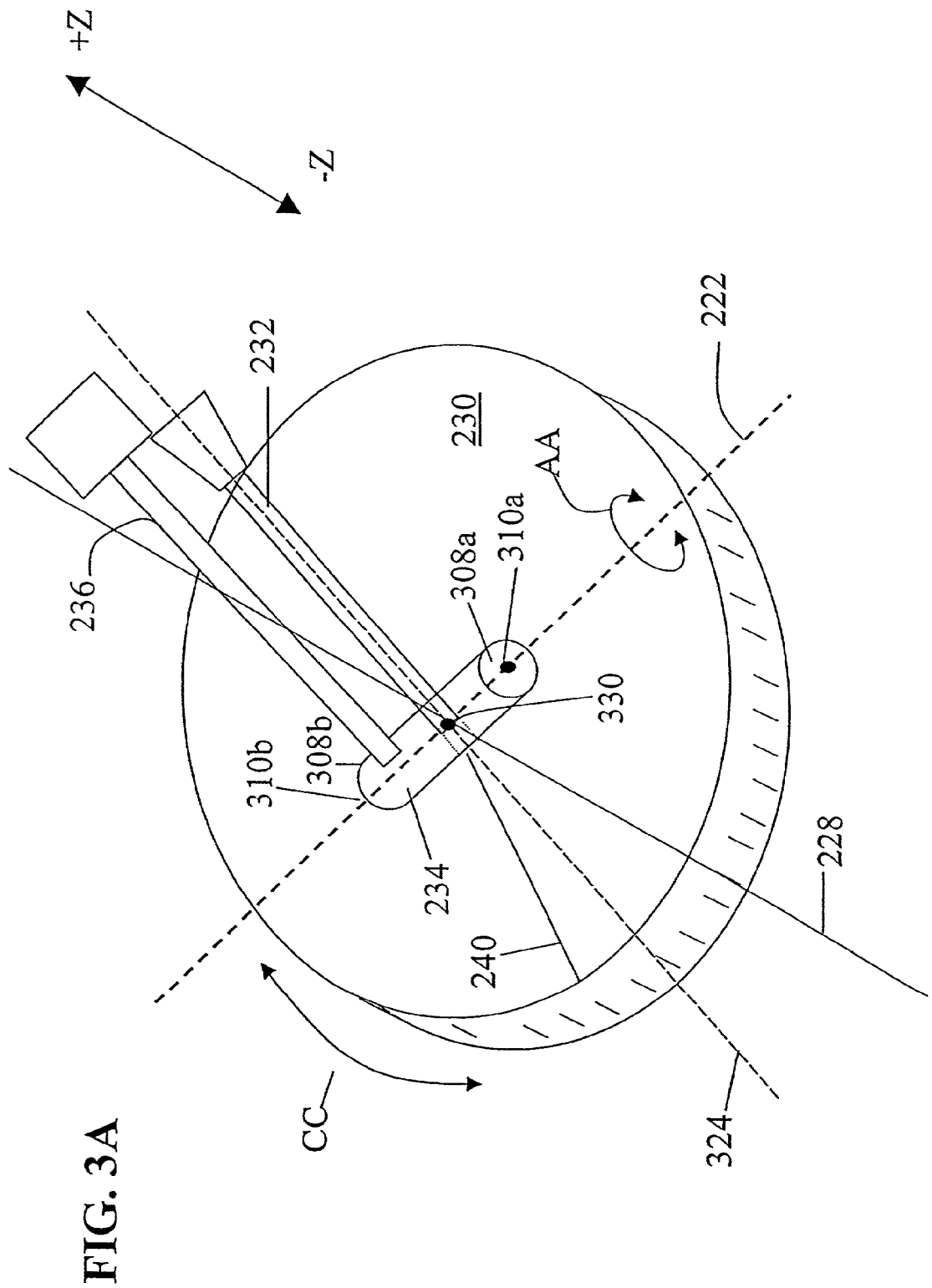
FIG. 3A is a schematic top view of a guide platform of the embodiment of the needle guiding device shown in FIG. 2A.
Figure 3B:
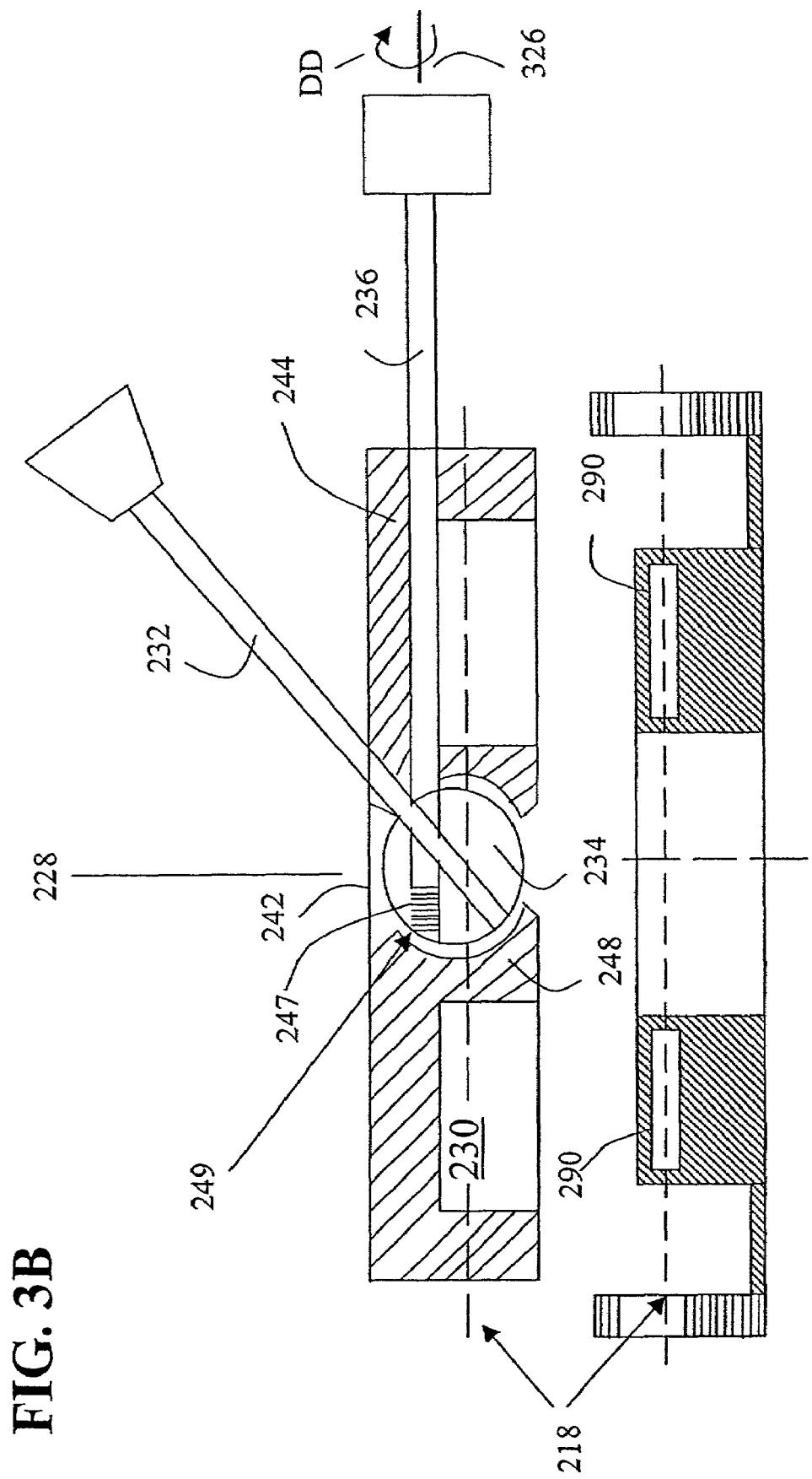
FIG. 3B is a schematic side view of a guide shaft locking mechanism of the embodiment of the needle guiding device shown in FIG. 2A.
Figure 3C:
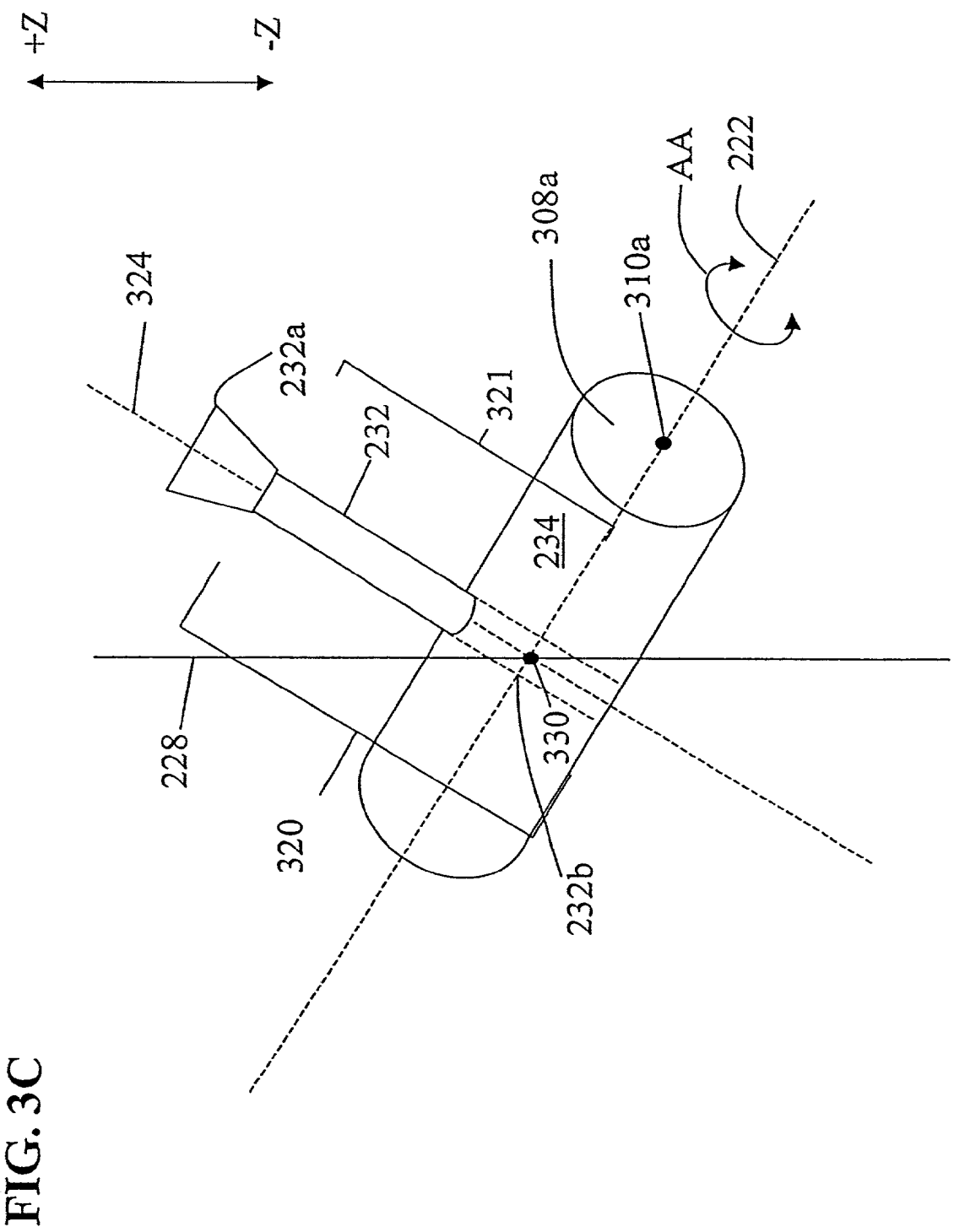
FIG. 3C is a schematic view of a pivot cylinder portion and a guide shaft of the embodiment of the needle guiding device shown in FIG. 2A.
Figure 3D:
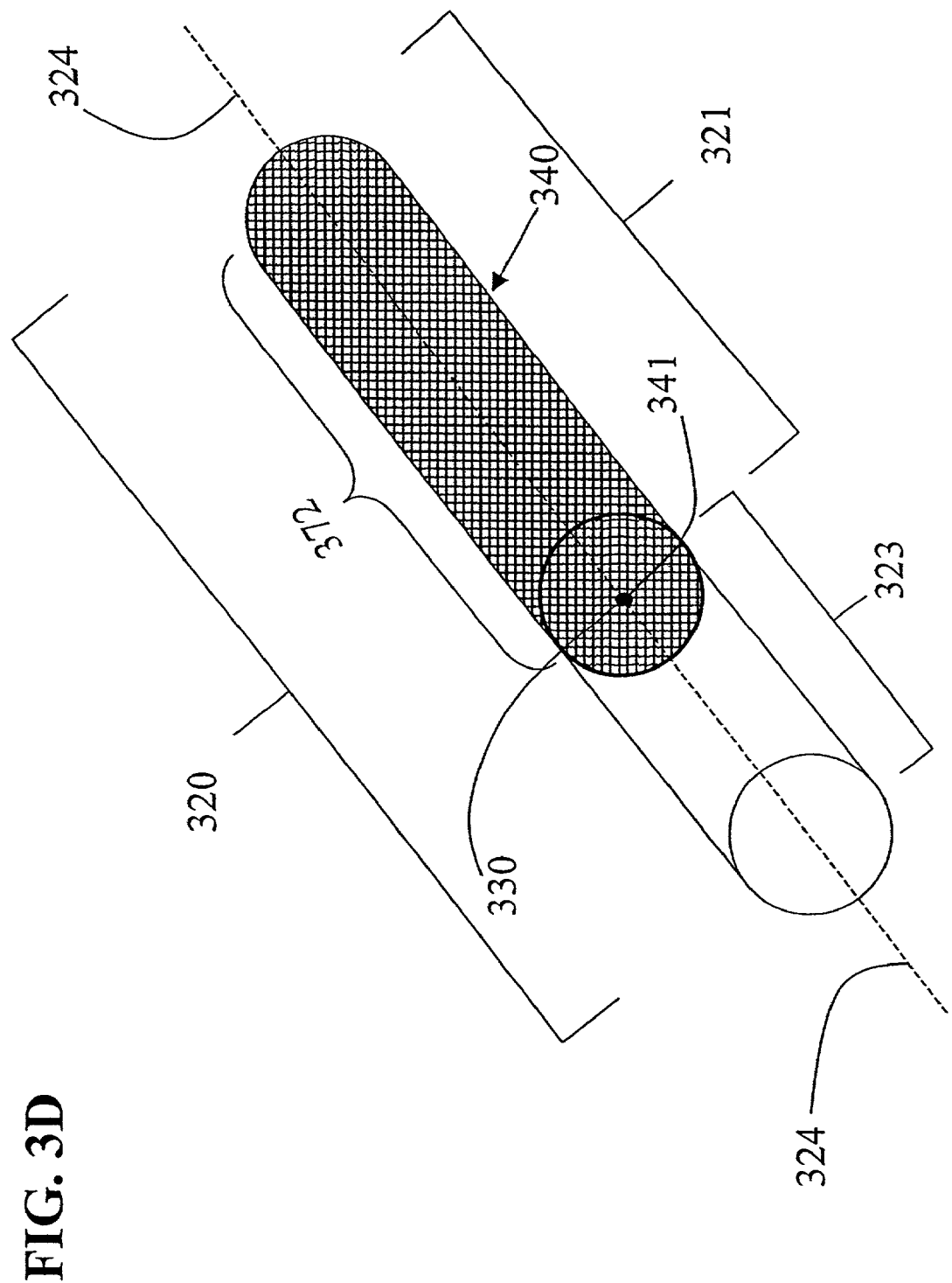
FIG. 3D is a schematic view of a guide platform passageway and a common point of the embodiment shown in FIG. 2A.

The guide rod 236 has a mechanism that locks the position of the pivot cylinder 234 about the pivot axis 222 (best seen in FIG. 3B). The distal end of the guide rod 236 is threaded 247 to engage with an at least partially threaded bore extending through the pivot cylinder 234. When the guide rod 236 is rotated about its axis 326 as indicated by arrow DD, it is drawn into and through the bore of the pivot cylinder 234. Upon being drawn entirely through the bore of the pivot cylinder 234, the distal end of the guide rod 236 makes contact with a surface 248 inside the guide platform 230. The surface 248 is complementary to the outer curved surface of the pivot cylinder 234. This contact creates a pressing force on the surface 248 inside the guide platform 230 that prevents the rotational movement of the guide rod 236, the pivot cylinder 234 and the guide shaft 232 about the pivot axis 222.

The guide shaft 232 has a longitudinal dimension and extends in the direction of its longitudinal dimension along a guide shaft axis 324. The guide shaft 232 defines an internal passageway 321 (best seen in FIG. 3C) that is capable of containing a probe such as a needle. The internal passageway 321 of the guide shaft 232 forms a portion of a guide platform passageway 320 extending through the guide shaft 232, through the pivot cylinder 234, and through the guide platform 230. The guide platform passageway 320 abuts the opening 202 in the base plate 220 and provides a passage through which a probe or needle can travel towards a target. The direction of this passage 320 is adjustable about the rotation axis 228 and the pivot axis 222 for aiming the needle guiding apparatus 126 such that a needle is directed towards its target.

The guide shaft 232 extends from a first end 232a to a second end 232b of the guide shaft 232. The guide shaft axis 324, the rotation axis 228, and the pivot axis 222 intersect at a common point 330. The common point 330 is located inside the guide platform passageway 320. The location of the common point 330 is fixed relative to other stationary portions of the needle guiding device 126, such as the handle 210. With respect to any other stationary portions of the needle guiding device 126, the location of the common point 330 remains fixed independent of the rotational position of the guide platform 230, the pivot cylinder 234 and the guide shaft 232.

The radiopaque material 340 (best seen in FIG. 3D) is located in close proximity to the location of the common point 330. The radiopaque material 340 provides an indication of the location of the guide shaft 232 and the location of the common point 330 when the needle guiding device 126 is viewed on a fluoroscope display 116. The radiopaque material 340 also serves as an accurate indication of the location of the center point 280 and of the needle insertion point along the outer surface of the patient 110.

The guide shaft 232 is made from the radiopaque material 340 which is located between the first end 232a of the guide shaft 232 and a locus 341 along the guide shaft 232. In other embodiments, the radiopaque material lines the inside surface of the guide shaft 232 or covers the guide shaft 232. The locus 341 is located normal to the guide shaft axis 324 at the common point 330. The radiopaque material 340 extends along at least a portion 372 of the guide shaft 232 to the locus 341 and, in this embodiment, the locus 341 and the common point 330 is at the end 232b of the guide shaft 232.

The locus 341 is located immediately adjacent to a material 323 being less radiopaque than the radiopaque material 340. In this embodiment, starting at the locus 341 the radiopaque material 340 entirely surrounds the common point 330. As the radiopaque material 340 surrounds the common point 330, each point of the radiopaque material 340 is located normal to the guide shaft axis 324 at the common point 330 and is immediately adjacent to a less radiopaque material.

In alternative embodiments, the bore through the pivot can be made from and/or lined with a radiopaque material that extends to the common point as described above. In this case, the locus which is normal to the guide shaft axis also is at the common point. When the common point is located inside the bore, the locus is accordingly located inside or on the inner surface of the bore. In certain embodiments only a portion of the guide shaft and/or the bore are more radiopaque than the material located adjacent to the locus at the common point. Additionally, the radiopaque material at the locus need not be uniformly disposed normal to the guide shaft axis at the common point such that a locus can be a single point of radiopaque material located normal to the guide shaft at the common point and which is located immediately adjacent to a less radiopaque material.

When inserted through the guide shaft 232, a probe or needle travels generally through the common point 330 and towards a target. The location of the center point 280 of the base plate 220 is in close proximity to the location of the needle insertion point along the outer surface of the patient 110. In the embodiment shown, the common point and the center point are in the same location. In other embodiments, the common point 330 and the center point 280 can be in the same location or different locations. In certain embodiments, including this embodiment, the common point 330 is located at the second end 232b of the guide shaft 232.

The direction of the guide shaft axis 324 defines a needle insertion trajectory. The radiopaque material 340 of the guide shaft 232 projects a visible profile when viewed from the fluoroscope display 116. When the guide shaft axis 324 is aligned along the fluoro axis 124, the radiopaque material 340 projects the smallest profile image on the fluoroscope display 116.

In this embodiment, the smallest profile image of the radiopaque material 340 appears as a circle. The circle has a diameter representing the diameter of the guide shaft 232. If the radiopaque material does not extend around the common point 330, the smallest profile image of the radiopaque material 340 appears as a portion of a circle on the fluoroscope display 116. When the guide shaft axis 324 is not aligned along the fluoro axis 124, the radiopaque material 340 projects a larger profile image on the fluoroscope display 116. In this embodiment, the larger profile image of the radiopaque material 340 appears as an oblong shape which has a thickness which represents the diameter of the guide shaft 232. Other embodiments have one or more portions of radiopaque material located along the guide shaft and/or the bore through the pivot cylinder. For these embodiments, the larger profile of the radiopaque material can appear as a broken oblong shape.

Because the radiopaque material 340 extends to, but not beyond, the locus 341, the radiopaque material 341 forms a profile image when viewed on the fluoroscope display 116. This visible profile image appears as an edge. This edge is seen because the radiopaque material 340 is located immediately adjacent to other material that is less radiopaque. The edge also indicates the location of the common point 330 along the guide shaft 232.

In embodiments where the radiopaque material does not entirely surround the common point at points normal to the guide shaft axis at the common point, the image of the edge may not be as distinguishable and may be less accurate as compared to when the radiopaque material does surround the common point at points normal to the guide shaft axis at the common point. A similar situation may apply to embodiments where the radiopaque material extends beyond points normal to the guide shaft axis at the common point.

Figure 4A:
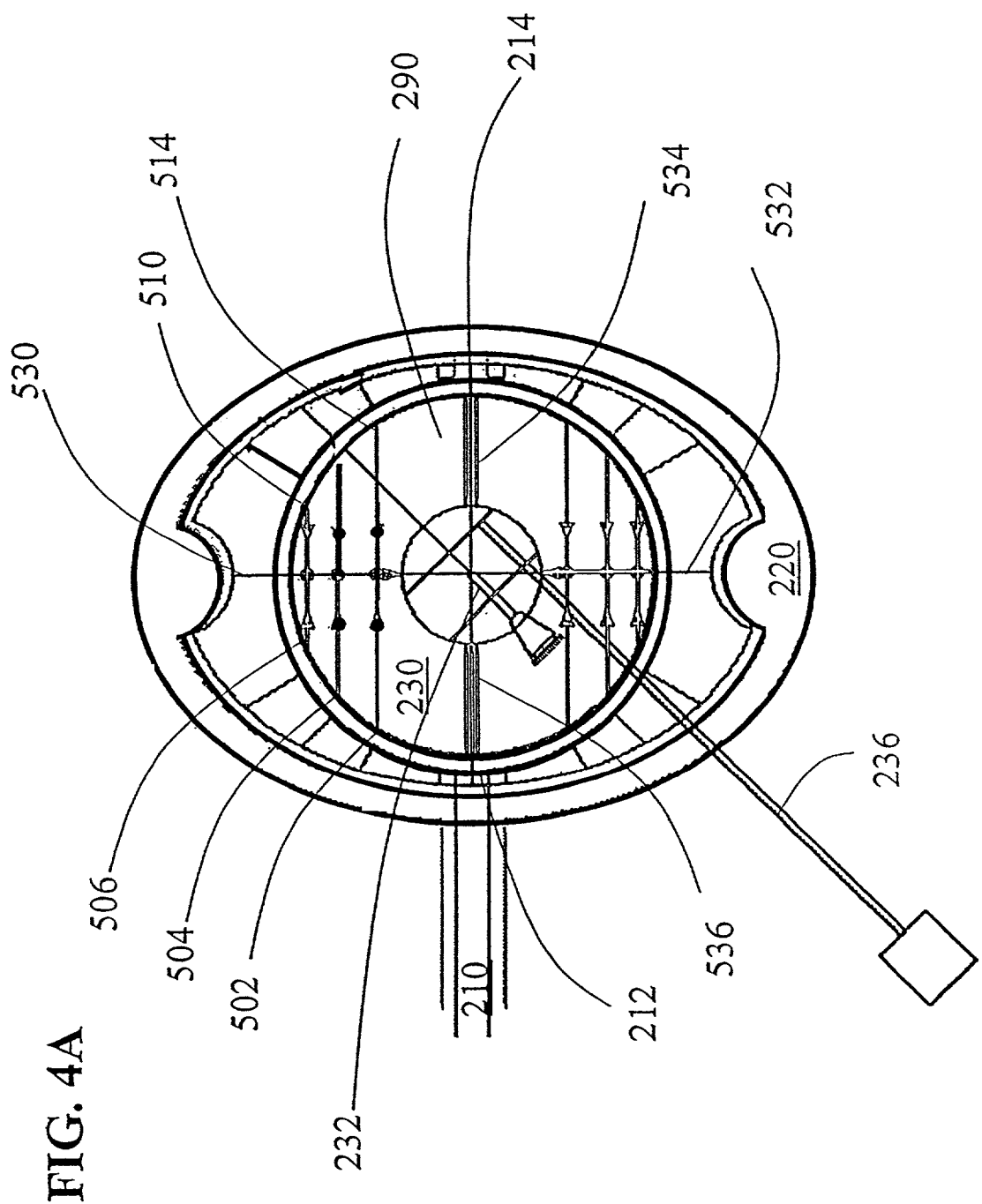
FIG. 4A is a schematic top view of an imaging grid portion of the embodiment shown in FIG. 2A.

An imaging grid 290 (best seen in FIGS. 4A–4C) is a collection of one or more markings located along the top surface of the base plate 220. These markings aid the medical professional 108 to use the needle guiding device 126 when aiming a probe or needle 442 towards a target 410. The imaging grid 290 includes at least one radiopaque point and is disposed about the rotation axis 228. The imaging grid 290 will be discussed in more detail when referring to FIGS. 4A–6.

An aiming line 240 (best seen in FIGS. 2A–2C) is a line shaped marking that extends from the center to the outer perimeter of the top surface of the guide platform 230. The aiming line 240 indicates the direction of needle insertion from the guide shaft 232. The aiming line 240 is constructed from material that is both radiopaque and visually distinguishable via ordinary eyesight. The distal end point 241 of the aiming line 240 (best seen in FIG. 2C) can be used as a point of reference for aligning a target and a fluoro axis 124. The aiming line 240 is directed by rotating the guide platform 230 about the rotation axis 228 with respect to the position of the base plate 220 and the imaging grid 290.

The needle guiding apparatus 126 also includes a handle 210 which extends along a handle axis 218. Typically, the handle axis 218 is substantially perpendicular to the rotation axis 228. The handle axis 218 intersects the common point 330. The handle axis 218 is not required to intersect the common point 330. In other embodiments, the handle axis does not intersect the common point 330. The handle 210 includes a sleeve 205 which extends over a shaft 211 (best seen in FIG. 2B). The sleeve 205 is connected to an outer stabilizer rim 208 which surrounds the base plate 220. The distal end of the shaft 211 extends through an opening in an outer stabilizer rim 208 and connects to the base plate 220 via a handle attachment 212. The base plate 220 also is attached to the outer stabilizer rim 208 via an outer stabilizer rim attachment 214 located opposite from the handle attachment 212.

Figure 2E:
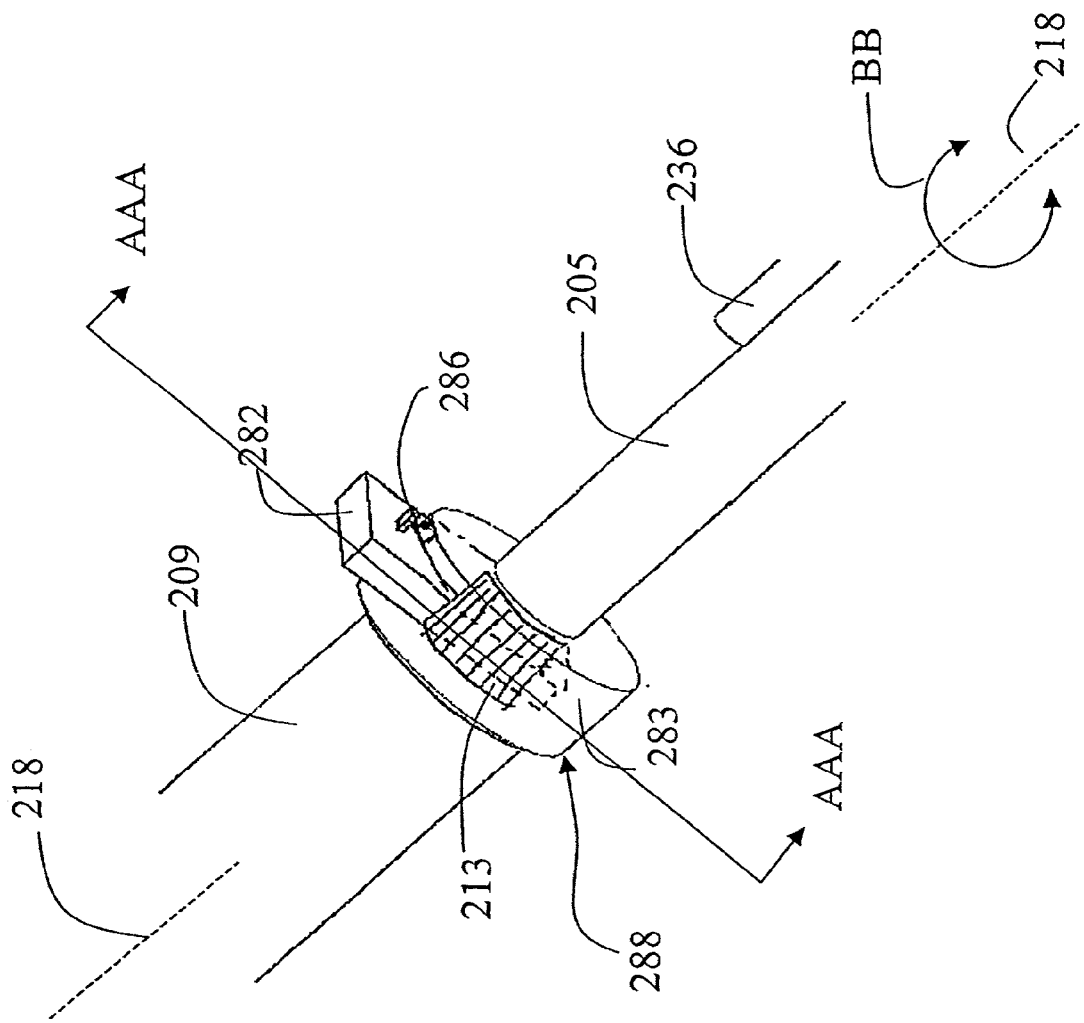
FIG. 2E is a schematic enlarged view of a sleeve locking mechanism of the embodiment of the needle guiding device shown in FIG. 2A.
Figure 2G:
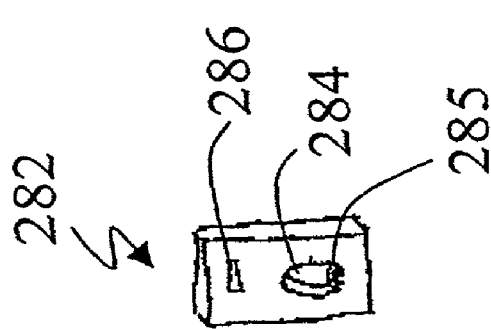
FIG. 2G is a schematic end view of a vertical plate of the sleeve locking mechanism of the embodiment of the needle guiding device shown in FIG. 2A.
Figure 2F:
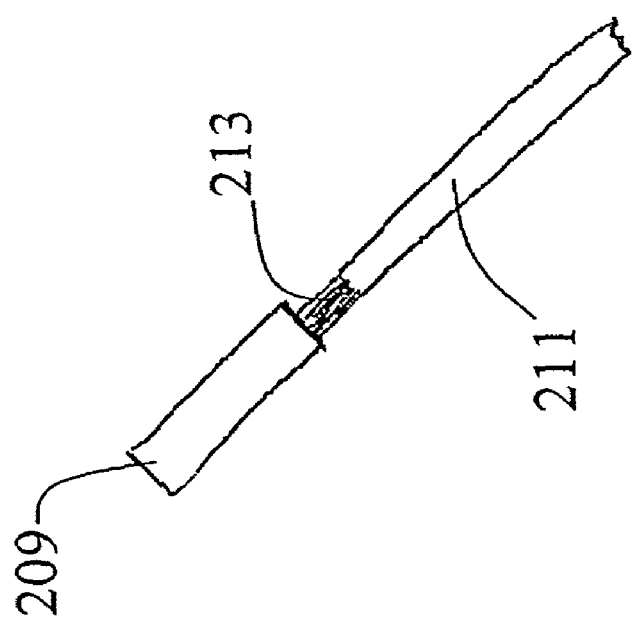
FIG. 2F is a schematic side view of a hand grip and a shaft of a handle of the embodiment of the needle guiding device shown in FIG. 2A.

Referring to FIG. 2F, the outer curved surface of the proximal end of the shaft 211 has teeth 213 forming ridges directed along the handle axis 218 that engage complementary structures located inside the distal end of the hand grip 209. Accordingly, the proximal end of the shaft is connected to a hand grip 209 for the medical professional to grasp. The handle 210 can be rotated in either direction around the handle axis 218 as indicated by directional arrow BB. The teeth 213 of the shaft 211 protrude outside of the hand grip 209 when the teeth 213 are fully engaged with the hand grip 209.

When the hand grip 209 is used to rotate the handle 210 about the handle axis 218, the base plate 220 and the guide platform 230 can rotate around the handle axis 218 independent of the position of the outer stabilizer rim 208. In certain embodiments, the shaft 211 and the sleeve 205 can be made of a flexible material, such as pliable rubber or plastic, to enable the handle 210 to bend when negotiating the contours of the outer surface of the patient 110. The sleeve 205 and the outer stabilizer rim 208, are attached to each other and are rotatable about the shaft 211. A sleeve locking mechanism 288 fixes and locks the position of the sleeve 205 and the attached outer stabilizer rim 208 to the position of the hand grip 209 and the attached shaft 211.

The sleeve locking mechanism 288 includes a circular outer shell 283 that is fixably attached to the sleeve 205 and that is rotatably attached to the hand grip 209 (best seen in FIGS. 2E–2K). The sleeve locking mechanism 288 can be placed into a locked or an unlocked state. When in the unlocked state, the sleeve locking mechanism 288, the sleeve 205 and the outer stabilizer rim 208 are together rotatable about the handle axis 218 in a manner independent of the position of the hand grip 209, the shaft 213 and the base plate 220. When in the locked state, the sleeve locking mechanism 288, the sleeve 205 and the outer stabilizer rim 208 are not rotatable about the handle axis 218 in a manner independent of the position of the hand grip 209, the shaft 213 and the base plate 220.

The sleeve locking mechanism 288 includes a vertical plate 282 located inside a slot 289 that is located inside a circular outer shell 283. The vertical plate 282 slides up and down within the slot 289 inside the outer shell 283 in a substantially perpendicular direction relative to the shaft axis 218. The shaft 211 is attached to the distal end of the hand grip 209 while being disposed within the circular outer shell 283 that is fixably attached to the sleeve 205. The vertical plate 282 has a longitudinal dimension that is normal to the handle axis 218. The vertical plate 282 also has an oval shaped opening 284 extending through it along a direction which is parallel to the handle axis 218.

Referring to FIG. 2H, a cross sectional view of the slot 289 located inside of the circular outer shell 283 is shown generally along line AAA of FIG. 2E. The slot 289 is designed to accommodate the movement of the vertical plate 282. The sleeve 205 is fixably attached to the circular outer shell 283 at the location shown.

Referring to FIG. 2I, a cross sectional view of the vertical plate 282 located inside the slot 289 of the circular outer shell 283 is shown generally along line AAA of FIG. 2E. The vertical plate 282 has an opening 284 and teeth 285 located along the lower perimeter of the opening 284.

Figure 2K:
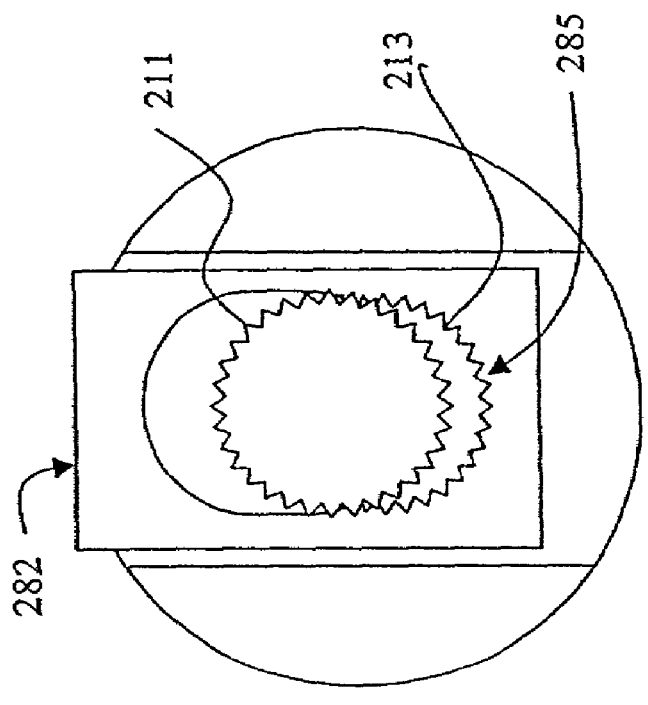
FIG. 2K is a schematic cross section taken generally along line AAA—AAA in FIG. 2E of the slot and the unengaged vertical plate of the sleeve locking mechanism of the embodiment of the needle guiding device shown in FIG. 2A.
Figure 2J:
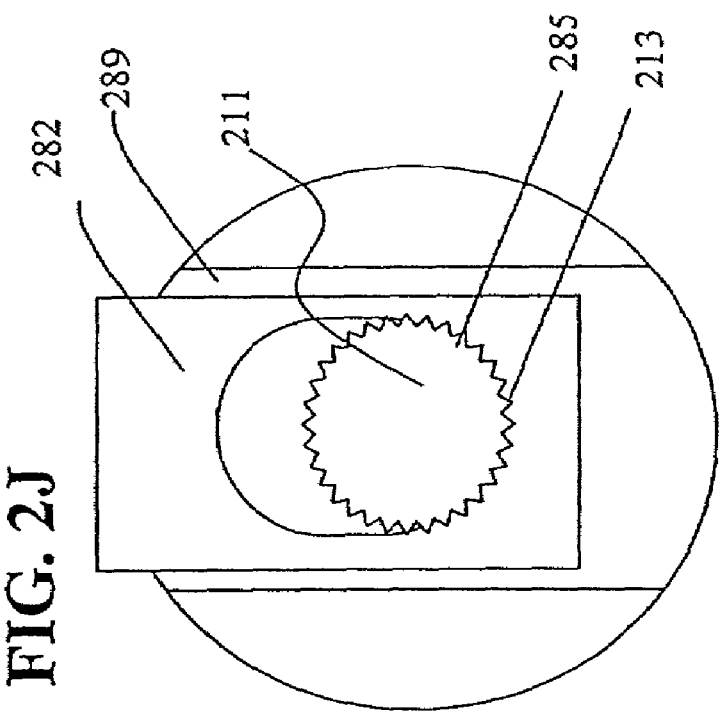
FIG. 2J is a schematic cross section taken generally along line AAA—AAA in FIG. 2E of the slot and the engaged vertical plate of the sleeve locking mechanism of the embodiment of the needle guiding device shown in FIG. 2A.

Referring to FIG. 2J, a cross sectional view of the teeth 213 of the proximal end of the shaft 211 engaging the teeth 285 located along the lower perimeter of the opening 284 of the vertical plate 282, as shown generally along line AAA of FIG. 2E. The vertical plate 282 is shown in an elevated and locked position.

Referring to FIG. 2K, a cross sectional view of the teeth 213 of the proximal end of the shaft 211 as disengaged from the teeth 285 of the lower perimeter of the opening 284 of the vertical plate 282, as shown generally along line AAA of FIG. 2E. The vertical plate 282 is shown in a non elevated and unlocked position.

The teeth 213 of the proximal end of the shaft 211 are disposed within the opening 284 of the vertical plate 282 is shown generally along line AAA of FIG. 2E. The vertical plate 282 is disposed inside the slot 289 that is located inside the circular outer shell 283.

The proximal end of the shaft 211 is disposed within the opening 284 and disposed towards the lower side of the opening 284. The lower perimeter of the opening 284 has teeth 285 directed upward. The proximal end of the shaft 211 also has teeth 213 which are situated about at least part of the circumference of the shaft 211. The vertical plate 282 can be positioned into a locked or an unlocked position and is biased to a locked position.

When in the locked state, the rotational position of the sleeve 205 and the attached outer stabilizer rim,208 about the handle axis 218 are fixed with respect to the position of the base plate 220, the hand grip 209 and the shaft 211. The vertical plate 282 is located in its most elevated position so that the teeth 285 of the vertical plate 282 engage the teeth 213 of the proximal end of the shaft 211. Engagement between the teeth 285 of the vertical plate 282 and the teeth 213 of the proximal end of the shaft 211 locks the rotational position of the shaft 211, the attached handgrip 209 and the attached base plate 220 relative to the rotational position of the sleeve 205 and the attached outer stabilizer rim 208. A cantilever spring 286 exerts an upward force upon the vertical plate 282 to hold it into its locked position.

When in the unlocked state, the sleeve 205 and the outer stabilizer rim 208 are rotatable about the handle axis 218 relative to the position of the base plate 220, the hand grip 209 and the shaft 211. In the unlocked state, the rotational position of the sleeve 205 and of the outer stabilizer rim 208 about the handle axis 218 can be adjusted relative to the rotational position of the base plate 220, the hand grip 209 and the shaft 211. To position the sleeve locking mechanism 288 into the unlocked state, a downward force (for example, by a medical professional 108 pressing on the vertical plate 282) is exerted upon the vertical plate 282 against the upward force exerted by the cantilever spring 286. The downward force is exerted until the vertical plate 282 is positioned to fully disengage the teeth 285 of the vertical plate 282 from the teeth 213 of the shaft 211. Ceasing to exert a downward force on the vertical plate 282 causes the upward force exerted on the vertical plate 282 by the cantilever spring 286 to return the vertical plate 282 to its locked position.

Figure 2L:
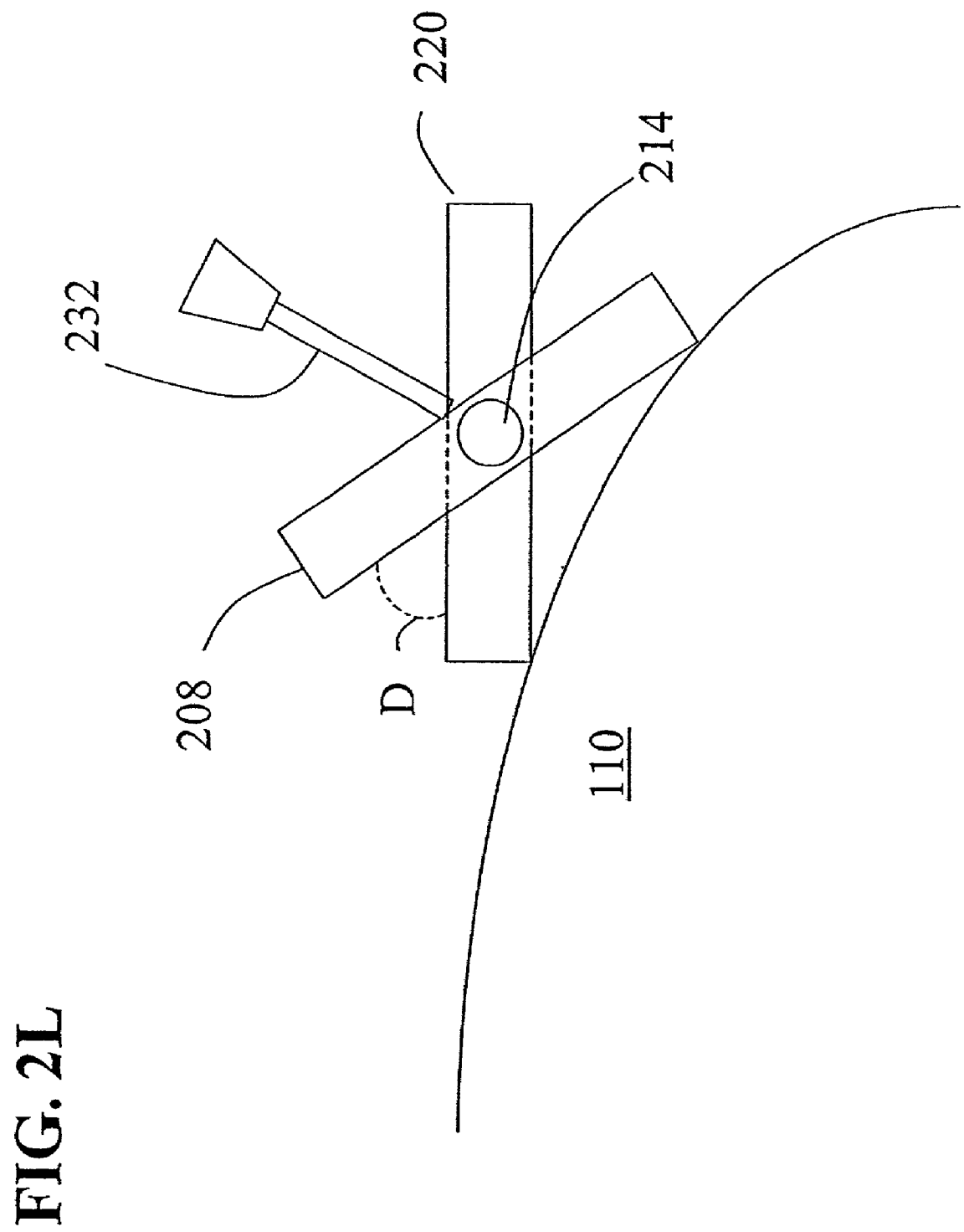
FIG. 2L is a schematic view of an outer stabilizer rim being locked into a position relative to the position of the base plate of the embodiment of the needle guiding device shown in FIG. 2A.

The outer stabilizer rim 208 provides support for the position of the base plate 220 while the needle guiding device 126 is being positioned and/or pressed against the contours of the outer surface of a patient 110 during alignment and insertion of a needle. When positioning the needle guiding device 126, the outer stabilizer rim 208 can be locked into a position relative to the position of the base plate 220 such that both the outer stabilizer rim 208 and the base plate 220 contact the patient (best seen in FIG. 2L).

For example, to account for the curvature of the patient's back, the outer stabilizer rim 208, relative to the base plate 220, can be set at an angle D. Due to the angle D between the two parts 208, 220, the needle guiding device 126 can be placed on the patient 110 such that the needle guiding device 126 makes fuller contact with the outer contours of the patient 110.

Figure 2M:
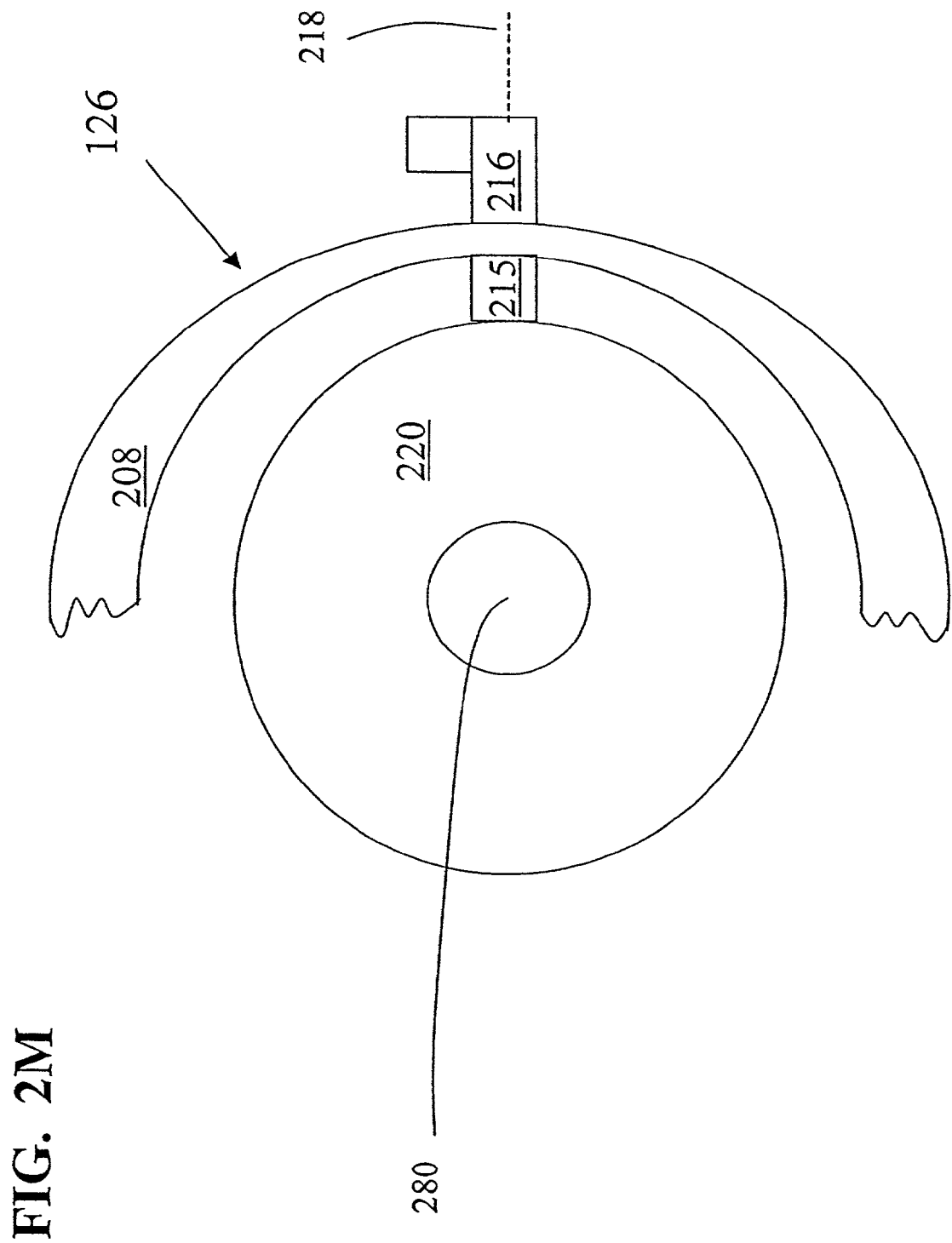
FIG. 2M is a schematic partial top view of an alternative embodiment of a sleeve locking mechanism.

An alternative embodiment of a sleeve locking mechanism shown in FIG. 2M, is constructed such that the outer stabilizer rim 208 and the attached sleeve 205 are locked via an outer stabilizer rim lock mechanism 216 that is connected to an outer stabilizer rim attachment 215. The outer stabilizer rim attachment 215 has an inner end that is substantially similar to the outer stabilizer rim attachment 214 of the preferred embodiment. The outer end of the outer stabilizer rim attachment 215 is threaded and extends through an opening in the outer stabilizer rim 208.

The outer stabilizer rim lock 216 contains a threaded cavity. The threads of the threaded cavity engage the threads of the outer end of the outer stabilizer rim attachment 215. To place the outer stabilizer rim lock 216 into a locked state, it is rotated to further engage with the outer stabilizer rim attachment 215. The further engagement of the threads moves the outer stabilizer rim lock 216 towards the outer stabilizer rim 208, creating a pressing force upon the outer stabilizer rim 208, the outer stabilizer rim attachment 215, and the base plate 220. Accordingly, the position of the outer stabilizer rim 208 and of the base plate 220 are fixed relative to each other.

Now referring to FIGS. 4A–7, the needle guiding device 126 includes an imaging grid 290 (best seen in FIGS. 2B and 4A–4C). An imaging grid 290 has markings 502, 504, 506, 508, 510, 512, 514, 516, 518, 520, 522, 524, 530, 532, 534, 536, 552, 554, 556, 558, 560, 562, 564, 566, 568 and 570 that are generally shaped in the form of points or lines that aid the medical professional 108 in aiming a probe or needle 442 towards a target 410 (best seen in FIG. 6).

Guide points 502–524, 552–70 are markings that are each shaped in the form of a point. Guide lines (for example, 530–536, 572) are markings that are each shaped in the form of a line. The guide points 502–524, 552–570 and guide lines (for example, 530–536, 572) are located along the top surface of the base plate 220 (best seen in FIGS. 4A–4C) inside the imaging grid 290. These guide points 502–524, 552–570 and guide lines are designed to be symmetric with respect to left and right handed medical professionals 108. Accordingly, either a right or left handed medical professional can use the needle guiding device 126.

The markings function as points and lines of reference with respect to the relative location of the needle guiding device 126, the fluoro axis 124 and the target 410. These markings are constructed from a substance that is radiopaque and visually distinguishable from other parts of the needle guiding device 126 when viewed from either the human eye or the fluoroscope display 116.

In this embodiment, the imaging grid 290 surrounds the center point 280 of the base plate 220. Any guide point 502–524, 552–570 can be selected by the medical practitioner 108 as a target point. A target locating fluoro axis is a fluoro axis 124 that is positioned to intersect a target. The target point is a guide point that indicates a location on the needle guiding device where a target locating fluoro axis intersects the needle guiding device 126. The guide lines (for example, 530–536, 572) intersect one or more guide points 502–524, 552–570 or intersect one or more guide points 502–524, 552–570 and extrapolate to intersect the center point 280. For example, a guide line 530 intersects a guide point 520 and extrapolates to intersect the center point 280.

The crosshairs of the imaging grid 290 are guide lines 530–536 that extrapolate to intersect the center point 280 and that are directed in parallel with either the X or Y axes of the needle guiding device 126. For example, guide line 530 and guide line 532 are aligned with the Y axis of the needle guiding device 126 and define a Y axis crosshair. Guide line 534 and guide line 536 define an X axis crosshair.

In use, the medical professional can optionally position the needle guiding device 126 such that the guide lines (for example, 530–536, 572) and crosshairs 530–536 are directed parallel to at least one of the directions of movement of the fluoro axis 124. A guide line (for example, 530–536, 572) or a crosshair 530–536 can be optionally selected by the medical practitioner 108 as a path of fluoro axis movement during the needle aiming and insertion procedure.

The guide lines (for example, 530–536, 572) can indicate to the medical practitioner 108 the direction in which to move the fluoro axis 122 in order to intersect point locations on the imaging grid 290. These point locations can include the guide points 502–524, 552–570 or the center point 280. In the preferred embodiment, guide lines (for example, 530, 572) intersect at 90 degree angles, which is consistent with a fluoroscope providing two-planes of fluoro axis movement. However, guide lines need not intersect at a 90 degree angle. In other embodiments, individual guide lines can intersect a guide point and issue to the center point or intersect other guide lines at angles other than 90 degree angles.

Figure 6:
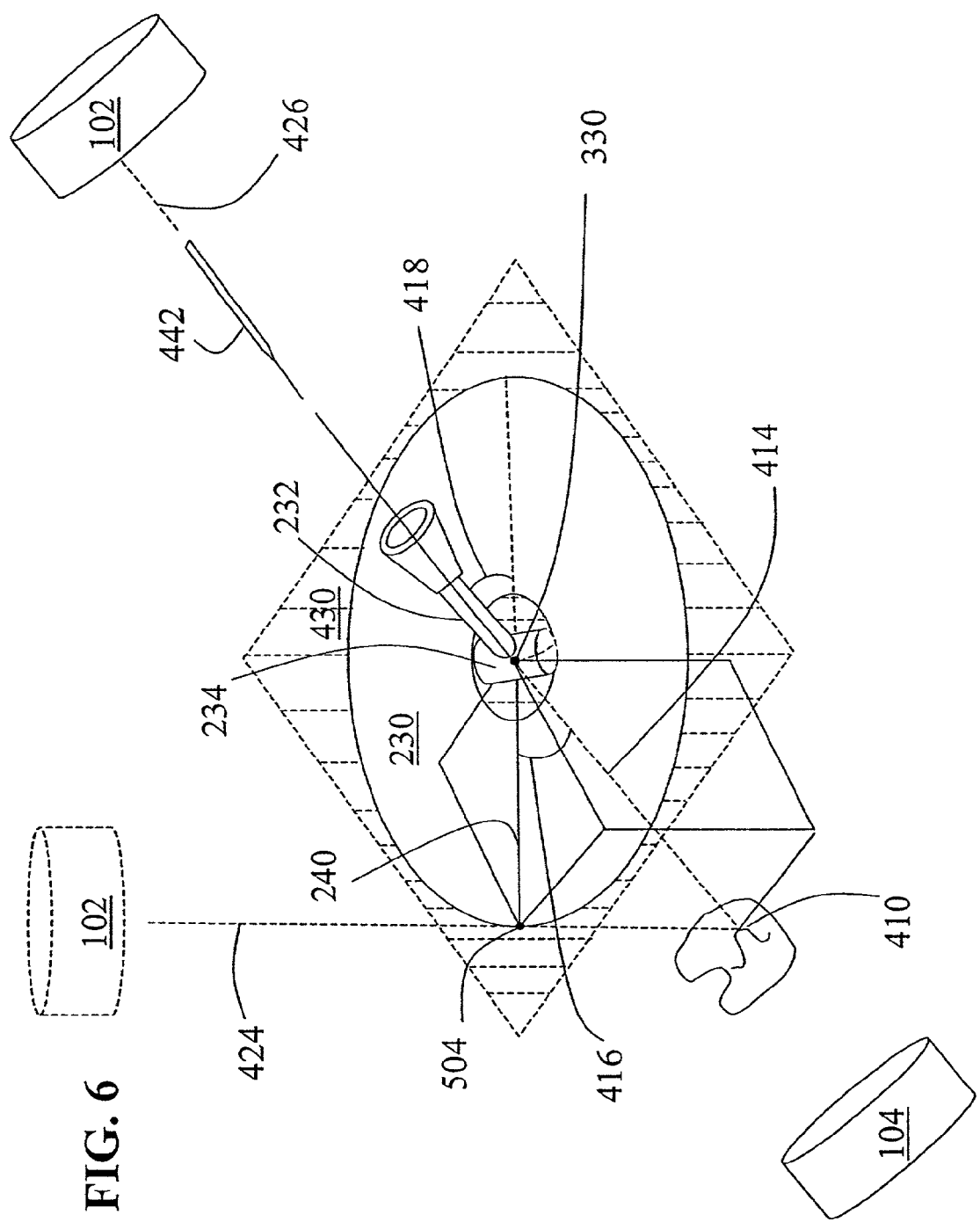
FIG. 6 is a schematic perspective view of the embodiment of the needle guiding device shown in FIG. 2A depicting the relative positioning of a reference plane, needle guide shaft, a needle insertion trajectory and a target.

The location and position of the imaging grid 290, located along the top surface of the base plate 220, defines the location and position of the reference plane 430 (best seen in FIG. 6). When the guide platform 230 is attached to the base plate 220, the center point 280 and the common point 330 have the same location. Accordingly, the reference plane 430 defined by the imaging grid 290 constitutes one plane that intersects the location of the center point 280 and the common point 330. The pivot axis 222 lies along the reference plane 430 and intersects the center point 280 and the common point 330.

In certain embodiments, the center point and the common point have separate locations that are in close proximity to each other. In these certain embodiments, the imaging grid defines a plane that intersects the center point while the reference plane intersects the common point and is parallel with the imaging grid. The imaging grid can closely approximate the location and orientation of the reference plane. Like the preferred embodiment, the pivot axis lies along the reference plane and intersects the common point. The distance between the reference plane and imaging grid is equal to the distance between the common point and the center point.

Figure 4C:
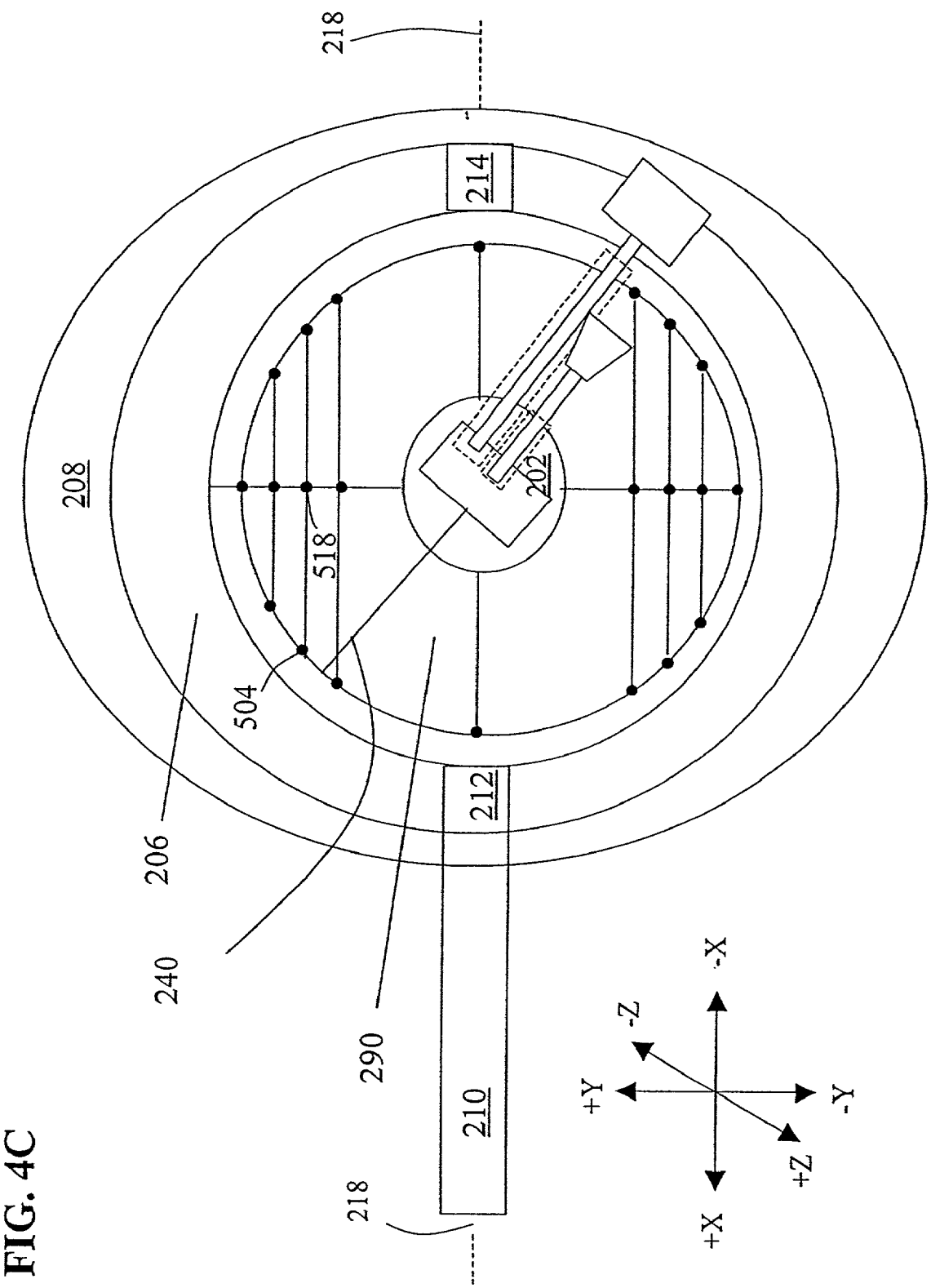
FIG. 4C is a schematic top view of the embodiment of the needle guiding device shown in FIG. 2A exposing the imaging grid located below a translucent guide platform.

The guide platform 230 is constructed from translucent material such as translucent plastic or rubber (best seen in FIG. 4C). The translucent material allows both ordinary visible light and x-ray energy of the fluoro beam 122 to pass through it without any significant attenuation. Accordingly, the imaging grid 290 which is located below the guide platform 230, is visible from a viewing perspective above the guide platform 230 via the ordinary eyesight or via the fluoroscope display 116. Other parts of the device that are not desired to appear on the fluoroscope also can be constructed of, for example, but without limitation, plastic or rubber that are not substantially radiopaque. Parts of the device that are desired to be radiopaque can be made of, for example, but without limitation, a metal.

Referring to FIG. 6, a needle insertion trajectory 414 is a path through three dimensional space that is aligned with the guide shaft axis 324 and that intersects the common point 330 and a target 410. The needle insertion trajectory 414 is defined by a directional component projected along the reference plane 430 and by a depth angle 416 relative to the reference plane 430. The angle of intersection between the guide shaft axis 324 and the reference plane 430 defines the depth angle 416.

The depth angle 416 extends below the reference plane 430 and is defined by the angle of intersection between the guide shaft axis 324 and the bottom surface of the reference plane 430. The pivot angle 418 extends above the reference plane 430 and is an angle defined by the angle of intersection between the guide shaft axis 324 and the top surface of the reference plane 430. The size of the depth angle 416 and the pivot angle 418 are proportional to the vertical pitch of the needle insertion trajectory 414. The size of the depth angle 416 and the pivot angle 418 are equal for a particular needle insertion trajectory.

Figure 5:
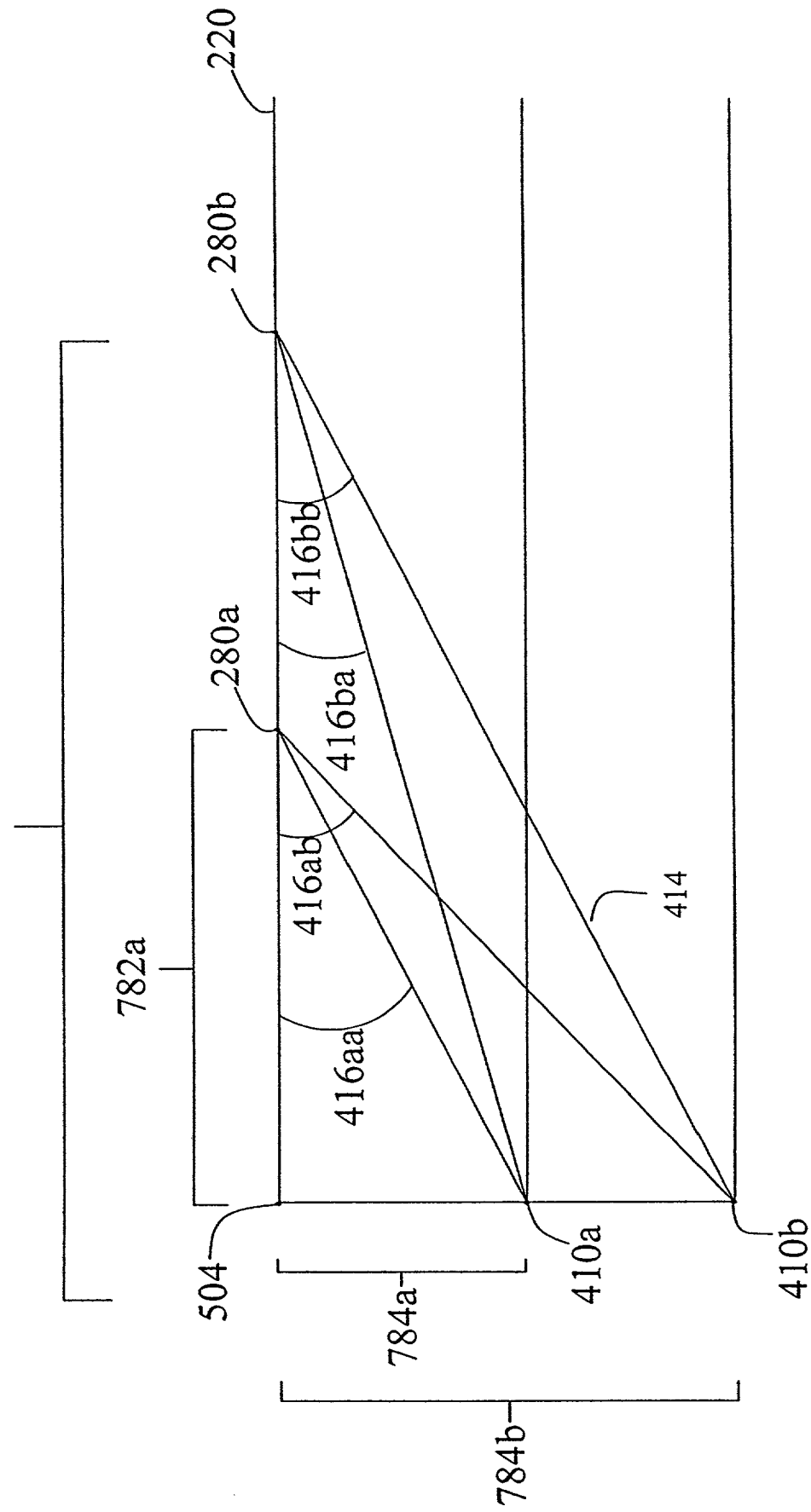
FIG. 5 is a schematic top view of the relative positioning of the top and bottom portions of the embodiment of the needle guiding device shown in FIG. 2A with respect to several calyxes of a right kidney of a patient lying in a face-down position.

Referring to FIG. 5, the needle insertion offset is defined as the distance between a guide point that is selected as a target point and the center point. The size of the needle insertion offset varies among selected guide points 502–524, 552–570. For example, the needle insertion offset of guide point 518 is shorter than for guide point 504. The farthest distance between the center point and any guide point 502–524, 552–570 is the maximum needle insertion offset provided by the imaging grid 290. In this embodiment, the maximum needle insertion offset of the imaging grid 290 for the needle guiding device 126 is approximately 1 inch. In other embodiments, the maximum needle insertion 782a, 782b offset can range well above this length.

The needle insertion offsets 782a, 782b are illustrated relative to the center point locations 280a, 280b and guide point 504. The target is shown to be located at two possible depths 410a, 410b below the top surface of the base plate 220. A relationship exists between the length of the needle insertion offset, the size of the depth angle and the depth of the target below the base plate 220. With respect to the depth of a particular target 410*a*, 410*b* below the base plate 220, the size of the depth angle 416*aa*, 416*ab*, 416*ba* and 416*bb* is inversely proportional to the size of the needle insertion offset 782*a*, 782*b*. The smaller the needle insertion offset 782*a*, 782*b*, the larger the depth angle 416*aa*, 416*ba*, 416*ba* and 416*bb* with respect to the depth of a particular target 410*a*, 410*b*.

For example, the needle insertion offset 782*b* is substantially larger than the needle insertion offset 782*a*. With respect to the target 410*a* having a depth 784*a*, the depth angle 416*aa* associated with the smaller needle insertion offset 782*a* is larger than depth angle 416*ba* associated with the larger needle insertion offset 782*b*. The same type of relationship applies between needle insertion offsets 782*a*, 782*b* and the target 410*b* having a depth of 784*b*. When the size of the needle insertion offset 782*a*, 782*b* is zero, the guide point 504 and the center point have the same location on the imaging grid 290. Accordingly, the size of the depth angle 416 equals a right 90 degree angle directed downward from the reference plane 430.

The size of the depth angle 416 is also dependent upon the actual depth of the particular target 410*a*, 410*b* below the reference plane 430. For a particular needle insertion offset 782*a*, 782*b* a deeper target 410*b* requires a larger depth angle 416 for the needle trajectory 414 to intersect the target 410*a*, 410*b*. For example, for a needle insertion offset 782*a*, the target 410*a* having a depth 784*a* has a smaller depth angle 416*aa* than the depth angle 416*ab* corresponding to the needle insertion offset 782*a* and a deeper target 410*b* having a 784*b* larger depth than the depth 784*a*. The same type of relationship applies between needle insertion offset 782*b* and the targets 410*a* and 410*b* with depths 784*a* and 784*b* respectively.

Again referring to FIG. 6, the direction of the aiming line 240 indicates the directional component of the needle insertion trajectory 414 that is projected along the reference plane 430. The aiming line 240 is parallel to the reference plane 430 and to the top surface of the base plate 220 and to the top surface of the guide platform 230. The aiming line 240 also is aligned with the two dimensional directional component of the needle insertion trajectory 414, which is equal to the two dimensional directional component of the guide shaft axis 324, that is parallel to the reference plane 430. When the aiming line 240 is directed towards a guide point 502–524, 552–570, the directional component of a needle insertion trajectory 414 with respect to the reference plane 430 is also directed towards the guide point 502–524, 552–570. Accordingly, the direction of the aiming line 240 serves as an accurate indicator of the direction of the needle insertion trajectory 414 with respect to the reference plane 430.

The following description summarizes the use of a needle guiding device 126 according to the invention. First, a medical professional 108 chooses a target 410 and identifies its approximate location inside the body of a patient 110. The fluoro axis 124 is initially in a downward vertical position that is also known as the Anterior Posterior (AP) position. Next, the medical professional 108 chooses an approximate location of a needle insertion point along the outer surface of the patient 110. The medical professional 108 chooses the needle insertion point based upon a desired needle insertion trajectory 414. Considerations for choosing a needle insertion trajectory 414 include the location of the target 410, the shape of the target 410, and the surrounding body structures that the medical professional 108 may wish to bypass. The imaging grid 290 and the guide platform 230 are positioned parallel to the surface of the earth.

Next, the medical professional 108 aligns a fluoro axis 124 such that it aligns with the approximate location of the target 410 and the approximate location of the needle insertion point. The medical professional 108 adjusts the position of the fluoro axis 124 while viewing a fluoroscope display 116. When an image of the target 410 is displayed, a first fluoro axis position 424 is defined.

Next, the medical professional 108 selects a guide point 502–524, 552–570 on the imaging sight (for example, the imaging grid) as a starting point. The starting point is the first target point selected during this procedure. A target point is a guide point 502–524, 552–570 that indicates a location on the needle guiding device where a target locating fluoro axis 124 intersects or will intersect the needle guiding device 126. The needle guiding device 126 is positioned on the patient 110 such that the selected guide point 504 is aligned with the first fluoro axis position. Also, the needle guiding device 126 is positioned such that its center (e.g., the center point 280) is slightly offset from the location where a needle 442 will be inserted. The medical professional 108 rotates a guide platform 230 so that an aiming line 240 associated with the guide platform 230 aligns with the guide point 504 chosen as the starting point. Alternatively, this step can be performed later in the procedure. If performed during this step of the procedure, movement of the needle guiding device 126 or of a component of the needle guiding device 126 is minimized later on in the procedure. In this orientation, the common point 330 also is adjacent to the location where a needle 442 will be inserted. In this alignment, the image of the guide point 504 and the target 410 appear to overlap on the fluoroscope display screen.

Next, the medical professional 108 repositions and aligns the fluoro axis 124 such that the fluoroscope display 116 shows an image of the edge of the radiopaque material of the guide shaft 232, located at the locus 341, superimposed on the image on the target 410. In this position, the common point 330 and the target 410 are aligned along the fluoro axis 124. This is the second fluoro axis position 426.

One example of how the medical professional 108 can achieve alignment of the common point 330 and the target 410 follows. The medical professional 108 chooses two guide lines (for example 530–536, 572) on the imaging grid 290. One of these guide lines (for example 572) issues from the guide point 504 chosen as the starting point and one of these guide lines (for example 530) issues from the center of the needle guiding device 126 (e.g., the center 280 of the base plate 220). Each of these lines meets at a 90 degree angle. The medical professional 108 then moves the fluoro axis 124 such that it intersects the intersection of these guide lines 572, 530 (an intermediate guide point 518).

On the fluoroscope display 116, the image of the intermediate guide point 518 is superimposed on the target 410. Then, the medical professional 108 moves the fluoro axis 124 such that it intersects the center of the needle guiding device 126 (the common point 330) and the target 410. The fluoroscope display 116 shows the image of the edge of the radiopaque material 340 of the guide shaft 232, located at the locus 341, superimposed on the image of the target 410. This is the second fluoro axis position 426.

If the guide point (for example 520) chosen as the starting point fortuitously happens to be aligned with the target 410 and is aligned along a guide line (for example 530) that issues from the center of the needle guiding device 126, then the medical professional 108 need only move the fluoro axis 124 along this one guide line 530 to achieve the second fluoro axis position 426.

The medical professional 108 then rotates a guide platform 230, if not rotated previously, so that an aiming line 240 associated with the guide platform 230 aligns with the guide point 504 chosen as the starting point. The guide shaft 232 then is repositioned, using the guide rod 236, to align the axis of the guide shaft 324 with the fluoro axis 124 in the second fluoro axis position 426. When aligned, the guide shaft 232 projects its smallest profile image in the fluoroscope display 116. The guide shaft profile image appears as a circle and appears to be superimposed on the image of the target 410. When the guide shaft 232 is in this alignment, the medical professional 108 locks the position of the guide shaft 232 using a guide rod 236 locking mechanism 249.

Next, and optionally, the medical professional 108 repositions the fluoro axis 124 to a position it was in prior to being in the second fluoro axis position 426 (for example, the first fluoro axis position 424), if he or she wishes to view a needle as it is inserted into a patient 110 on the fluoroscope display 116. However, the fluoro axis 124 can be repositioned to any position that is not substantially the same as the second fluoro axis position 426 in order to view the needle 442. In this position, the guide shaft 232 no longer projects its smallest profile image in the fluoroscope display 116. The image of the guide shaft 232 now appears to have an oblong shape with its long dimension directed towards the target 410.

Finally, the medical professional 108 inserts the needle 442 through the guide shaft 232 which is aligned with the target 410. The image of the needle 442 appears as an oblong shape in the fluoroscope display 116 with its long dimension directed towards the image of the target 410. If the needle 442 is viewed while being inserted, the image of the needle 442 appears to move towards the image of the target 410. The medical professional 108 ceases inserting the needle 442 when he or she feels the target 410 and/or when he or she sees the image of the needle 442 connect with the image of the target 410.

The precise anatomy of each patient 110 varies. The medical professional 108 selects an approximate location of a needle insertion point along the outer surface of the patient 110. This selection is based upon the type of operation to be performed and upon the particular anatomy of the patient 108. The fluoroscope 100 can be used to peer inside the body of the patient 110 to identify the precise location of the target. The medical professional 108 positions the fluoro axis 124 towards the approximate location of a target 410. Preferably, the fluoro axis 124 is positioned to also intersect the outer surface of the patient 110 in the vicinity of the selected approximate location of the needle insertion point.

Figure 7:
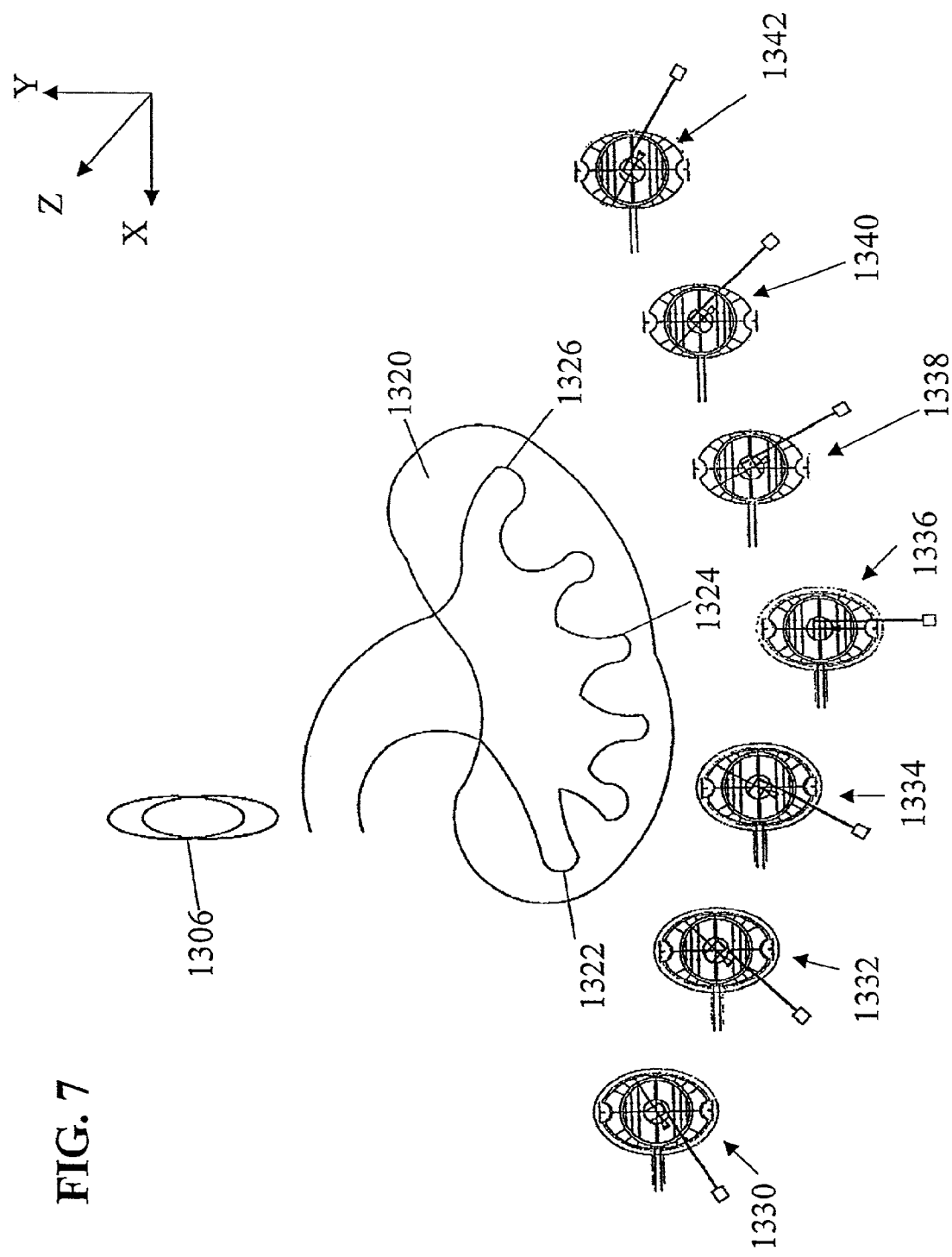
FIG. 7 is a illustrative view of the relationship between a needle insertion offset, a depth of a target and a depth angle of the needle insertion trajectory.

Referring to FIG. 7, the target 410 is typically located inside the human body and is not visible to the human eye. For example, the target 410 can be a point located inside of a kidney 1320. A kidney includes a main body of tissue 1320 and multiple protrusions of tissue 1322–1326 extending from the main body 1320. Each protrusion of tissue is called a calyx 1322–1326. The target 410 may be a point located inside of a calyx 1322–1326 or located inside the main body 1320 of the kidney. The guide platform 230 positions 1330–1342 indicate various directions from which a needle 442 can be inserted from the needle insertion device 126 to the kidney 1320. A target, such as a kidney 1320, has substantially no inherent radiopaque properties and is not usefully visible when attempted to be seen from the fluoroscope display 116. A radiopaque die is added to the kidney 1320 to enhance its visibility from the fluoroscope display 116. Upon intersection of the fluoro axis 124 and a kidney filled with radiopaque die, the fluoroscope display 116 reveals the radiopaque image of the kidney.

For a particular operation, the needle 442 may be required (or chosen) to contact a particular calyx 1322–1326 at the its outer tip or may be required (or chosen) to enter the calyx from a particular angle or direction. For example, the needle 442 may be required to enter the outer tip along the length or longitudinal axis of the calyx 1322–1326. The outer tip of the upper calyx 1326 of the right kidney is located at the highest elevation of any calyx of that kidney 1320 within the patient's body. A needle insertion trajectory 414 directed towards the upper calyx 1326 can risk contact with the eleventh rib or the right lung.

The fluoroscope 100 can be used to identify the precise location of the right kidney, its upper calyx 1326, the eleventh rib, the right lung and other nearby internal structures. Also, the fluoroscope 110 can be used to aid with the determination of a needle insertion point and a needle insertion trajectory 414. A needle insertion trajectory 414 intersecting the tip of the upper calyx 1326 and circumventing the eleventh rib, the right lung and other vital internal structures can be determined by the medical professional 108.

Referring to FIG. 6, a target locating fluoro axis position 424, 426 is any position of the fluoro axis 124 that intersects a particular target 410. A target locating fluoro axis point is a point along the outer surface of the patient 110 that intersects a target locating fluoro axis 424, 426. The medical professional 108 identifies the point location along the outer surface of the patient 110 that appears to intersect the target locating fluoro axis 424, 426. This location is identified by extrapolating the position of the target locating fluoro axis position 424 relative to the location of the fluoroscope emitter 102, the fluoroscope receiver 106 and the patient 110.

Preferably, the target locating fluoro axis point (i.e., the location where the target locating fluoro axis intersects the outer surface of the patient) is located in proximity to the needle insertion point. The distance between these two point should be within a distance equal to the maximum needle insertion offset. If true, the previously selected approximate needle insertion point can be selected as the precise needle insertion point. If not true, the medical professional can elect to re-select a precise needle insertion point that is located with respect to the target locating fluoro axis point within a distance equal to the maximum needle insertion offset.

Alternatively, the medical professional 108 may elect to re-position the fluoro axis 124 to another target locating fluoro axis point that is located with respect to the approximate needle insertion point within a distance equal to the maximum needle insertion offset. In some circumstances, the medical professional 108 may elect to alternate between re-positioning the target locating fluoro axis point and reselecting the needle insertion point to effect a precise needle insertion trajectory 414.

The needle guiding device 126 can be used to determine the precise location of the target locating fluoro axis point and the precise location of the needle insertion point. Both points lie along the outer skin surface of the patient 110. The location of the center point 280, as approximated by the location of the common point 330, and the guide points 502–520, 552–570 of the needle guiding device 126 are visible via the fluoroscope display 116. The medical professional 108 can elect to position the needle guiding device 126 in order to align a selected guide point 502–520, 552–570 with a current target locating fluoro axis point. Typically, the current fluoro axis point corresponds with the center of the fluoroscope display 116.

While maintaining intersection of the selected guide point 502–524, 552–570 with the target locating fluoro axis position 424, 426, the medical professional 108 can re-position the needle guiding device 126 to select a precise needle insertion point located at the vicinity of the center point 280. Alternatively, the medical professional 108 can elect to position the needle guiding device 126 to align the vicinity of the center point 280 with a selected approximate needle insertion point as seen from normal eyesight. While maintaining alignment of the center point 280 with the selected approximate needle insertion point, the medical professional 108 can re-position the fluoro axis 424, 426 to intersect with a selected guide point 502–524, 552–570 as a target point. Regardless of which use technique is used, the resulting target locating fluoro axis position 424 is identified as the first target locating fluoro axis position 424.

The target locating fluoro axis point and the needle insertion point are preferred to have separate locations. Each point defines a needle insertion trajectory 414 that intersects the target 410. Separate locations effect a separate needle insertion trajectory and a separate target locating fluoro axis trajectory. This use technique aids the medical professional 108 to better view contact between a needle 442 and the target 410 while viewing the fluoroscope display 116.

Although the fluoro axis 124 is oriented in 3-dimensional space, the fluoroscope display 116 provides a two dimensional image lacking depth perception. When the needle insertion trajectory 414 and the target locating fluoro axis position are the same, the profile of the needle 442 while being inserted towards the target 410 obscures the point of contact between the needle 442 and the target 410. Consequently, a needle 442 can be directed towards a target 410 with no indication from the fluoroscope display 116 that the target 410 was contacted, under shot or over shot by the needle 442.

Separating the needle insertion trajectory 414 and the target locating fluoro axis trajectory creates a "triangulation" effect where the needle insertion trajectory 414 and the target locating fluoro axis trajectory intersect like sides of a triangle at a common corner point. The corner point is located at the target location 410. This use technique enables the medical professional 108 to view the insertion of the needle 442 and its contact with the target 410 via the fluoroscope display 116 from an angle similar to that provided by side view perspective of the needle trajectory 414 and the target 410.

Referring again to FIG. 6, regardless of what use techniques are selected by the medical professional 108, a guide point 502–524, 552–570 is selected as a target point. Also, the needle guiding device 126 and the target locating fluoro axis 124 are positioned to align the location of the target point with the position 424 of the target locating fluoro axis 124. The needle guiding device 126 is also positioned to align the location of the center point 280 with the location of the precise needle insertion point along the outer skin surface of the patient 110. Accordingly, the fluoroscope display 116 shows the target point and the target 410 located (superimposed) at the same location on the fluoroscope display 116. The location of the center point 280 is also visible from the fluoroscope display 116.

The medical professional 108 rotates the position of the guide platform 230 so that the aiming line 240 is directed towards the selected target point. Next, the medical professional 108 re-positions the fluoro axis 124 to a second position that intersects both the target 410 and the location of the center point 280 of the needle guiding device 126. This step can be optionally performed with or without the use of the guide lines (for example 530–536, 572) of the imaging grid 290. The second position of the fluoro axis 124 is a second target locating fluoro axis position 426. The second target locating fluoro axis position now defines the needle insertion trajectory 414.

The medical professional 108 aligns the guide shaft 232 with the second target locating fluoro axis position 426 according to visual feedback provided by the fluoroscope display 116. When in alignment, the guide shaft 232 projects the smallest profile onto the fluoroscope display 116. The guide rod 236 is used to move the guide shaft 232 into alignment with the fluoro axis 124. The guide rod locking mechanism is used to lock the position of the guide shaft 232 and guide rod 236.

Next, the medical professional 108 repositions the fluoro axis 124 back into the first target locating fluoro axis position to enable a triangulated view of the target 410 and the needle insertion trajectory 414. Finally, the medical professional 108 places a needle 442 into the guide shaft 232 and inserts the needle from the guide shaft 232 towards the target 410. Contact between the needle 442 and the target 410 is indicated by the fluoroscope display 116.

Re-positioning the fluoro axis 124 between the target point and the center point 280 can be difficult to perform. A fluoroscope arm 106 (best shown in FIGS. 1A–1B) typically moves accurately and efficiently along one or more well defined paths of movement. These paths of movement define planes of movement. Re-positioning the fluoro axis 124 between the target point and the location of the center point 280 typically requires movement over more than one defined plane of movement of the fluoroscope 100.

Guide lines (for example 530–536, 572) of the imaging grid 290 can aid the medical professional 108 to reposition the fluoro axis 124 between various points, including guide points 502–524, 552–570 and the location of the center point 280, located on the imaging grid 290. Guide lines (for example 530–536, 572) form a path of inter-connected lines between guide points 502–524, 552–570 and the center point 280. These guide lines (for example 530–536, 572) inter-connect at 90, 180 or 270 degree angles.

In use, the imaging grid 290 can be aligned with the defined planes of movement of the fluoroscope 100. When aligned, the medical professional 108 is able to re-position the fluoro axis 124 along guide lines (for example 530–536, 572) visible from the fluoroscope display 116. Preferably, the imaging grid 290 and the guide platform 230 are positioned parallel to the surface of the earth. The outer stabilizer rim 208 can be utilized to level the needle guiding device 126 parallel to the surface of the earth. These guide lines (for example 530–536, 572) show an exact path for the fluoro axis 124 to follow between two points located on the imaging grid 290.

Testing of the accuracy of fluoroscope alignment can be performed using one or more guide lines (for example 530–536, 572). When repositioning the fluoro axis 124 between two guide points 502–524, 552–570 connected by a guide line (for example 530–536, 572) that is aligned with a defined plane of movement of the fluoroscope 100, the fluoro axis 124 should continuously intersect the guide line while repositioning between the two guide points. Movement of the fluoro axis 124 away from the intersecting the guide line (for example 530–536, 572) that is aligned with a defined plane of movement of the fluoroscope 100 can be an indication of fluoroscope mis-alignment or needle guide device 126 mis-alignment.

Figure 8A:
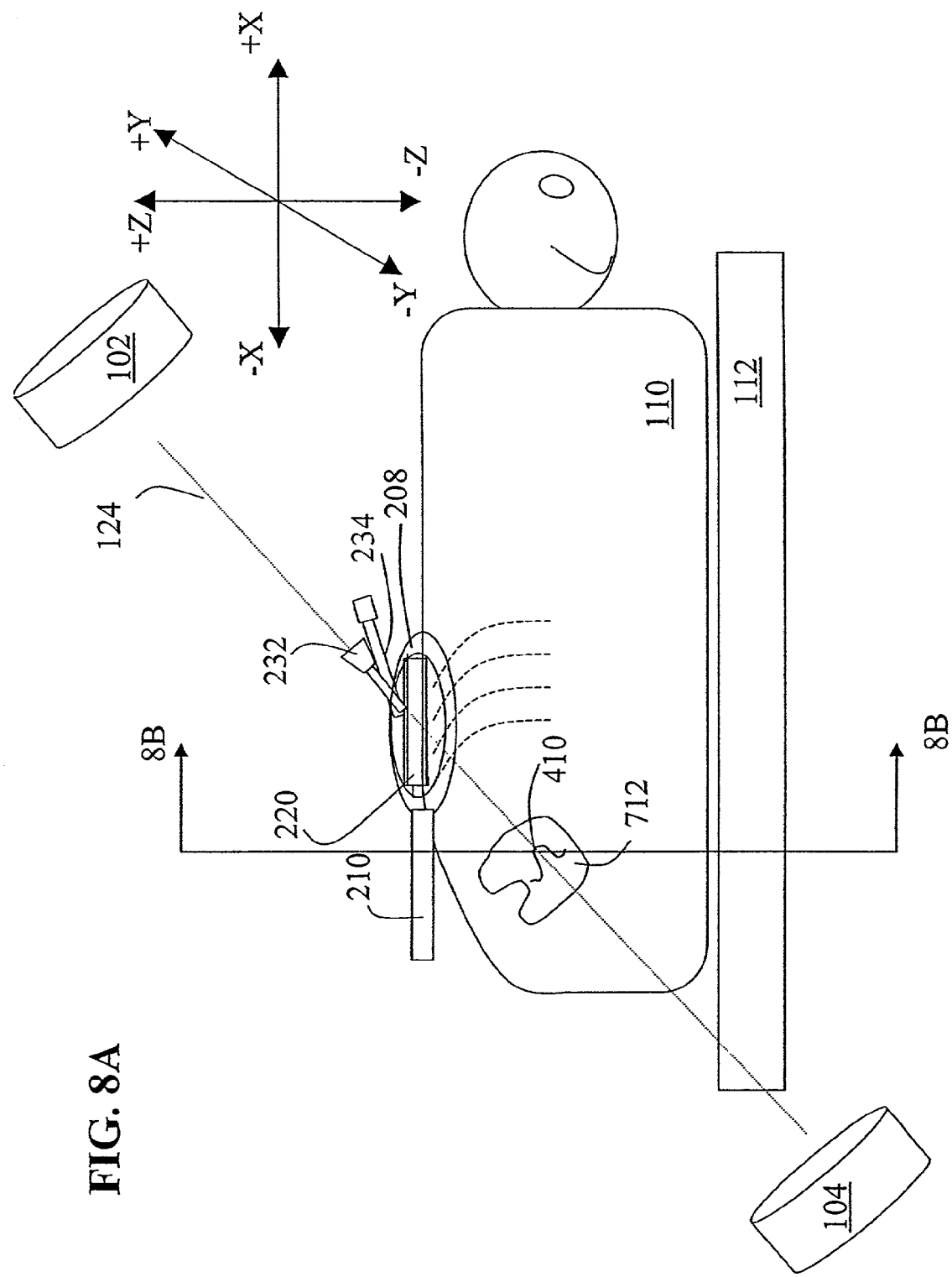
FIG. 8A is a schematic side view from the vantage point of the medical professional of FIG. 1A of the embodiment of the needle guiding device shown in FIG. 2A positioned along the outer skin surface of the patient.
Figure 8B:
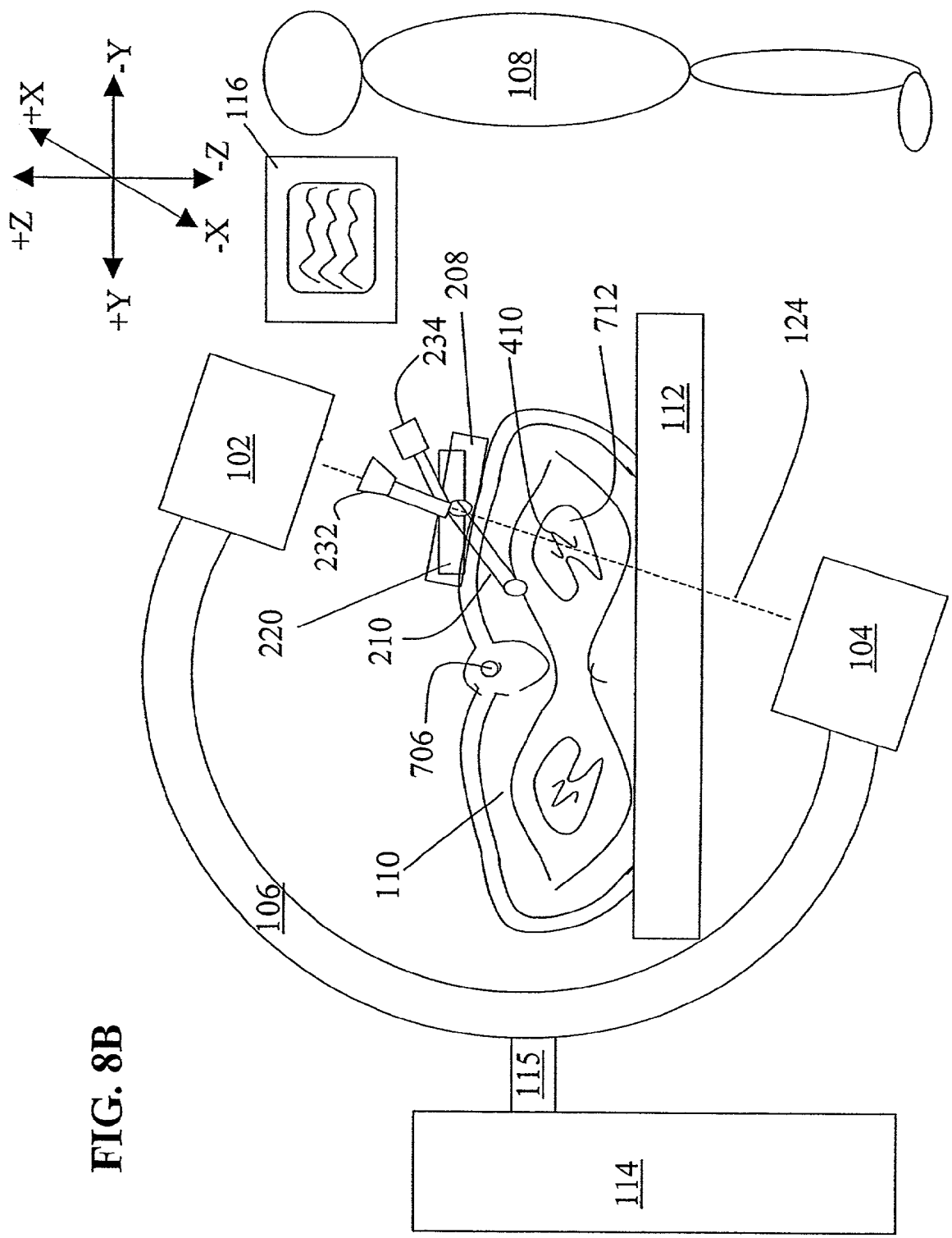
FIG. 8B is a schematic end-on cross-section taken along line 8B—8B in FIG. 8A.

Referring to FIGS. 8A–8B, the needle guiding device 126 is positioned along the outer skin surface of the patient 110. In FIG. 8A, the needle guiding device 126 and the patient 110 are seen from the viewing perspective of the medical professional 108, as illustrated in FIGS. 1A–1B. The patient 110 is lying face down on the operating table 112. The needle guiding device 126 is positioned along the contours of the outer skin surface of the patient 110 in proximity to the right kidney 712.

The handle 210 of the needle guiding device 126 is located towards the left hand side of the medical professional 108. The outer stabilizer rim 208 is locked into a position that is not aligned with the position of the base plate 220. The side of the outer stabilizer rim 208 nearest to the perspective of the viewer is contacting the skin surface of the patient 110. The side of the base plate 220 farthest from the perspective of the viewer is also contacting the skin surface of the patient 110. The outer rim 208 and the base plate 220 form two points of contact that provide fuller and more stable support of the needle guiding device 126 along the outer contours of the patient 110.

The fluoroscope emitter 102 and the fluoroscope receiver 104 are attached to the fluoroscope arm 106. The fluoroscope arm 106 is positioned such that the fluoro axis 124 intersects the upper calyx 410 of the right kidney 712 of the patient 110. The fluoro axis 124 is positioned in a substantially diagonal and downward direction along the X-Z vertical plane.

Referring to FIG. 8B, a cross sectional perspective of the patient 110 of FIG. 8A is shown from the viewing perspective of FIG. 1A. A cross section partitioning the upper and lower portions of the body of the patient 110, indicated by cross section delimiting line 708, is shown to reveal her left and right kidney 712 and her spine 706. The needle guiding device 126 is positioned as shown in FIG. 7A. The fluoro axis 124 is positioned in a substantially diagonal and downward direction along the Y-Z vertical plane while being simultaneously it positioned in a substantially diagonal and downward direction along the X-Z vertical plane as shown in FIG. 8A.

Figure 9A:
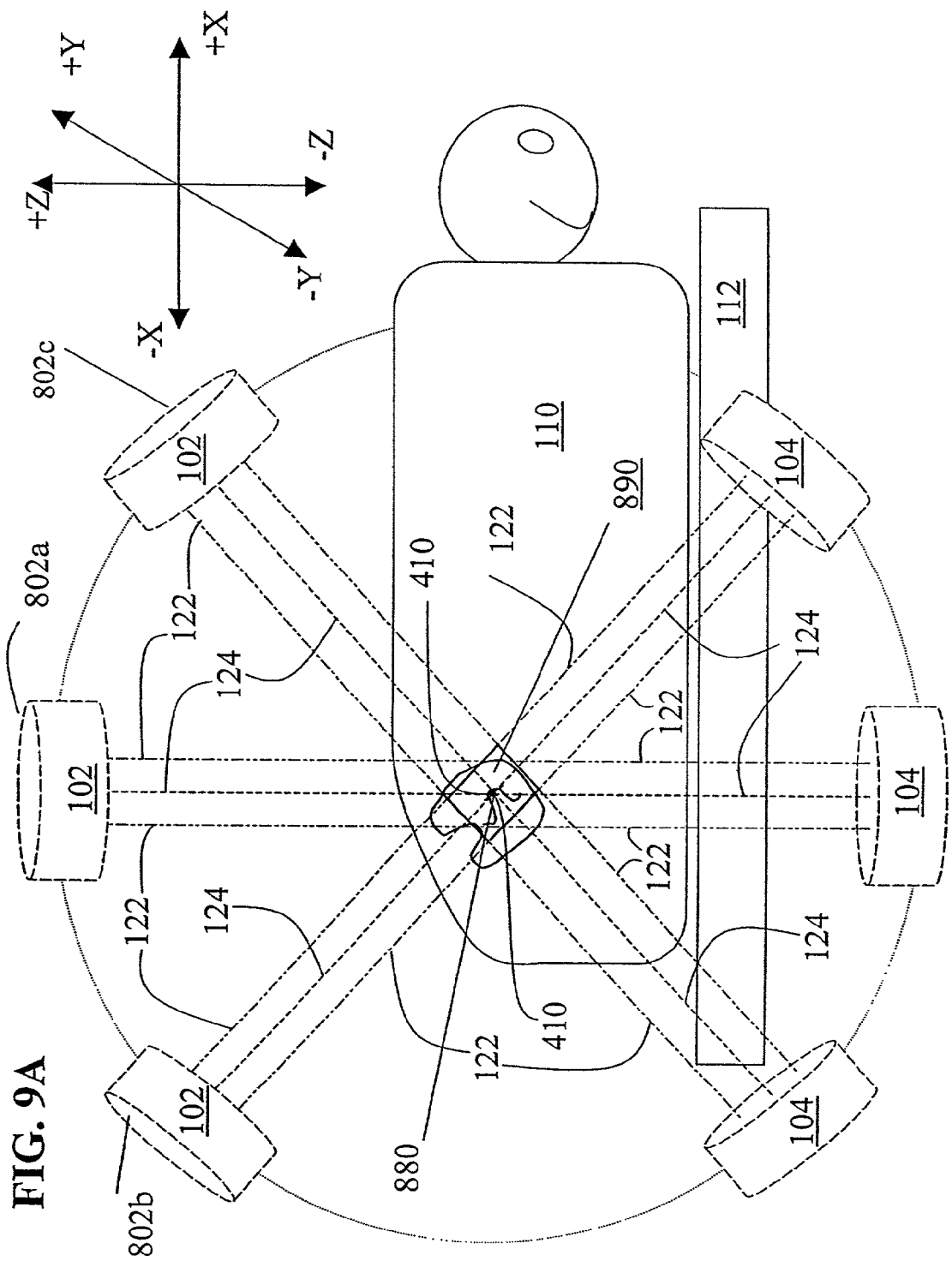
FIG. 9A is a schematic side view from the vantage point of the medical professional of FIG. 1A depicting movement of a fluoroscope emitter and fluoroscope receiver along an X-Z vertical plane.

Referring to FIGS. 9A–9B, the fluoro beam 122 and the fluoro axis 124 are re-positionable along both the X-Z and the Y-Z vertical planes. In FIG. 9A, positioning of the fluoro beam 122 and the fluoro axis 124 are illustrated along the X-Z vertical plane from the viewing perspective of the medical professional 108, as illustrated in FIGS. 1A–1B. The position of the fluoroscope emitter 102 and the fluoroscope receiver 104 define the position of the fluoro beam 122 and the fluoro axis 124.

Multiple positions of the fluoro beam 122 and its fluoro axis 124 are shown within the X-Z vertical plane. The fluoro beam 122 and the fluoro axis 124 are shown to rotate within the X-Z vertical plane causing the fluoro beam 122 and fluoro axis 124 to tilt from a vertical position 802a that is parallel to the Z axis, to a substantially downward and diagonal position 802b, 802c. The fluoro beam positions corresponding to the fluoro axis positions 802a, 802b, 802c all intersect within a three dimensional fluoro beam intersection space 890 surrounding a fluoro axis center point 880. The center point of each fluoro axis corresponding to the fluoro axis positions 802a, 802b, 802c intersect at the fluoro axis center point 880. The fluoro axis center point 880 is located at the same location as the target 410. The fluoro beam 122, is typically about 6 inches in diameter and surrounds the fluoro axis 124.

Positioning the target 410 within the fluoro beam intersection space 890 enables the fluoro beam 122 to re-position within the X-Z vertical plane while maintaining an intersection with the target 410. Positioning the target 410 so that it intersects the fluoro axis center point 880, enables the medical professional 108 to re-position the fluoro axis 124 with respect to both the X-Z vertical plane while maintaining the intersection between the fluoro axis 124 and the target 410. The fluoro axis 124 is not required to intersect the needle guiding device 126 when it is being utilized and viewed via the fluoroscope display 116. The needle guiding device 126 can be utilized and viewed via the fluoroscope display 116 while only a portion of the fluoro beam 122 intersects the needle guiding device 126.

Referring to FIG. 9B, the movement of the fluoro beam 122 and the fluoro axis 124 along the Y-Z vertical plane is shown from the viewing perspective provided by FIG. 1A. Multiple positions of the fluoro beam 122 and the fluoro axis 124 are shown within the Y-Z vertical plane. The fluoro beam 122 and the fluoro axis 124 are shown to rotate within the Y-Z vertical plane causing the fluoro beam 122 and the fluoro axis 124 and to tilt from a vertical position 802a that is parallel to the Z axis, to a substantially downward and diagonal position 802d, 802e. The center point of each fluoro axis 124 corresponding to the fluoro axis positions 802a, 802b, 802c (best seen in FIG. 9A) and fluoro axis positions 802d, 802e intersect at the fluoro axis center point 880. The fluoro beam positions 122 corresponding to the fluoro axis positions 802a, 802b and 802c (best seen in FIG. 9A), and to the fluoro axis positions 802d, 802e all intersect in the three dimensional fluoro beam intersection space 890 surrounding the fluoro axis center point 880.

Positioning the target 410 within the fluoro beam intersection space 890 enables the fluoro beam 122 to re-position within the X-Z and the Y-Z vertical planes while maintaining an intersection with the target 410. Positioning the target 410 so that it intersects the fluoro axis center point 880, enables the medical professional 108 to re-position the fluoro axis 124 with respect to both the X-Z and the Y-Z vertical planes while maintaining the intersection between the fluoro axis 124 and the target 410.

Referring to FIGS. 10A–10E, the relative positioning of the imaging grid 290, a target 410, and the fluoro axis 124 is shown while utilizing the needle guiding device 126 to aim a needle towards the target 410. The imaging grid 290 is shown to be positioned horizontal to the surface off the earth and parallel to the X and Y axes 130 of the fluoroscope 100 (best seen in FIGS. 1A–1B).

Figure 10A:
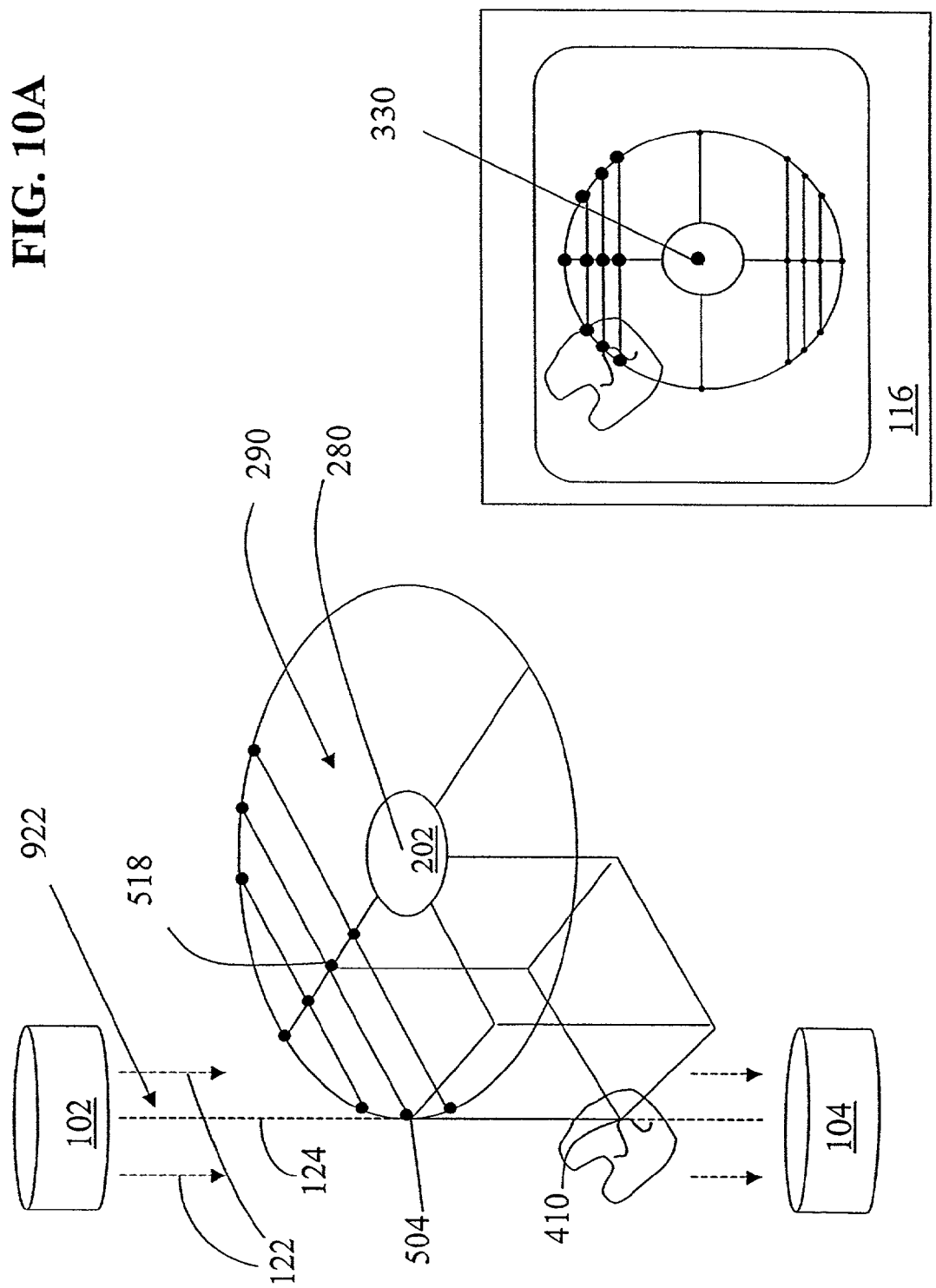
FIGS. 10A–10E schematically depict the relative positioning of the imaging grid, the target, and a fluoro axis while utilizing embodiment of the needle guiding device of FIG. 2A to guide a needle towards the target along a selected needle trajectory.

Referring to FIG. 10A, the target locating fluoro axis position 922 intersects both the guide point 504 and the target 410. The target locating fluoro axis position 922 is defined by the position of the fluoroscope emitter 102 and the fluoroscope receiver 104. The guide point 504 has been selected as a target point to indicate the location of the target 410 and the target locating fluoro axis position 922, with respect to the imaging grid 290. The guide point 504 is also a starting point because it is the first point on the imaging grid 290 to be aligned with the fluoro axis 124 during the needle aiming procedure. The aiming line 240 is re-directed to select and/or identify the starting point while being viewed via the fluoroscope display 116. The fluoroscope display 116 illustrates from the viewing perspective of the target locating fluoro axis position 922 a graphical image of the target 410 appearing to have the same location as the guide point 504.

Figure 10B:
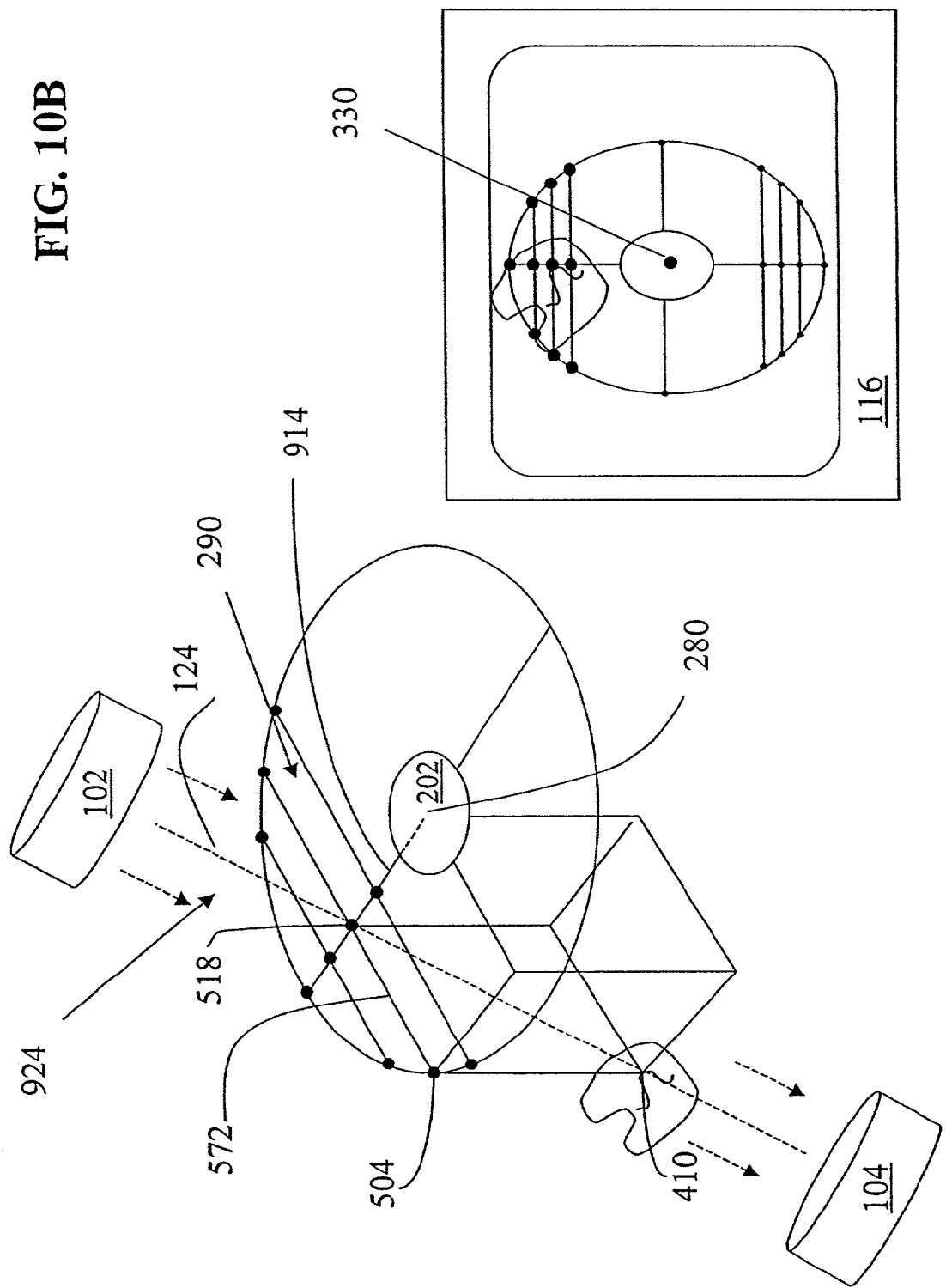

Referring to FIG. 10B, the fluoro axis 124 is re-positioned from a first target locating position 922 that intersects the guide point 504 to a second target locating position 924 that intersects the guide point 518. The fluoro axis 124 is re-positioned along a line of points on the imaging grid 290 defined by the guide line 572. The guide line 572 connects both the guide point 504 and guide point 518 and is aligned with the X axis of the needle guiding device 126 and with the X axis of the fluoroscope 100. The fluoroscope arm 106 is re-positioned about the Y axis of the fluoroscope 100 causing the fluoro axis 124 to move parallel to the X-Z plane of movement of the fluoroscope 100. Preferably, the fluoro axis 124 intersects each point along the guide line 572 while re-positioning from its first position 922 to its second position 924.

Figure 10C:
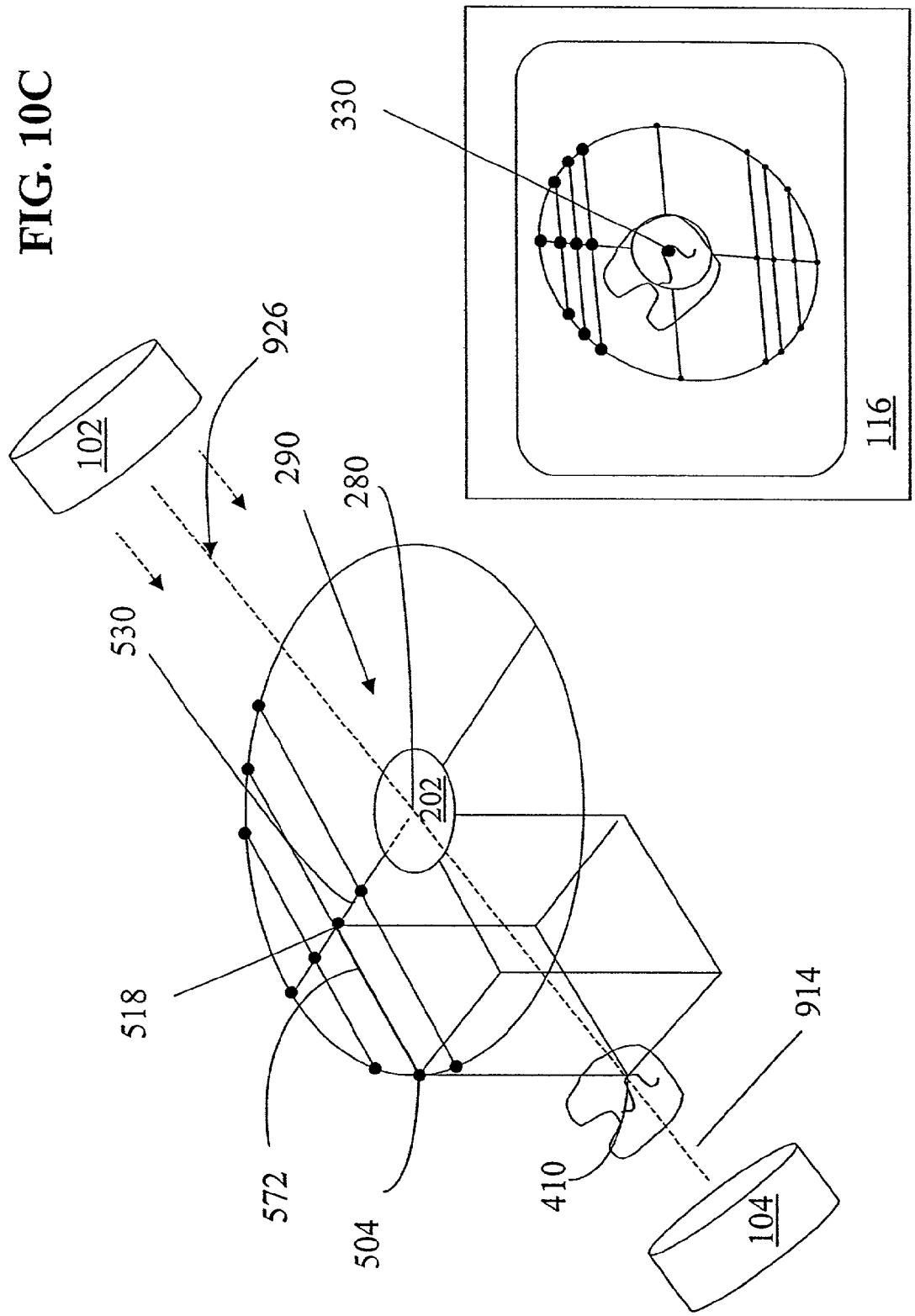
Figure 10D:
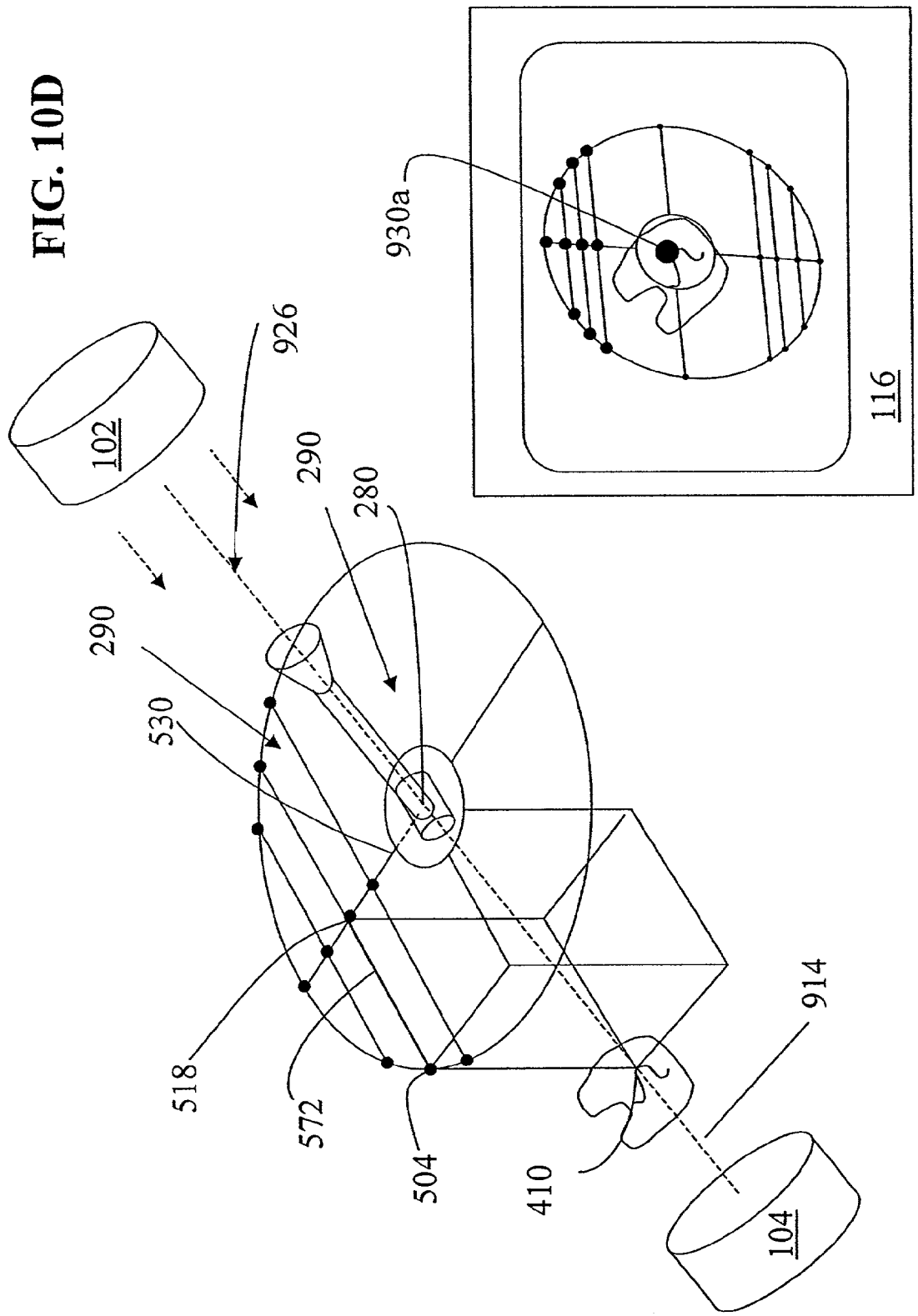

The guide point 518 has been selected as an intermediate point during the repositioning of the fluoro axis 124 between the position 922 intersecting the guide point 504 and the position that ultimately intersects the center point 280 (best seen in FIGS. 10C–10D). The fluoroscope display 116 illustrates a graphical image of the target 410 appearing to have the same location as the guide point 518 from the viewing perspective of the target locating fluoro axis position 924.

Referring to FIG. 10C, the fluoro axis 124 is re-positioned from a second target locating fluoro axis position 924 that intersects the guide point 518 to a third target locating position 926 that intersects the common point 330 and the center point 280. The common point 330 and the center point 280 have the same location. In other embodiments, the common point and the center point have separate locations that are in close proximity to each other. The location of the common point 330, when viewed from the fluoroscope display 116, indicates the location of the center point 280. The fluoroscope display 116 shows the location of the common point 330 as an image of the edge of the radiopaque material 340 at the locus 341 of the guide shaft 232. The fluoro axis 124 is repositioned such that the fluoroscope display 116 shows an image of the edge of the radiopaque material of the guide shaft 232, located at the locus 341, superimposed on the image on the target 410. In this position, the common point 330 and the target 410 are aligned along the fluoro axis 124 in its current target locating position 926.

The target locating fluoro axis position 926 intersects both the common point 330, the vicinity of the center point 280 and the target 410. The fluoro axis 124 is re-positioned along a line of points on the imaging grid 290 defined by the guide line 530. The guide line 530 intersects the intermediate guide point 518 and extrapolates to intersect the common point 330 and the vicinity of the center point 280. The target locating fluoro axis position 926 also defines the needle insertion trajectory 414. Accordingly, target locating fluoro axis position 926 is also the needle insertion fluoro axis position.

The guide line 530 is aligned with the Y axis of the needle guiding device 126 and is aligned with the Y axis of the fluoroscope 100. The fluoroscope arm 106 is re-positioned about the X axis of the fluoroscope 100 causing the fluoro axis 124 to move parallel to the Y-Z plane of movement of the fluoroscope 100. Preferably, the fluoro axis 124 intersects each point along the guide line 530 while re-positioning from the second target locating fluoro axis position 924 to the third target locating fluoro axis position 926.

The guide point 518 is where the fluoro axis 124 transitions from movement along the X-Z plane to movement along the Y-Z plane. Without the aid of the guide point 518 and the guide lines 572 and 530, movement of the fluoro axis may transition from a point along the X-Z plane that is misaligned with a plane of movement intersecting the common point 330. This would require additional trial and error re-positioning of the fluoro axis 124 until it intersects both the target 410 and the common point 330. The fluoroscope display 116 illustrates a graphical image of the target 410 appearing to have the same location as the common point 330 from the viewing perspective of the target locating fluoro axis position 926.

Referring to FIG. 10D, if not aligned earlier in this procedure, the guide shaft 232 is aligned along the needle insertion trajectory 914 defined by the target locating fluoro axis position 926 using the visual feedback from the fluoroscope display 116. Preferably, the aiming line 240 is aligned early in this procedure, for example, when selecting or identifying the starting point. Such operation reduces the likelihood that the needle guiding device 126 will move to become unaligned with the starting point. Moving a portion of the needle guiding device, such as the guide platform 230, may alter the position of the needle guiding device 126 while it is located along the outer skin surface of the patient 110. To align the guide shaft 232, the guide platform 230 is rotated so that an aiming line 240 associated with the guide platform 230 aligns with the guide point 504 chosen as the starting point.

The guide shaft 232 then is repositioned, using the guide rod 236, to align the axis of the guide shaft 324 with the fluoro axis 124 in the second fluoro axis position 926. When aligned, the guide shaft 232 projects its smallest profile image in the fluoroscope display 116. The guide shaft profile image appears as a circle and appears to be superimposed on the image of the target 410. When the guide shaft 232 is in this alignment position, the position of the guide shaft 232 is locked using the guide rod 236 locking mechanism 249 (best seen in FIG. 3B).

Figure 10E:
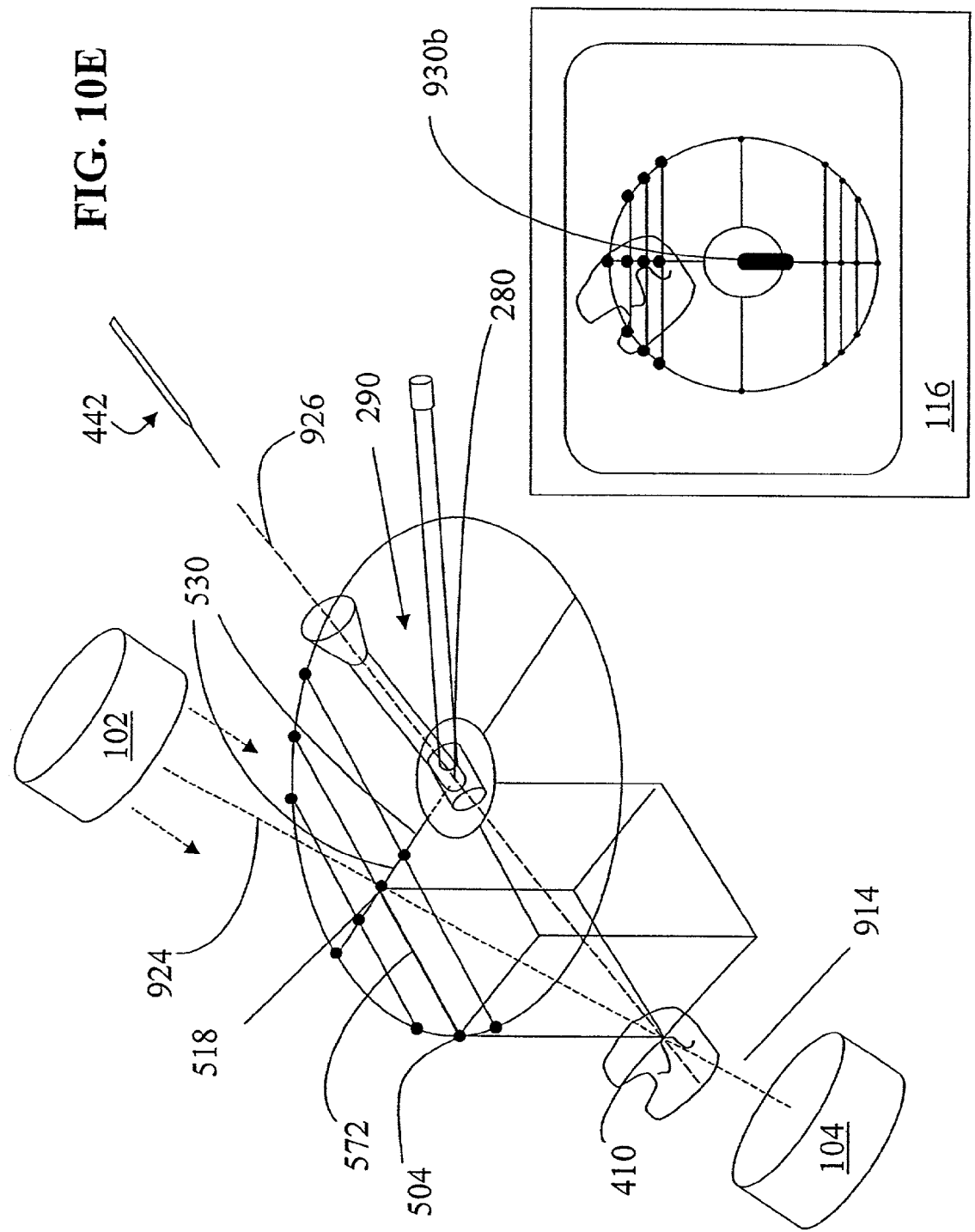

Referring to FIG. 10E, the fluoro axis 124 is re-positioned from the third target locating fluoro axis position 926 intersecting the common point 330 to the second target locating fluoro axis position 924 intersecting the guide point 518. The target locating fluoro axis position 924 intersects both the guide point 518 and the target 410. The fluoro axis 124 is re-positioned along a line of points on the imaging grid 290 defined by the guide line 530. The guide line 530 intersects the guide point 518 and extrapolates to the center point 280.

The target locating fluoro axis position 924 provides a triangulated view of the needle insertion trajectory 914 and the target 410. This position 924 is also identified as a triangulated viewing fluoro axis position. From the viewing perspective of the target locating fluoro axis position 924, the fluoroscope display 116 illustrates a graphical image of the target 410 appearing to have the same location as the intermediate guide point 518.

The guide shaft 232 continues to be aligned along the target locating fluoro axis position 926 defining a needle insertion trajectory 914 as shown in FIG. 10D. From the perspective of the triangulated viewing fluoro axis position 924, the profile image 930b of the radiopaque portion of the guide shaft 232 no longer projects its smallest profile on the fluoroscope display 116. The image of the guide shaft 232 now appears to have an oblong shape 930b with its long dimension directed towards the target 410.

Finally, the needle 442 is inserted through the guide shaft 232 which is aligned with the target 410. The image of the needle 442 appears as an oblong shape in the fluoroscope display 116 with its long dimension directed towards the image of the target 410. If the needle 442 is viewed while being inserted, the image of the needle 442 appears to move towards the image of the target 410. The medical professional 108 ceases inserting the needle 442 when he or she feels the target 410 and/or when he or she sees the image of the needle 442 connect with the image of the target 410.

Figure 11:
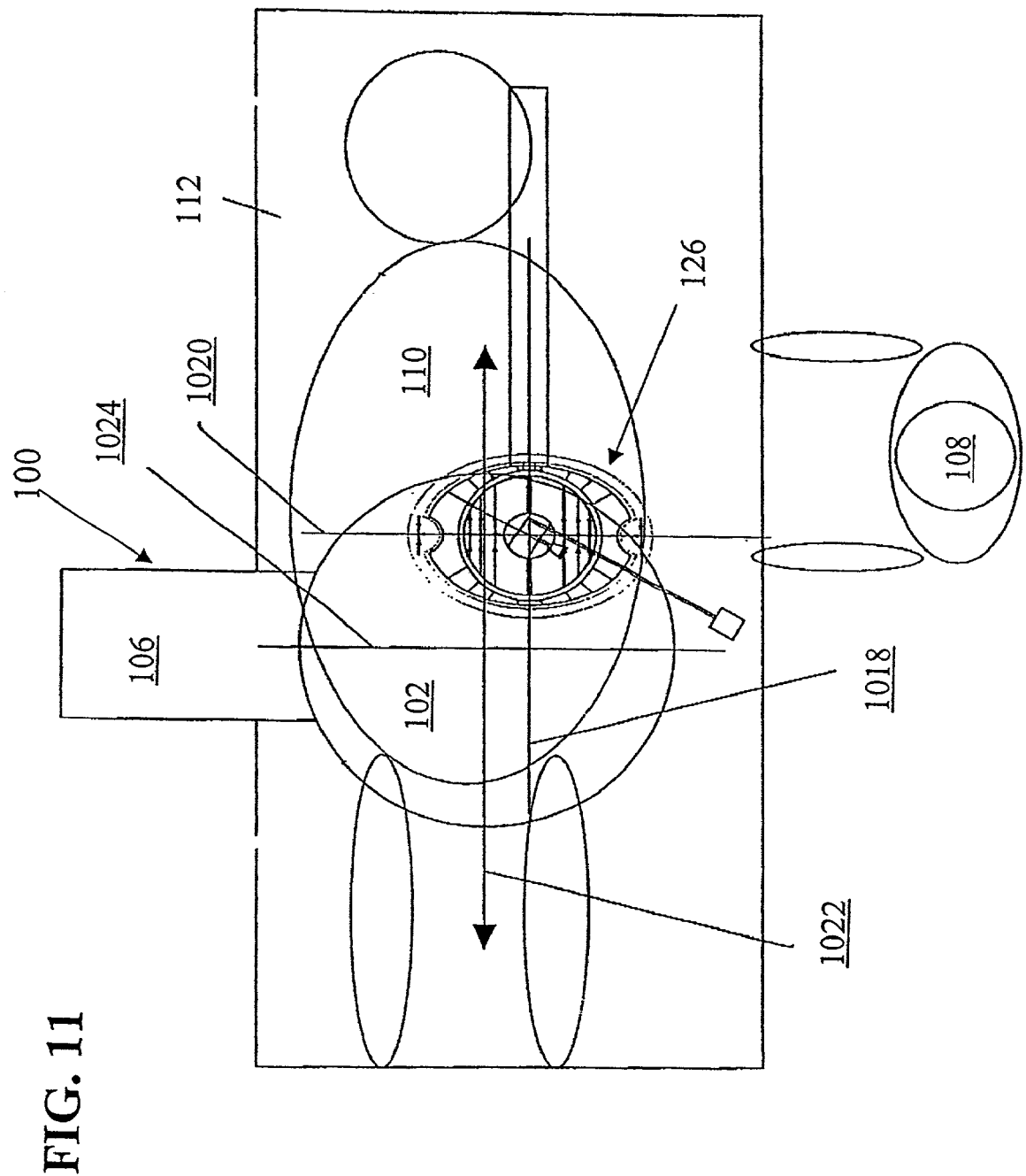
FIG. 11 is a schematic top perspective view of the axes of the needle guiding device and the fluoroscope.

FIG. 11 also shows that the X and Y axis planes of rotation 1022, 1024 of the fluoro axis 124 of the fluoroscope 100 do not need to intersect the X and Y axes 1018, 1020 of the needle guiding device 126. The position of the X axis 1024 of the needle guiding device 126, aligned with the guide lines 534–536 of the imaging grid 290, is shown offset from the X-Z rotation plane 1022 of the fluoroscope 106. The position of the Y axis 1020 of the needle guiding device 126, aligned with the guide lines 530–532 of the imaging grid 290, is shown in a position that is offset from the Y-Z rotation plane 1020 of the fluoroscope arm 106. The X and Y axes 1018–1020 of the needle guiding device 126 need only be parallel to the respective axes 1020, 1022 of the fluoroscope 100. The needle guiding device 126 is preferred to be positioned as close as possible to the fluoro axis 124, the center of the fluoro beam 122, to allow for a maximum view of the needle guiding device 126 from the fluoroscope monitor 116. The patient 110 is also preferred to be positioned with the length of the body parallel to the long dimension of the operating table 112.

Figure 12:
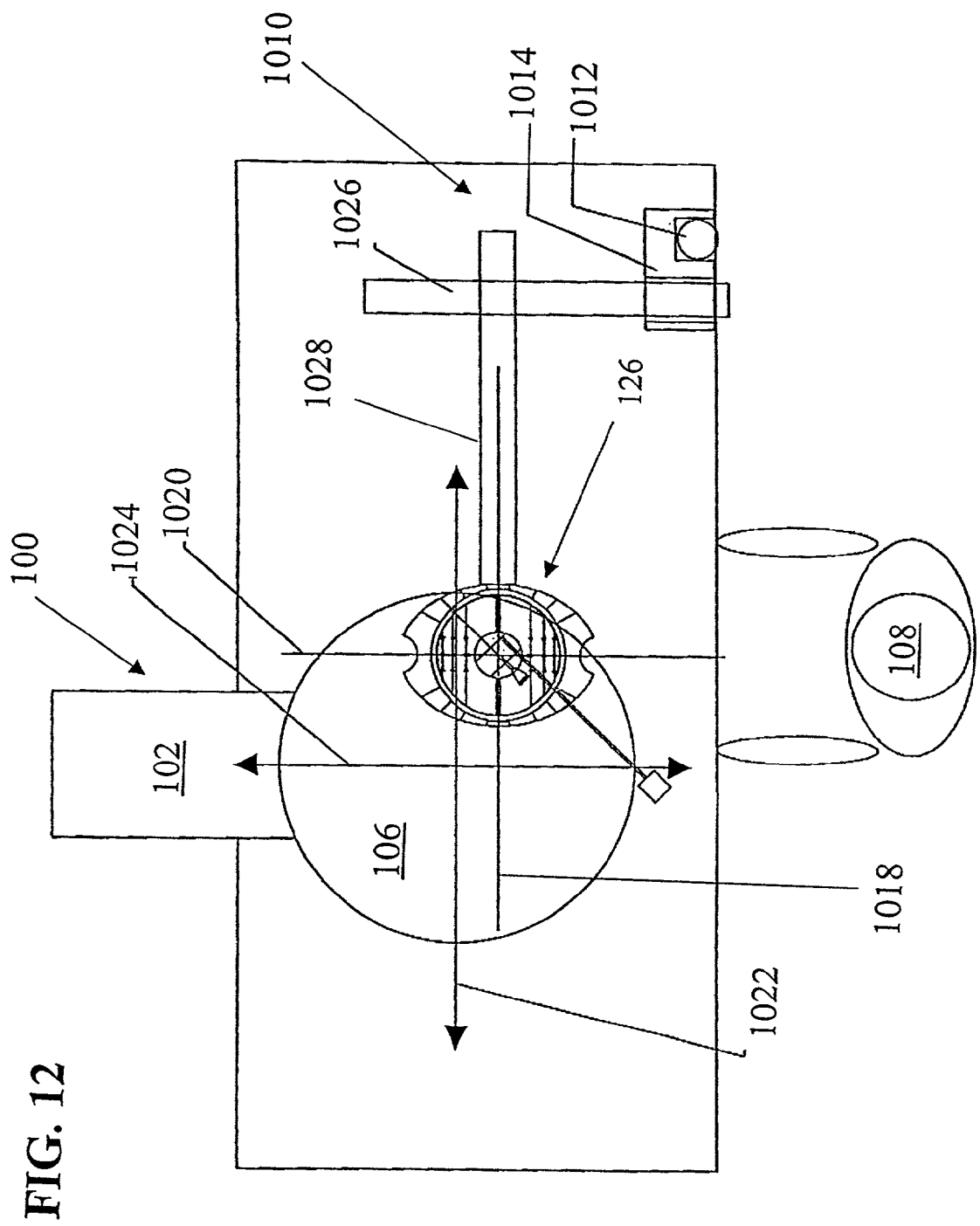
FIG. 12 is a schematic top perspective view of the needle guiding device mounted on a rigid adjustable stand.

Referring to FIG. 12, a rigid adjustable stand 1010 provides stationary support of the needle guiding device 126. The rigid adjustable stand 1010 includes two support arms 1026–1028, a clamp 1014 and a vertical pole 1012. The vertical pole 1012 and the two support arms 1026, 1028 each have a longitudinal dimension. The two support arms 1026–1028 and are attached to each other. The longitudinal dimension of support arm 1026 is substantially perpendicular to the longitudinal dimension of support arm 1028. The clamp 1014 is attached to the support arm 1026 and to the vertical pole 1012. The clamp 1014 is adapted to be repositioned along the longitudinal axis of the vertical pole 1012. The position of the clamp 1014 along the longitudinal axis of the vertical pole 1012 can be locked and unlocked via a clamp locking mechanism to temporarily prevent the movement of the clamp along the vertical pole 1012.

The needle guiding device 126 is mounted on the support arm 1028. The Y axis 1020 of the needle guiding device 126 is aligned with the Y axis 1024 of the fluoroscope 100. The X axis 1018 of the needle guiding device 126 is aligned with the X axis 1022 of the fluoroscope 100. The longitudinal axis of the support arm 1028 is substantially parallel to the X axis 1024 of the needle guiding device 126.

Referring to FIGS. 13A–13B, the needle guiding device 126 is mounted a flexible stand 1034. The flexible cable 1030 within the flexible stand 1034 is tightened to stiffen and lock the needle guiding device 126 into a stationary position. In FIGS. 13A–13B, the longitudinal axis of the handle 210 of the needle guiding device 126 is shown substantially parallel to the top surface of the table 112.

Referring to FIG. 13B, a side view perspective of FIG. 13A is shown where the outer stabilizing rim 208 is set against the outer skin surface of the patient 110. The base plate 220, the guide platform 230 and the outer stabilizing rim 208 and the outer skin surface of the patient 110 are shown substantially perpendicular to the top surface of the table 112.

Referring to FIGS. 14A–14E, the relative positioning of the aiming line 240, the imaging grid 290, the fluoro beam 122 and a target A are shown. The aiming line 240 is represented as the line BC and upper left hand quadrant (northwest quadrant) of the imaging grid 290 is represented as the rectangle ECDB. The imaging grid 290 has four quadrants. Typically, only one quadrant is used during a needle aiming and guiding procedure. The lengths of various geometric lines and the sizes of various geometric angles are provided and expressed as pure unit less numbers for comparison. These values do not to indicate the actual dimensions of the needle guiding device 126.

Figure 14A:
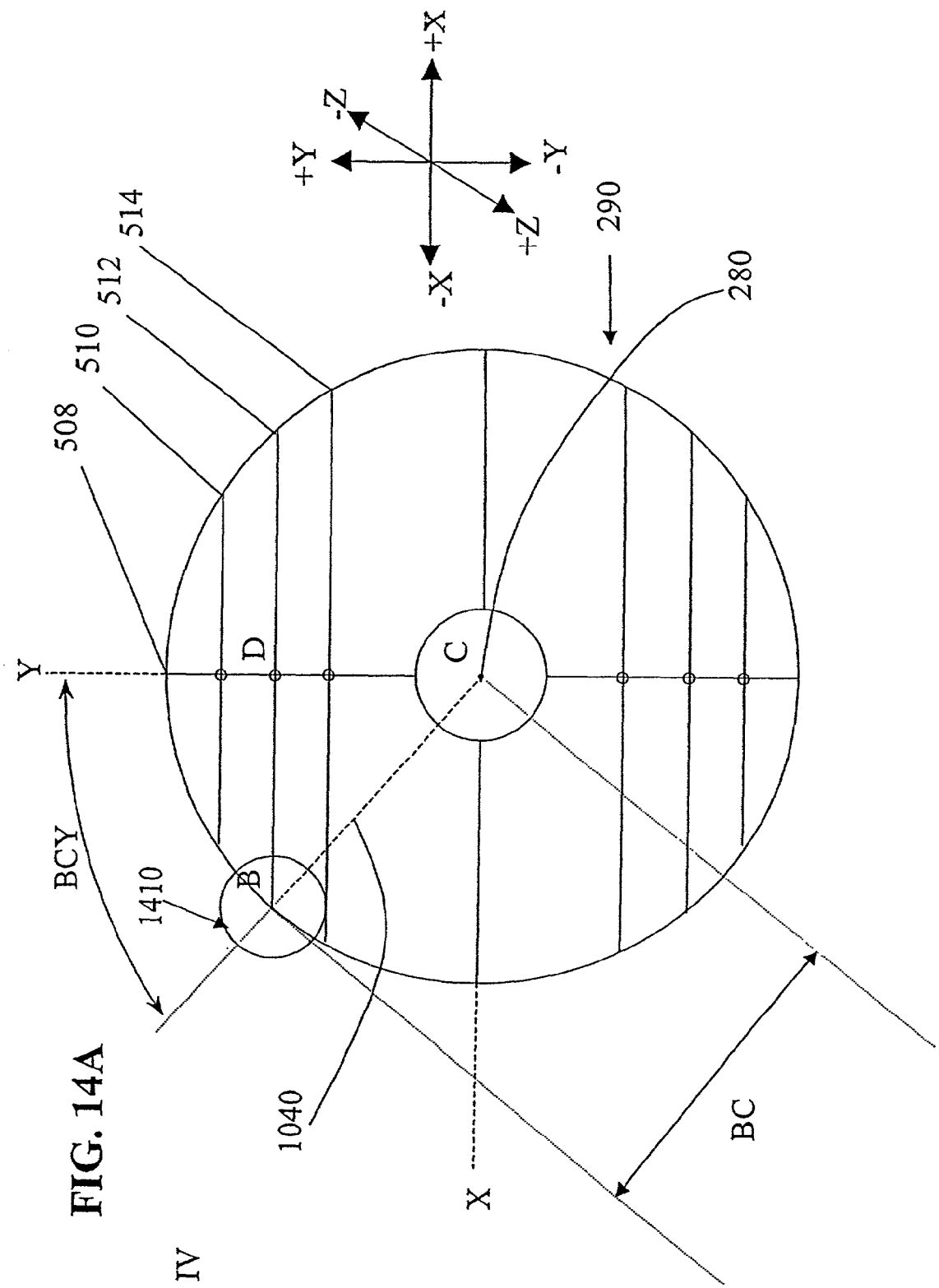
FIGS. 14A–14E are schematic perspective views of the relative positioning of the imaging grid, the fluoro axis and the target.
Figures 14B, 14C, 14D:
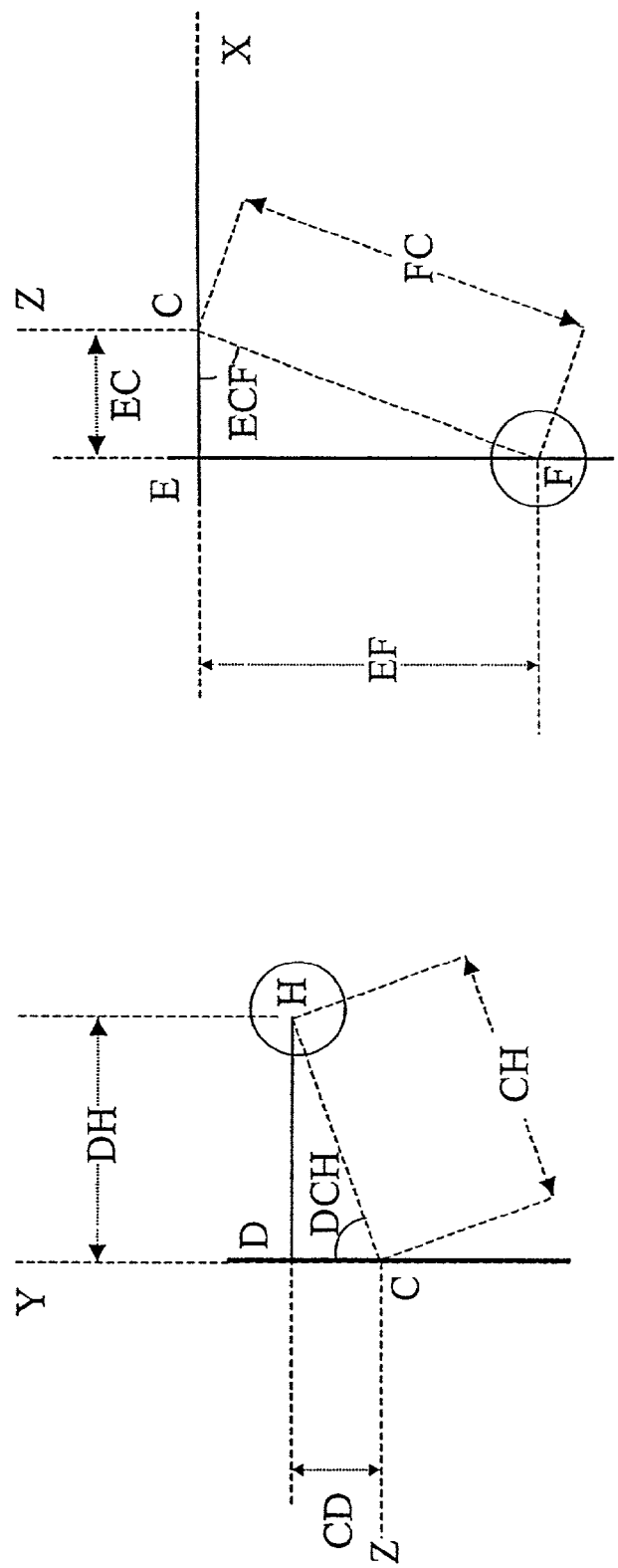
Figure 14E:
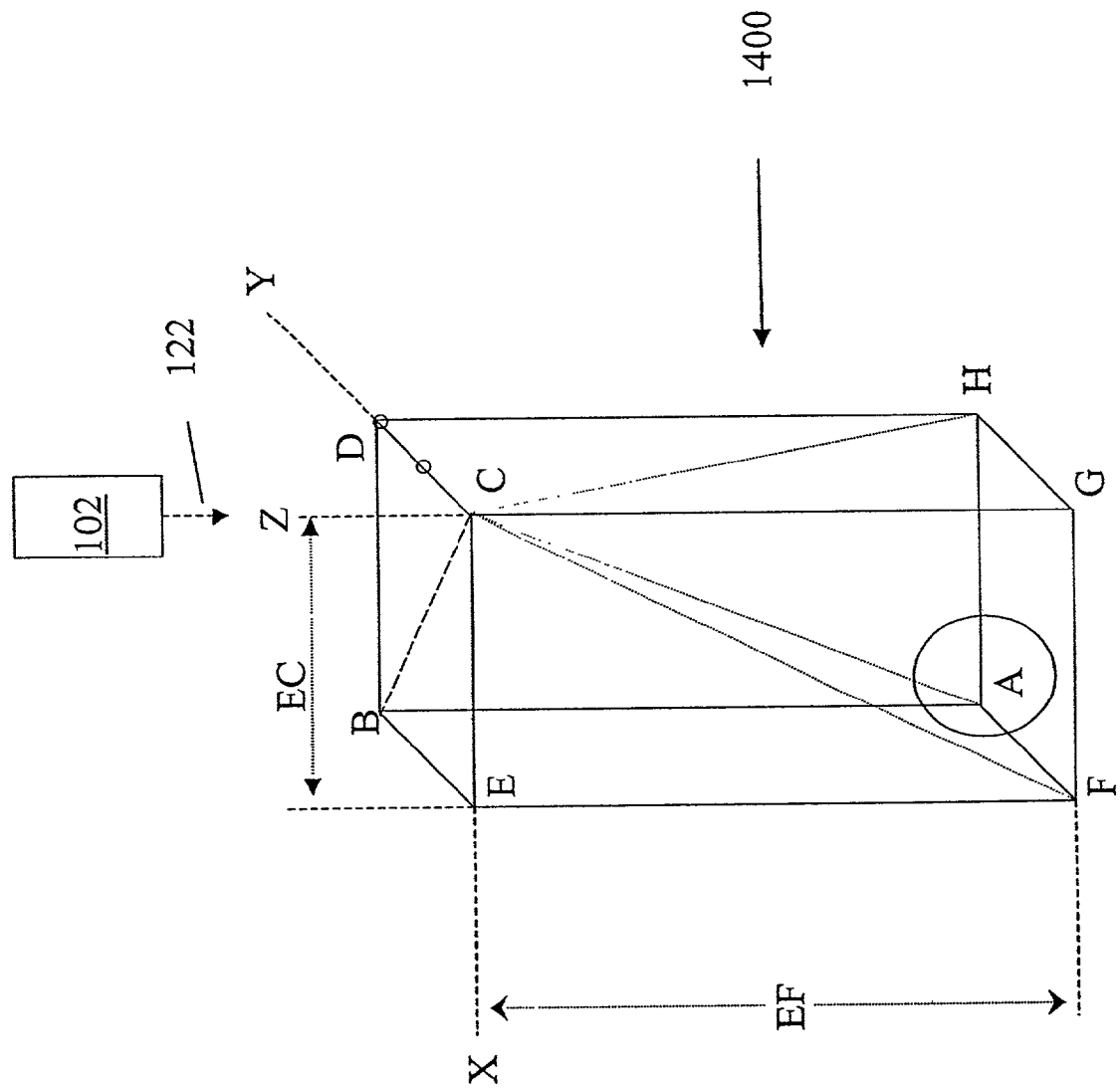

Referring to FIG. 14E, the isometric view of the aiming line BC, the upper left-hand quadrant of the imaging grid ECDB and the target A are shown. The target A, the upper left hand quadrant of the imaging grid ECDB and the aiming line BC are enclosed in a rectangular geometric box 1400 to illustrate their geometric relationships. The fluoroscope emitter 102 is shown to be positioned in a downward vertical (AP) position and is not shown to scale. The fluoroscope emitter 102 projects a fluoro beam 122 which encompasses the distal portion of the needle guiding device 126. The X and Y axis crosshairs of the imaging grid ECDB are represented by the lines EC and CD respectively. Line EC has a length of 2.0960. Line EF has a length of 4.5202.

Referring to FIG. 14A, a top perspective view of FIG. 14E is shown. With respect to the direction of the fluoro beam 122, the guide point B is positioned to be aligned with the target A (best shown in FIG. 14E). The aiming line BC intersects the guide point B and the center point C. The target A is represented as the center of a sphere 1410. When located within the fluoro beam 122, the northwest quadrant of the imaging grid ECDB and the aiming line BC are visible via the fluoroscope display 116. Line BC has a length of 2.6395 and angle BCY has a size of 53 degrees.

Referring to FIG. 14B, a side view perspective of FIG. 14A is shown. The Y axis of the northwest quadrant of the imaging grid ECDB is represented by line CD. Line CD has a length 1.6043. Line CH has a length of 4.7965. Line DH has a length 4.5202. Angle DCH has a size of 70 degrees.

Referring to FIG. 14C, an auxiliary view of FIG. 14A is shown. The X axis of the imaging grid ECDB is represented by line EC. Line EC has a length of 2.0960. Line EF has a length of 4.5202. Line FC has a length of 4.9825. Angle ECF has a size of 65.1230 degrees.

Referring to FIG. 14D, a front view perspective of FIG. 14A is shown. The aiming line BC has a length of 2.6395. The depth of the target A below the imaging grid is represented by line AB. Line AB has a length of 4.5202. The needle insertion length is represented by line AC. Line AC has a length of 5.2344. The depth angle is represented by angle BCA. Angle BCA has a size of 60 degrees.

Referring again to FIG. 14E, the fluoroscope emitter 102 is positioned downward and vertical to the earth. A fluoro beam 122 intersects the northwest quadrant imaging grid ECDB, target point B and the target A. The Y axis of the imaging grid CD is aligned with line GH of the geometric box 1400. The fluoroscope emitter 102, while emitting a fluoro beam 122, is rotated in the clockwise direction about the Y-axis of the fluoroscope 100 until it intersects the guide point D and the target A. Also, the line CD and the line FA are aligned with respect to the direction of the fluoro beam 122. The size of the rotated angle within the X-Z plane of movement of the fluoroscope arm 106 can be read off a fluoroscope angle indicator. Angle ECF is equal to 90 degrees minus the rotated fluoroscope angle.

Angle DCH can be determined in a similar manner. In the downward vertical (AP) position, the fluoro beam 122 intersects the imaging grid ECDB and the guide point B. The guide point B and the target A are aligned with respect to the position of the fluoro beam 122. The X axis crosshair EC of the imaging grid is aligned with the line GF with respect to the direction of the fluoro beam 122. The fluoroscope emitter 102 while emitting a fluoro beam 122 is rotated in the counter clockwise direction (out of paper direction in FIG. 14E) about its X-axis until it intersects both the X axis crosshair EC of the imaging grid 290 and line AH. Lines EC and AH are aligned with respect to the position of the fluoro beam 122. The rotated angle within the Y-Z plane of movement of the fluoroscope arm 106 can be read off a fluoroscope angle indicator.

Angle DCH is equal to 90 degrees minus the rotated fluoroscope angle within the Y-Z plane of movement of the fluoroscope arm 106. The rotated angle of the fluoroscope is equal to angle GCH. Depth CG can be determined by depth CG=(CD)*(cot ∠GCH). The depth or length of the trajectory of the target A can be useful when mapping the calyx or stones of the kidney to determine what length needle to use or if the needle will reach the intended target A. Rotating the aiming line BC of the guide platform 230 to intersect the guide point B sets the direction of the guide shaft 232 towards the guide point B. The depth angle 416 remains to be determined to define a needle insertion trajectory to the target A.

Referring again to FIG. 14E, the fluoro beam 122 is aligned to a needle insertion trajectory AC intersecting the target A. The fluoro beam 122 is repositioned from a first position aligned with the line CG representing the downward vertical fluoro beam direction to a second position aligned with the line AC. The line AC represents a needle insertion trajectory AC. To reposition the fluoro beam 122, the fluoro beam 122 is rotated in the X-Z plane about the Y-axis and rotated in the Y-Z plane about the X-axis. The fluoroscope emitter 102 is first positioned to intersect both the Y axis crosshair CD of the northwest quadrant of the imaging grid ECBD and the target A. Next, the fluoroscope emitter 102 is positioned to intersect both the X axis crosshair EC and the target A.

Figure 15A:
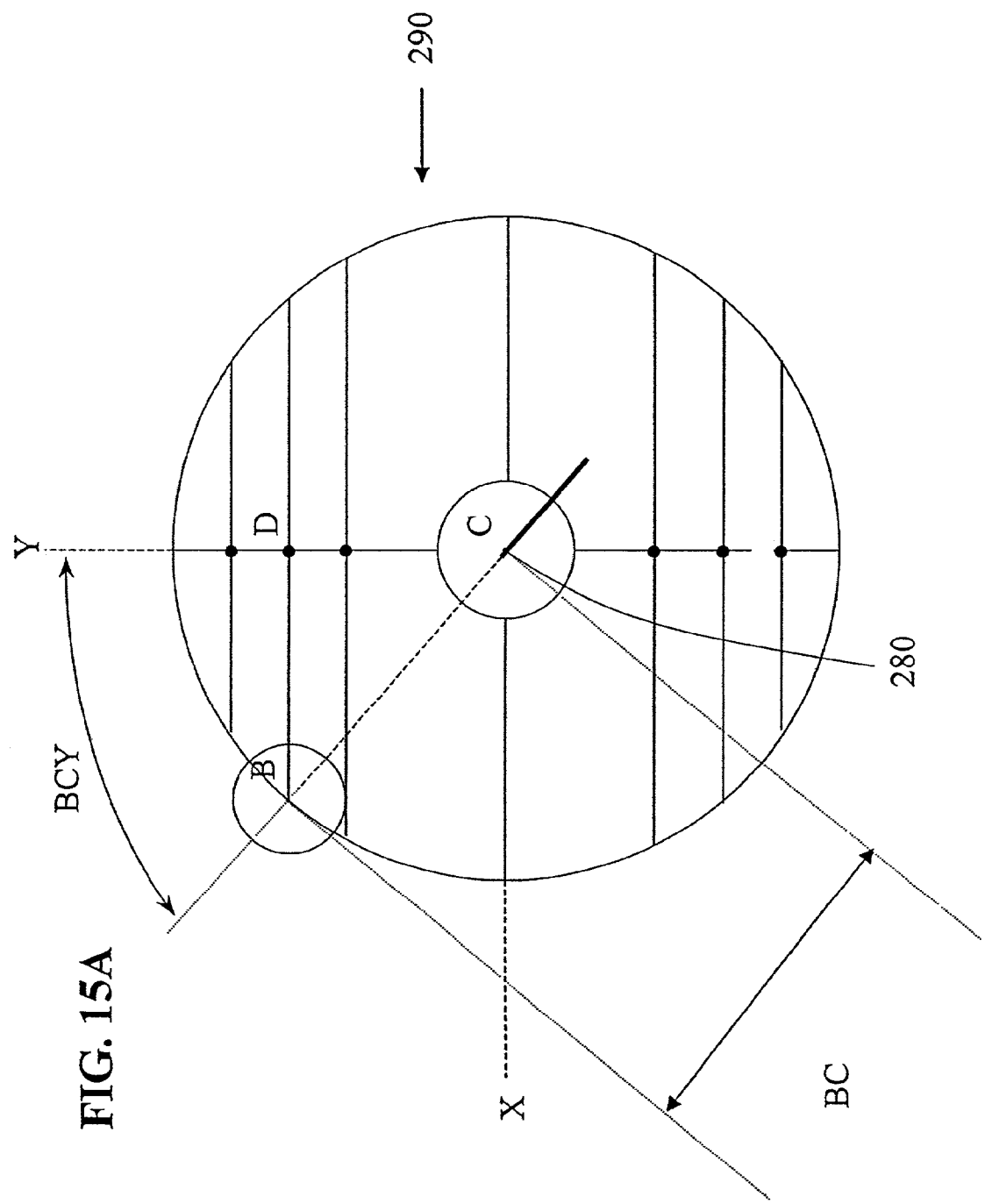
FIGS. 15A–15J are schematic perspective views of the relative positioning of the imaging grid, the fluoro axis and the target while performing steps to align the guide shaft towards a target.
Figure 15B:
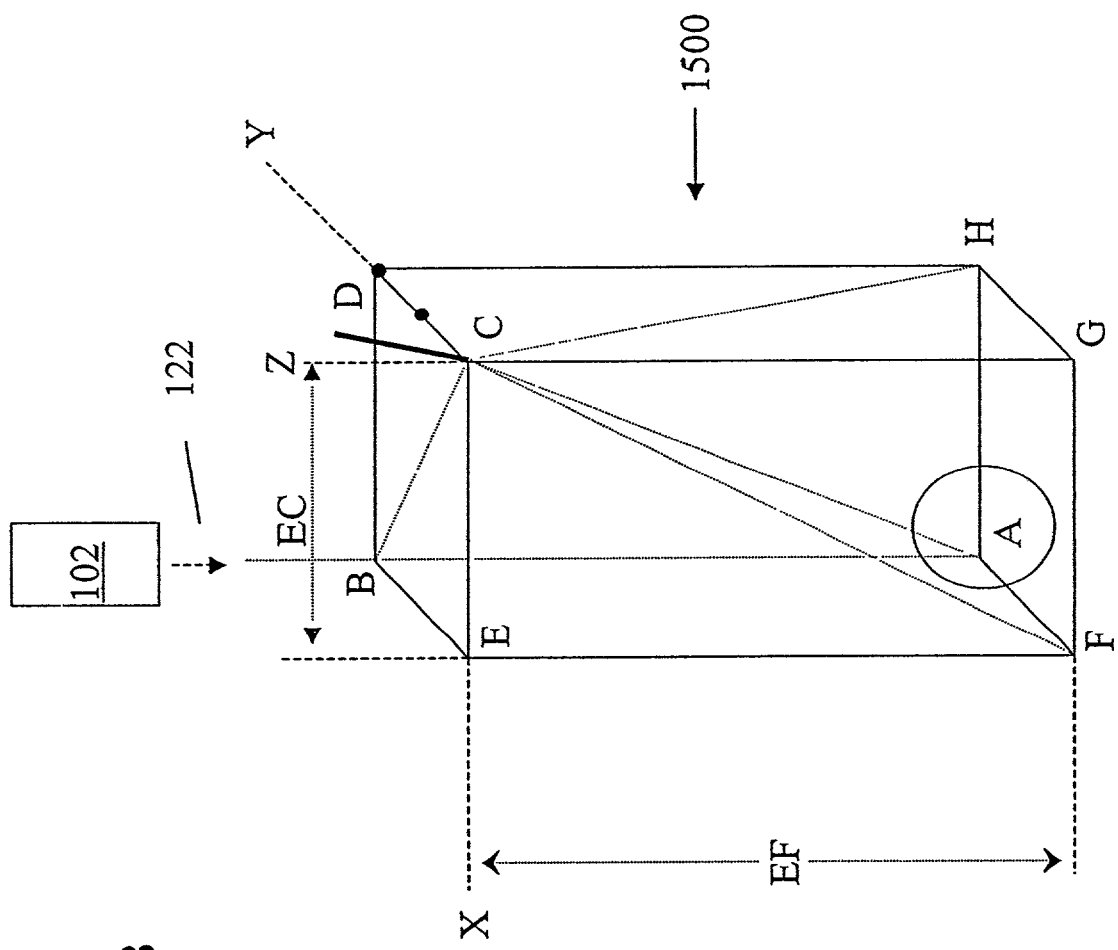
Figure 15C:
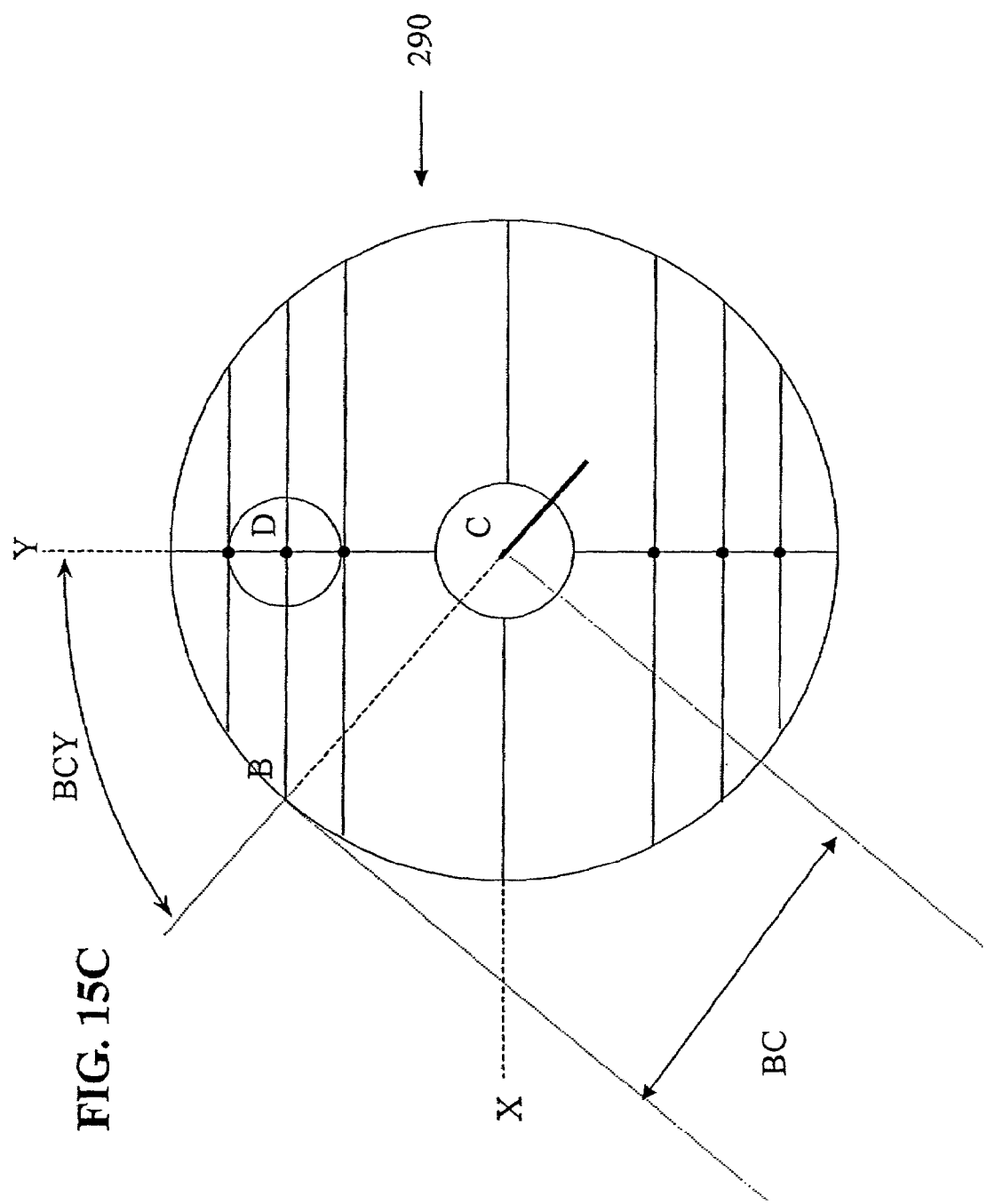

Referring to FIGS. 15A–15J, the relative positioning of the needle guiding device 126, the fluoro axis 122 and the target A are illustrated while performing steps to align a needle 442 towards a target A. In both FIG. 15A and FIG. 15B the fluoroscope arm 106 is in the downward vertical (AP) position. The fluoro beam 122 intersects the imaging grid 290, guide point B, the center point and common point C and the target A. With respect to the direction of the fluoro beam 122, the imaging grid axis CD intersects length GH of the geometric box 1500. The fluoroscope emitter 102 while generating a fluoro beam 122 is rotated in the clockwise direction about its Y-axis until the point D of the crosshair intersects the center of target A as seen in FIG. 15C.

Figure 15D:
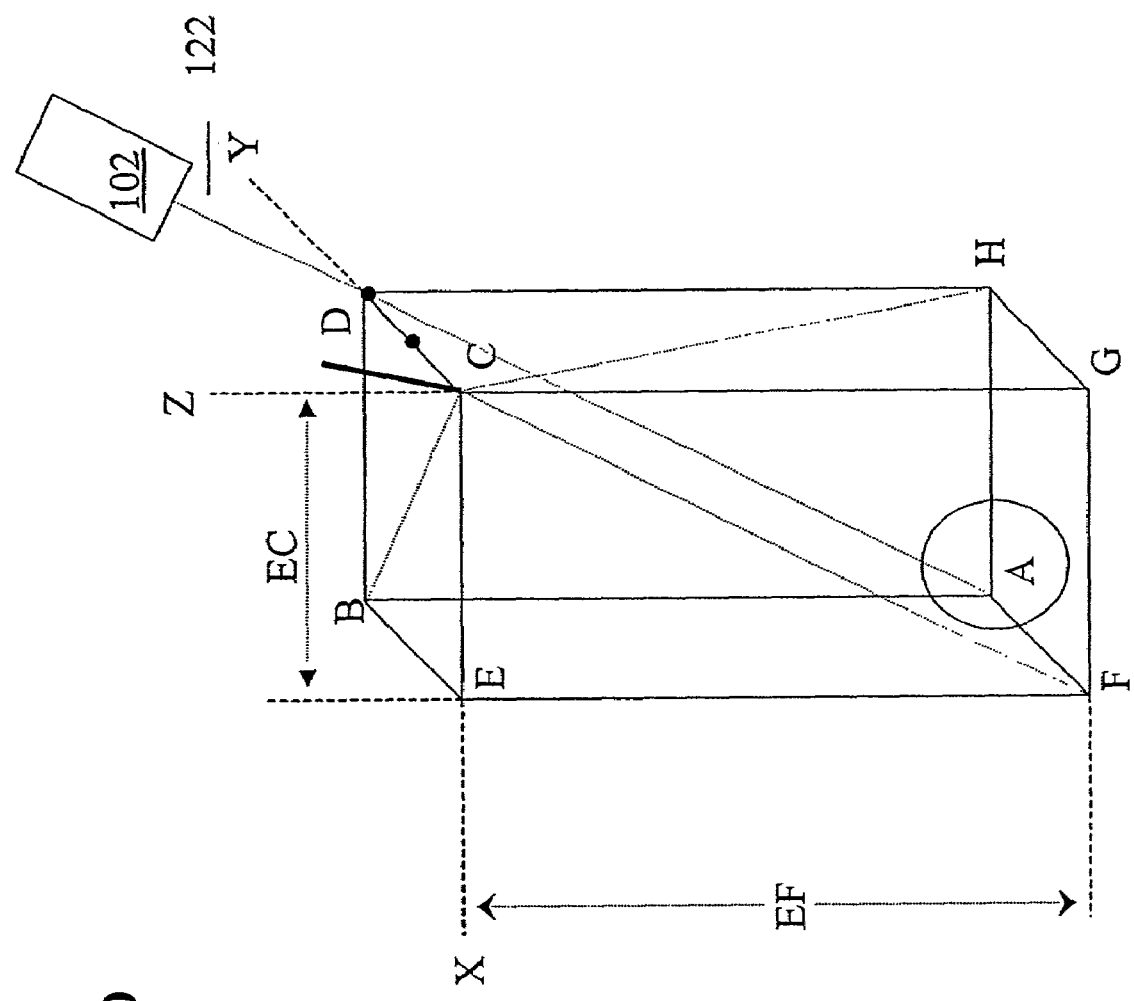

The rotated fluoro beam position is identified as position 2 as shown in FIG. 15D. Note the length and direction line CF equals the length and direction of line DA. If point D does not align with the target A in position 1 as guide point B aligns with the target A in position 2, then the axes of the imaging grid 290 and of the fluoroscope 100 are misaligned. In position 2, fluoro beam 122 is now positioned in line with the plane AFCD. The trajectory AC lies along or on plane AFCD.

Figure 15E:
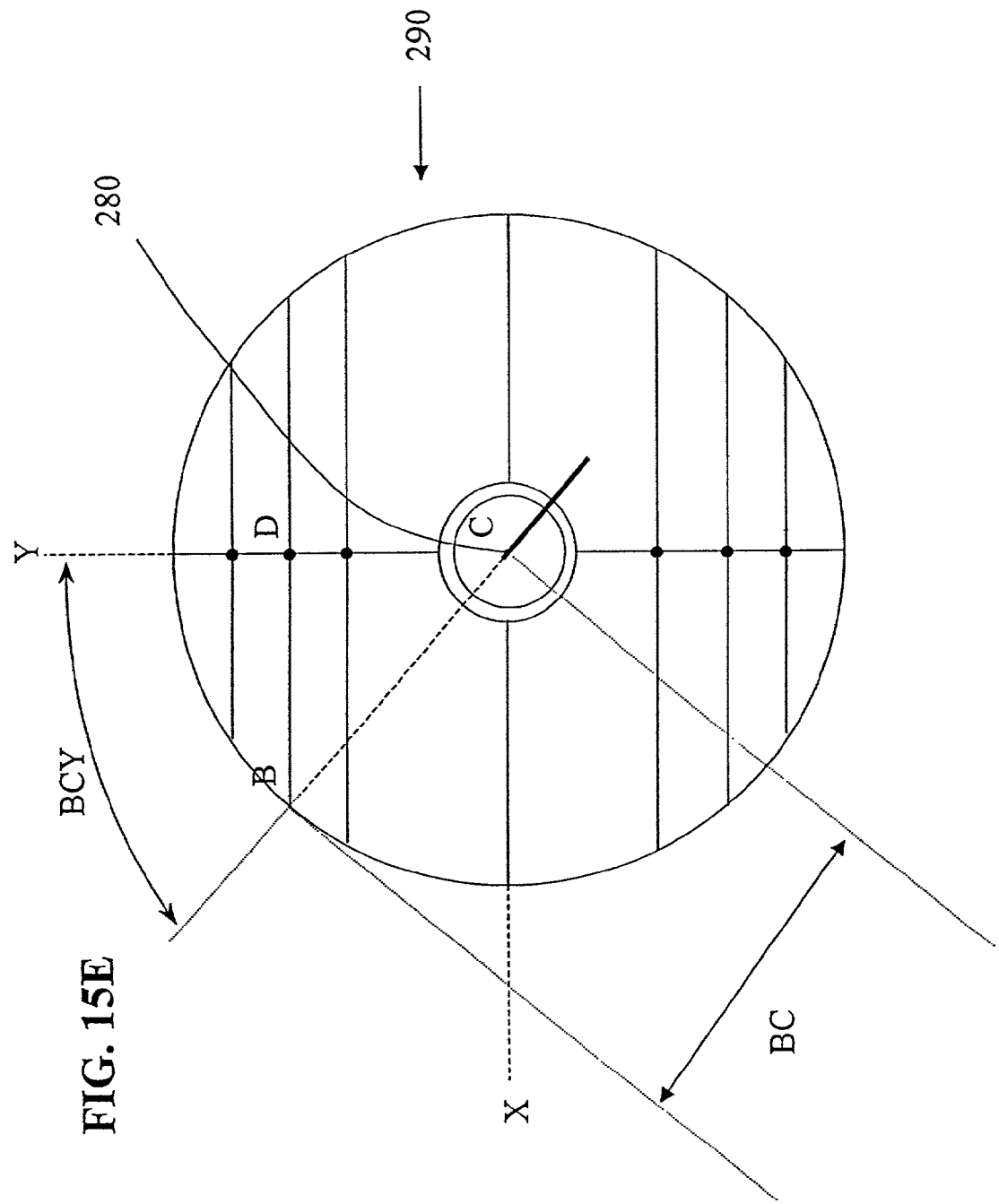
Figure 15F:
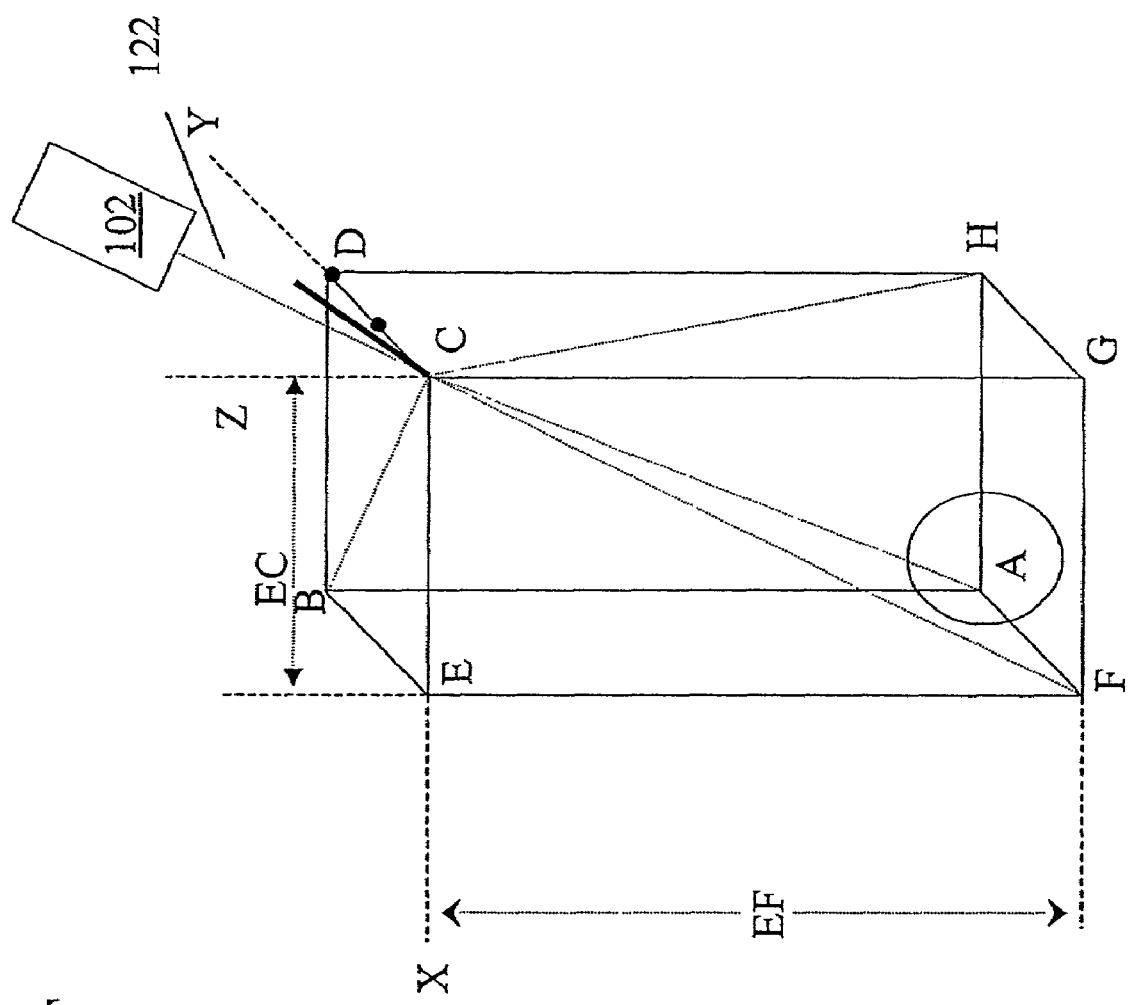
Figure 15G:
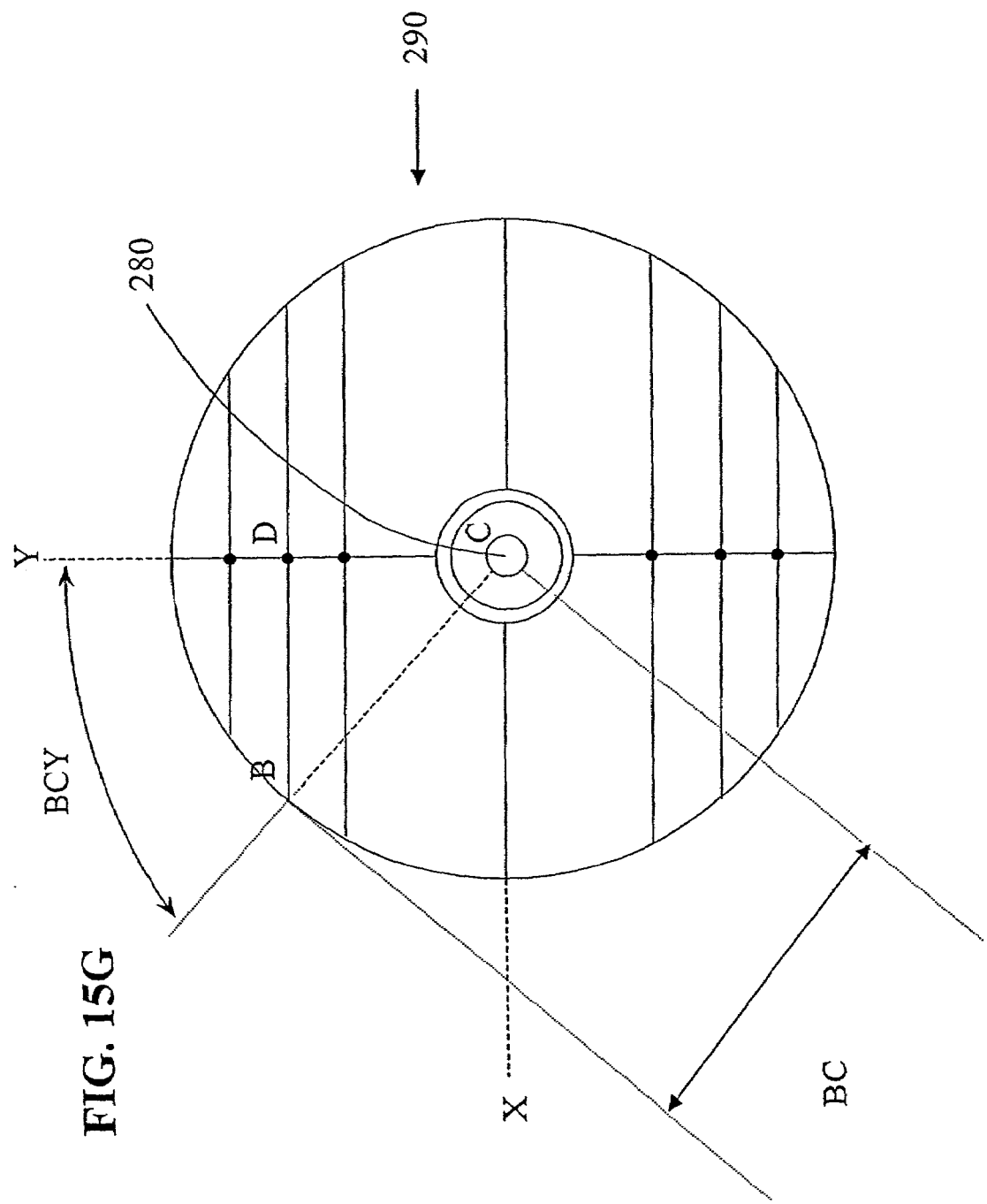
Figure 15H:
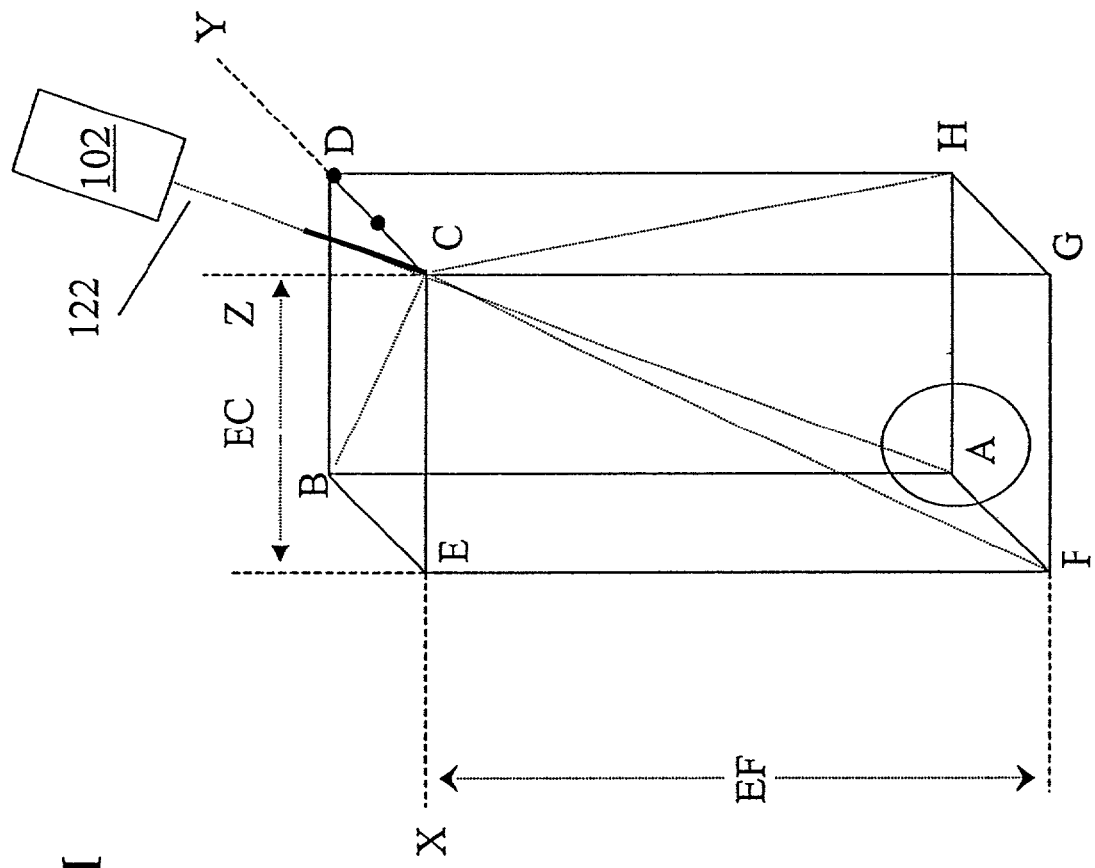

The fluoroscope arm 106 located in position 2 is rotated in the counter clockwise direction (out of the paper) about the X-axis in FIG. 15D until the axis CE of the imaging grid intersects the center of target A in FIG. 15E. The target in this case is directly seen to be in line with the smaller circle of the grid 290. FIG. 15F shows the isometric view of FIG. 15E with the axis of the fluoroscope arm 106 in line with AC. To align the guide shaft 232 in line between the fluoroscope head 102 and the target. The guide shaft 232 is rotated about the pivot cylinder 234 by the guide rod 236 to prevent the hand of the medical professional from contacting the fluoro beam 122. The guide shaft 232 is rotated until the guide shaft passageway 320 is aimed directly at the target A and seen as such in the fluoro image in FIG. 15G. The guide rod 236 is locked into this location.

Figure 15I:
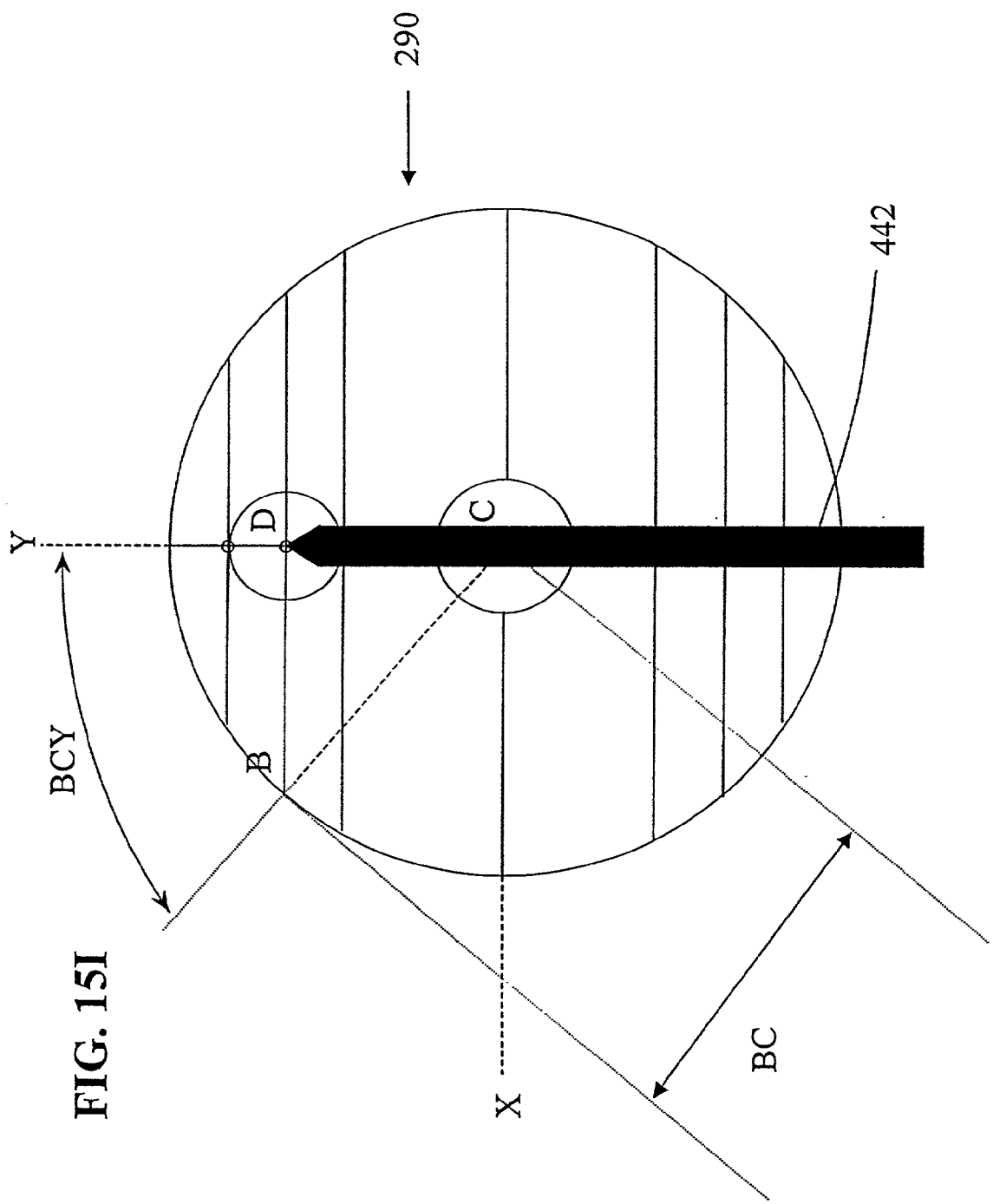
Figure 15J:
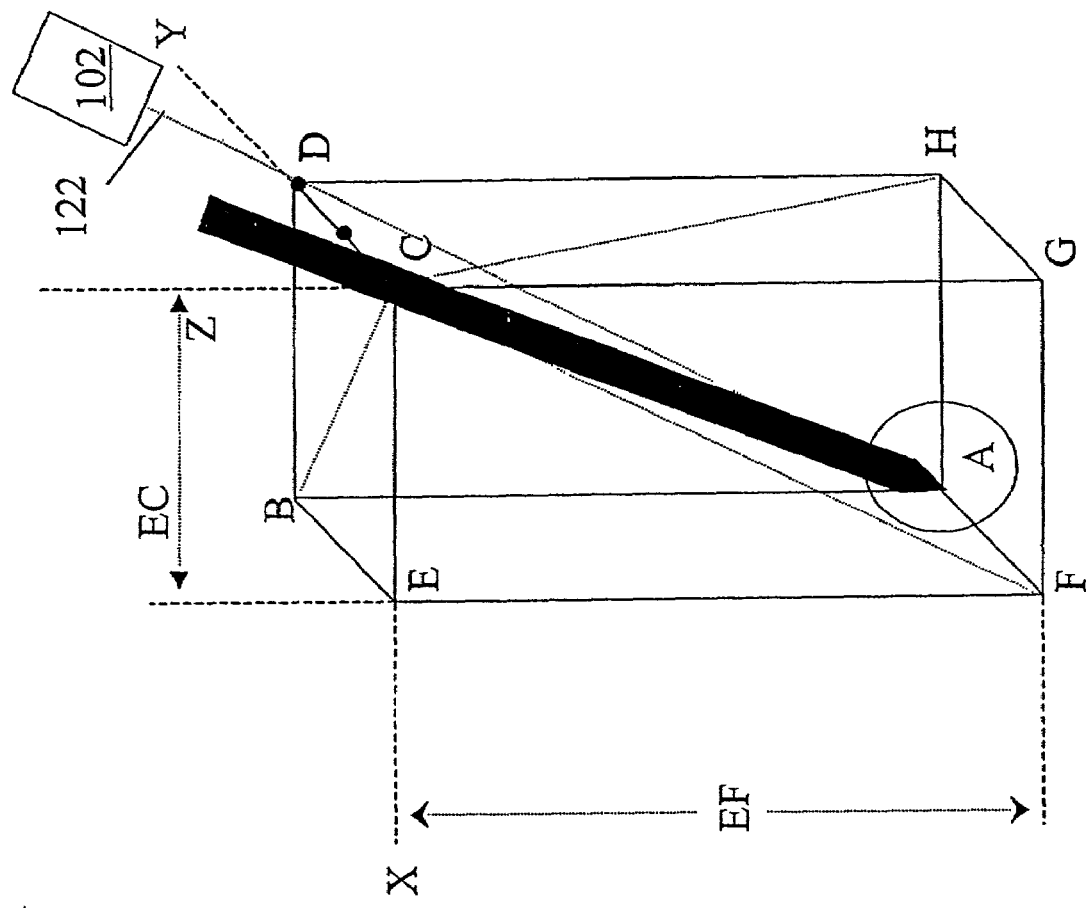

Before inserting the needle, the fluoroscope arm 106 is rotated back to position 2 as shown in FIG. 15J. The needle is inserted slowly and can be viewed via the fluoroscope display 116. From the fluoroscope display 116, the needle appears to travel along the Y-axis of the grid 290 as shown in FIG. 15I. Actually, the needle travels along trajectory AC as shown in FIG. 15J. Variation from the appearance of the needle traveling along the Y-axis could indicate an incorrect needle insertion trajectory. Insertion of the needle is terminated when it is seen to have contacted point D which is perpendicular (normal) to the guide line connecting guide point B and D.

Referring to FIGS. 16A–16E, the relative positioning of the needle guiding device 126, the fluoro axis 122 and the target A is shown while performing steps to align a needle towards a target. The procedure starts with the selection of a guide point as a starting point along the Y axis of the device 126.

Figure 16A:
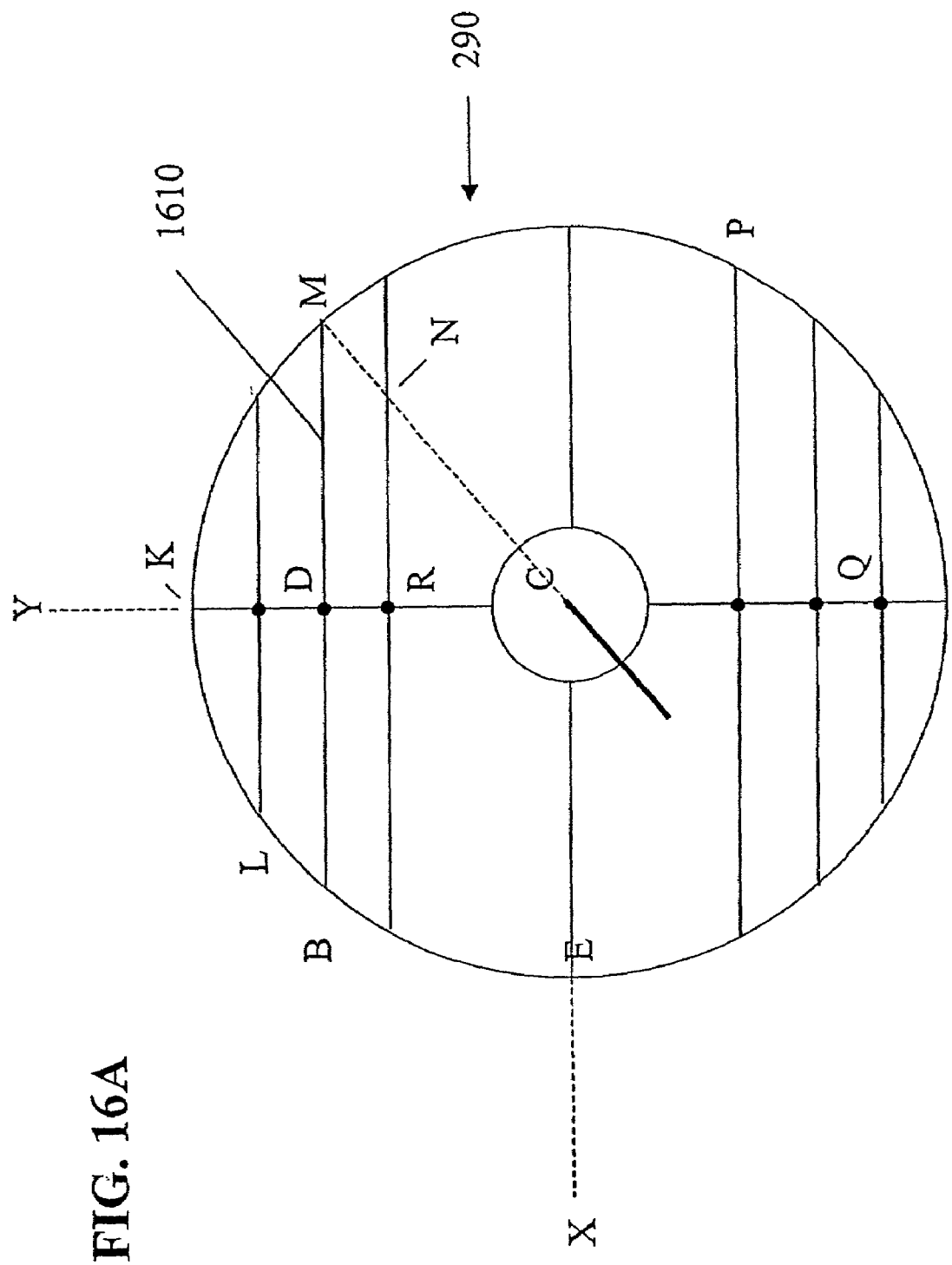
FIGS. 16A–16E are schematic perspective views of the relative positioning of the imaging grid, the fluoro axis and the target while performing steps to align the guide shaft towards a target using a guide point located along the Y axis of the imaging grid.

Referring to FIG. 16A, other guide points such as M, L, K, P, Q, R and N are shown. Use of guide point M or guide point B requires a 2 plane alignment procedure that will use guide point D for alignment with the Y-axis. Start point M may be used to access the lower pole 1322 as shown in FIG. 5. Guide point N is created by the intersection of the aiming line 240 with the guide line 1610 of the imaging grid 290. Intersecting the aiming line 240 with guide point N defines the same direction along the imaging grid 290 as when intersecting guide point M, but will have a larger associated depth angle than guide point M.

Use of guide point N as a target point will require use of guide point R for alignment with the Y-axis. Alignment of the fluoro axis 124 with guide point R can be used as a needle insertion viewing fluoro axis position. Start point P is similar to point B for the left handed physicians who would hold the device handle 210 with their right hand and insert the access needle with their left hand.

Guide points R, D, K are located on the Y-axis of the grid 290 and could be used as target point to access the mid calyx 1324 of the right kidney 1320 as shown in FIG. 5. The aiming line 240 is rotated about the rotation axis 228 from a position intersecting point M to a position intersecting point K to align the guide shaft 232 in the direction of guide point D.

Figure 16C:
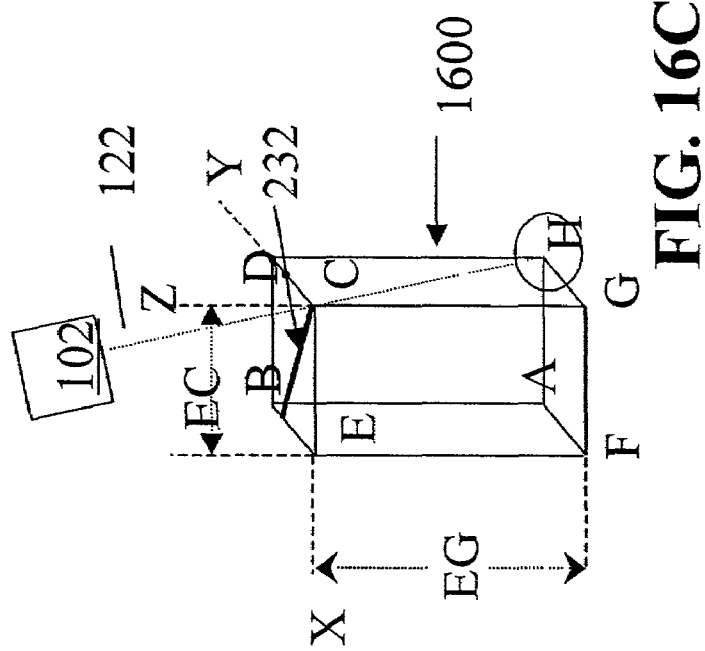
Figure 16B:
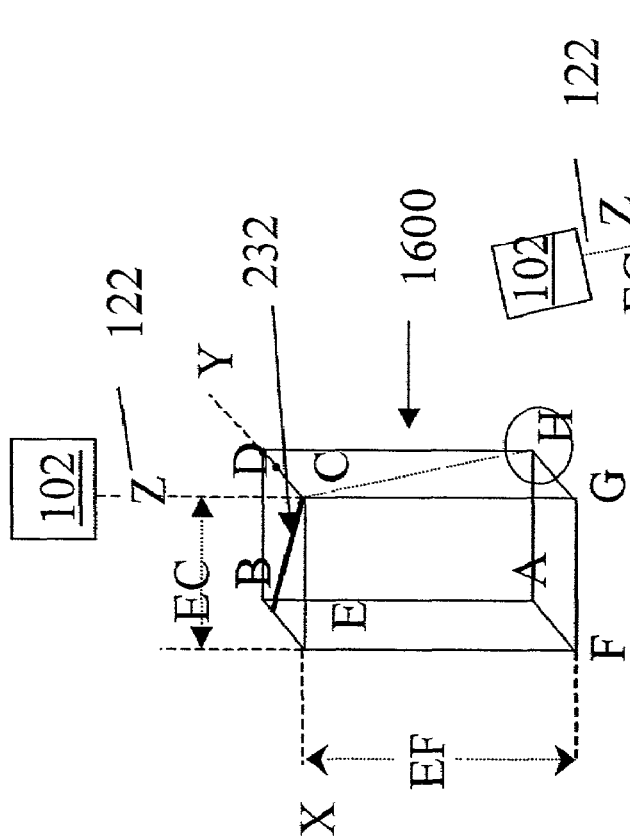
Figure 16D:
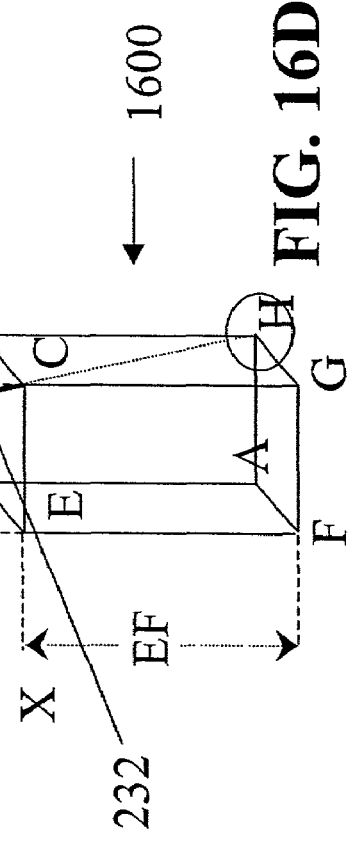
Figure 16E:
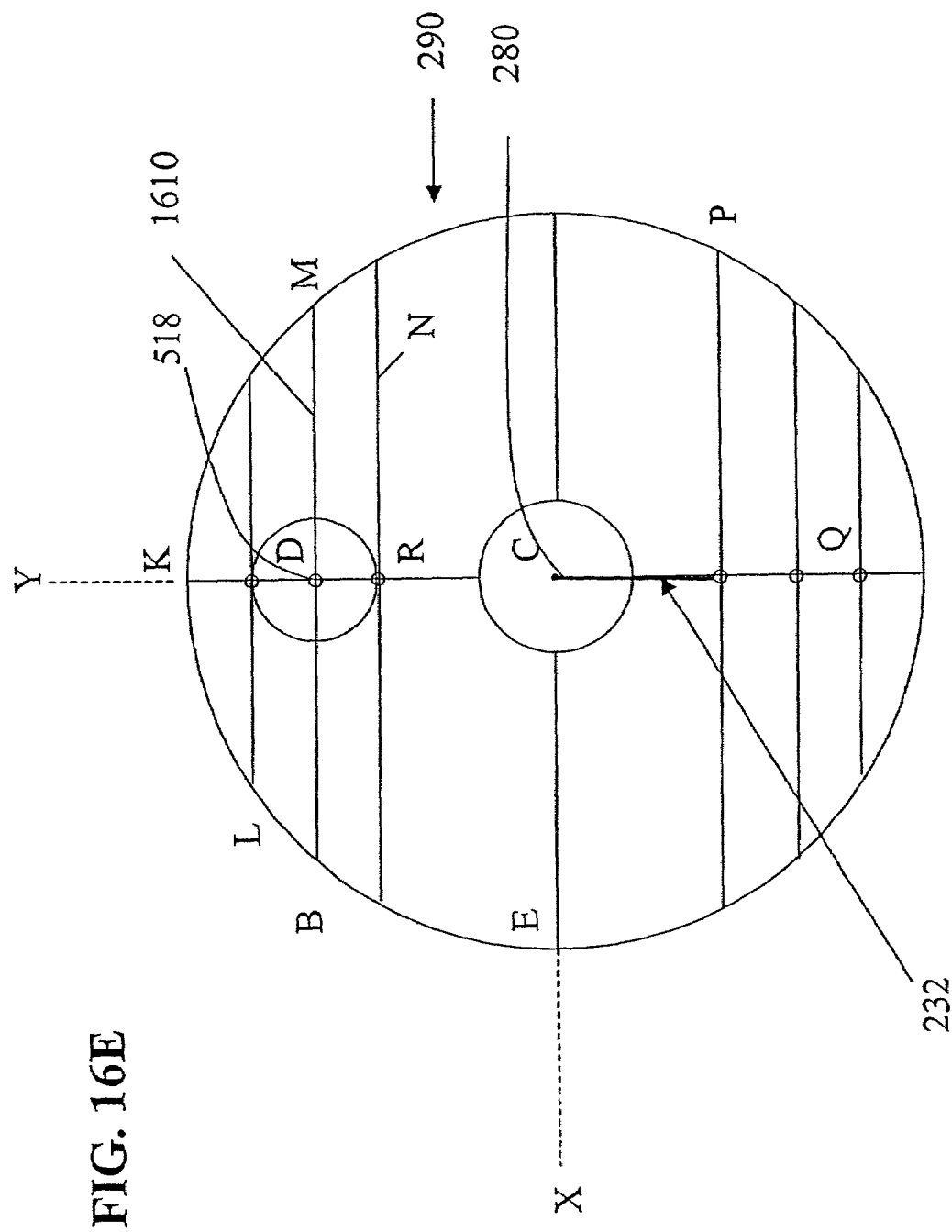

Referring to FIG. 16E, the aiming line 240 is directed at point K, start points K, D and R are in the direction of the guide shaft 232 where point Q is proximal to the direction of the guide shaft 232. Use of the guide point R as a target point requires a larger depth angle than use of guide point D. Use of guide point D would be have a larger depth angle than use of guide point K. Guide point D is chosen as target point and aligned with the target H in the while the fluoro axis 124 is in the downward vertical (AP) position.

Referring to FIG. 16B, the isometric view of FIG. 16E is shown. The required needle insertion trajectory is represented by the length of the line CH. Line CH extends from the center point C to the target H, which lies on plane CDHG. The Y-axis of the imaging grid 290, guide point D, the Y-Z plane of fluoroscope arm 106 movement and the fluoro axis 124 all lie in the same plane CDGH. To align the fluoro axis 124 to the trajectory CH, the fluoro axis 124 is rotated in the Y-Z plane about the X-axis of the fluoroscope 100 until the guide crosshair CE intersects AH or target H of the geometric box 1600 target as shown in FIG. 16C. The aligned guide shaft 232 in FIG. 16E shows that it is already in the same plane as the target H, but not necessarily aimed directly at target H.

The guide shaft 232 is positioned via the guide rod 236 until the radiopaque portion 340 of the guide shaft 232 is seen as its smallest profile (circle) intersecting the target H from the fluoro axis 124 position as seen in FIG. 16D. The guide shaft 232 is locked into a position by locking the position of the guide rod 236 by turning it along its longitudinal axis in the clockwise direction (best seen in FIG. 3B). The needle insertion trajectory is confirmed by viewing the guide shaft 232 represented by its smallest profile as a circle, directed toward the target H via the fluoroscope display 116. The fluoro axis 124 is re-positioned to the downward vertical (AP) position to view the needle advancing towards and entering the target calyx H, similar to that shown in FIG. 15I.

A guide point is selected as target point regardless of whether a two plane access procedure (best seen in FIG. 15B to FIG. 15J) or a single plane access procedure (best seen in FIG. 16B to FIG. 16D) is used. The guide point will be chosen on the half of the imaging grid 290 that is located closer to the spine of the patient 110 (best seen in FIG. 5). The guide shaft 232 is directed towards that half of the imaging grid 290 towards a calyx as a target.

Referring to FIG. 16A, when using two plane access to a kidney as a target, a guide point such as B, L, or M is selected and aligned with the target while the fluoro axis 124 is in a downward vertical (AP) position. This is the first fluoro axis position. The fluoro axis 124 is rotated from the first fluoro axis position toward the Y-axis until the fluoro axis 124 intersects both the Y axis of the imaging grid 290 and the target. If guide point M is selected as the target point, then the fluoro axis 124 is rotated counter clockwise towards point D from point M, until it intersects point D and the target. If guide point B is selected as the target point, then the fluoro axis 124 is rotated clockwise towards point D from point B until the fluoro axis 124 intersects point D and the target. This is the second fluoro axis position.

From its second position, the fluoro axis 124 is rotated towards the center C and the medical professional 108 until the fluoro axis 124 intersects the X axis of the imaging grid 290 and the target H. This is the third fluoro axis position. The direction of the fluoro axis rotation between the second and third fluoro axis position is 90 degrees apart from the direction of fluoro axis rotation between the first and the second fluoro axis position. The fluoro axis 124 is now aligned with the needle insertion trajectory. Next, the position of the guide shaft 232 is aligned to the third position of the fluoro axis 124 and locked. Next, the fluoro axis is rotated back to the second fluoro axis position to serve as the needle insertion viewing fluoro axis position.

Still referring to FIG. 16A, one of the guide points K, D or R can be selected for single plane access of the kidney as a target. A guide point is selected aligned with the target H while the fluoro axis 124 is in the downward vertical (AP) position. This is the first fluoro axis position of the single plane procedure. The fluoro axis 124 is rotated towards the center C until the fluoro axis 124 intersects the X axis of the imaging grid 290 and the target H. The fluoro axis 124 is now in line with the needle insertion trajectory. This is the second fluoro axis position of the single plane procedure. Next, the guide shaft 232 is then aligned to the fluoro axis 124. The fluoro axis 124 is rotated back to the first fluoro axis position of the single plane procedure to serve as the needle insertion viewing fluoro axis.

The invention can be used as a training device and method for those who are less skilled than those skilled in the art of guiding a probe 442 towards a target 410. The invention can also be used to reduce a three dimensional problem of verifying contact between a probe and a target into a simplified two dimensional problem using the fluoroscope display 116. The invention can also be utilized to teach a triangulation viewing technique for verifying the movement of a probe 442 as it moves along a trajectory 414 towards a target 410. The invention can assist the medical professional 108 by providing a step by step approach for guiding a probe 442 to a target. The invention also assists the medical professional 108 by reducing the number of probe insertions and the amount of trial and error effort required to make contact between the probe 442 and a target 410.

While the invention has been shown and described with reference to certain embodiments, it should be understood that various changes in form and detail may be made without departing from the spirit and scope of the invention.

What is claimed is:

1. A needle guiding apparatus comprising:
a base defining an opening therethrough;
an outer rim disposed substantially completely around a perimeter of the base, the base and the outer rim defining an aperture between the perimeter and the outer rim, and the base being rotatable relative to the outer rim;
a guide platform disposed adjacent to the opening, the guide platform being rotatable about a rotation axis, the rotation axis extending through the opening and having a common point along the rotation axis;
a pivot disposed at least partially within the guide platform and being rotatable about a pivot axis that is substantially perpendicular to the rotation axis; and
a guide shaft disposed at least partially within the pivot and extending along a longitudinal axis from a first end of the guide shaft to a second end of the guide shaft, the longitudinal axis intersecting with the rotation axis at the common point, the guide shaft being rotatable within a plane defined by the pivot axis, the rotation axis, and the common point, and comprising a radiopaque material between the first end and a locus along the guide shaft normal to the longitudinal axis at the common point, the radiopaque material extending to the locus, the locus located immediately adjacent to a material being less radiopaque than the radiopaque material.

2. The apparatus of claim 1 wherein the common point is located at the second end.

3. The apparatus of claim 1 wherein the pivot axis intersects the rotation axis at the common point.

4. The apparatus of claim 1 wherein the guide shaft comprises an inner wall of the pivot forming a bore.

5. The apparatus of claim 1 wherein the guide shaft is disposed at least partially within an inner wall in the pivot forming a bore.

6. The apparatus of claim 1 wherein the entire guide shaft between the first end and the locus comprises the radiopaque material.

7. The apparatus of claim 1 wherein the guide shaft is rotatable about the rotation axis and the pivot axis.

8. The apparatus of claim 7 further comprising a guide rod that is connected to the pivot and that is rotatable about the rotation axis and the pivot axis to transfer rotational movement to the guide shaft.

9. The apparatus of claim 8 further comprising a guide rod lock for preventing movement of the pivot.

10. The apparatus of claim 1 further comprising a grid disposed about the rotation axis.

11. The apparatus of claim 10, wherein the grid is adjacent to a surface of the base.

12. The apparatus of claim 11, wherein the grid is located along a top surface of the base.

13. The apparatus of claim 10, wherein the grid comprises at least one marking configured to assist in guiding the needle.

14. The apparatus of claim 1 further comprising a shaft connected to the base, the shaft extending along a shaft axis perpendicular to the rotation axis.

15. The apparatus of claim 14, the outer rim being rotatable around the shaft axis.

16. The apparatus of claim 15 further comprising an outer rim lock for preventing relative movement between the outer rim and the base.

17. The apparatus of claim 1 further comprising a radiopaque point disposed proximate the guide platform.

18. The apparatus of claim 1 further comprising a radiopaque line segment disposed proximate the guide platform.

19. The apparatus of claim 1, wherein the outer rim surrounds the perimeter of the base.

20. The apparatus of claim 1, wherein the base is substantially circular.

21. The apparatus of claim 1, wherein the pivot is substantially cylindrical.

22. The apparatus of claim 1, wherein the guide platform defines at least one slot to accommodate movement of the guide shaft.

23. The apparatus of claim 1, wherein the guide platform defines at least one slot to accommodate movement of a guide rod connected to the pivot and rotatable about the pivot axis.

24. A needle guiding apparatus comprising:
a base defining an opening therethrough;
an outer rim disposed substantially completely around a perimeter of the base, the base and the outer rim defining an aperture between the perimeter and the outer rim, and the base being rotatable relative to the outer rim;
a guide platform disposed adjacent to the opening, the guide platform being rotatable about a rotation axis, the rotation axis extending through the opening and having a common point along the rotation axis;
a pivot disposed at least partially within the guide platform and being rotatable about a pivot axis that is substantially perpendicular to the rotation axis; and
a guide shaft disposed at least partially within the pivot and extending along a longitudinal axis from a first end of the guide shaft to a second end of the guide shaft, the longitudinal axis intersecting with the rotation axis at the common point, the guide shaft comprising a radiopaque material.

25. The apparatus of claim 24, wherein the radiopaque material is between the first end and a locus along the guide shaft normal to the longitudinal axis at the common point, the radiopaque material extending to the locus, the locus located immediately adjacent to a material being less radiopaque than the radiopaque material.

26. The apparatus of claim 24 further comprising a guide rod that is connected to the pivot and that is rotatable about the rotation axis and the pivot axis to transfer rotational movement to the guide shaft.

27. The apparatus of claim 26 further comprising a guide rod lock for preventing movement of the pivot.

28. The apparatus of claim 24 further comprising a grid disposed about the rotation axis.

29. The apparatus of claim 28, wherein the grid is adjacent to a surface of the base.

30. The apparatus of claim 29, wherein the grid is located along a top surface of the base.

31. The apparatus of claim 28, wherein the grid comprises at least one marking configured to assist in guiding the needle.

32. The apparatus of claim 24 further comprising a shaft connected to the base, the shaft extending along a shaft axis perpendicular to the rotation axis.

33. The apparatus of claim 24 further comprising a lock for preventing relative movement between the outer rim and the base.

34. The apparatus of claim 24 further comprising a radiopaque point disposed proximate the guide platform.

35. The apparatus of claim 24 further comprising a radiopaque line segment disposed proximate the guide platform.

36. The apparatus of claim 24, wherein the outer rim surrounds the perimeter of the base.

37. The apparatus of claim 24, wherein the base is substantially circular.

38. The apparatus of claim 24, wherein the pivot is substantially cylindrical.

39. The apparatus of claim 24, wherein the guide platform defines at least one slot to accommodate movement of the guide shaft.

40. The apparatus of claim 24, wherein the guide platform defines at least one slot to accommodate movement of a guide rod connected to the pivot and rotatable about the pivot axis.

* * * * *